(12) United States Patent
Lee

(10) Patent No.: US 11,666,570 B2
(45) Date of Patent: Jun. 6, 2023

(54) DIAGNOSIS AND REGULATION OF EPIDERMAL DIFFERENTIATION AND CANCER CELL ACTIVITY

(71) Applicant: The Board of Trustees of the Leland Stanford Junior University, Stanford, CA (US)

(72) Inventor: Carolyn Lee, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 208 days.

(21) Appl. No.: 16/920,220

(22) Filed: Jul. 2, 2020

(65) Prior Publication Data

US 2021/0023083 A1 Jan. 28, 2021

Related U.S. Application Data

(60) Provisional application No. 62/873,115, filed on Jul. 11, 2019.

(51) Int. Cl.
*A61K 31/506* (2006.01)
*A61K 31/444* (2006.01)
*A61P 35/00* (2006.01)

(52) U.S. Cl.
CPC .......... *A61K 31/506* (2013.01); *A61K 31/444* (2013.01); *A61P 35/00* (2018.01)

(58) Field of Classification Search
CPC ...... A61K 31/444; A61K 31/506; A61P 35/00
See application file for complete search history.

(56) References Cited

U.S. PATENT DOCUMENTS 10,030,005 B2 * 7/2018 Brubaker ................. A61P 35/00
10,112,942 B2 * 10/2018 Andrews ............. A61K 31/5377

FOREIGN PATENT DOCUMENTS

WO WO 2019/195471 * 10/2019

OTHER PUBLICATIONS

Cramer et al., Actinic keratosis: where do we stand and where is the future going to take us? Expert Opinion in Emerging Drugs, vol. 25, No. 1, pp. 49-58 (2020).*
Kato et al., RET Aberrations in Diverse Cancers: Next-Generation Sequencing of 4,871 Patients, Clin. Cancer Res. 23(8), pp. 1988-1997 (2017).*
Porcheri et al., Notch in Head and Neck Cancer, Zurich Open Repository and Archive, Part of the Advances in Experimental Medicine and Biology, pp. 1-43 (total 47 pages) (2021).*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*
Acute Leukemia, Merck Manual (Online Edition) 6 pages, pp. 1-6 (2013).*
Simone, Oncology: Introduction, Cecil Textbook of Medicine, 20th Edition, vol. 1, pp. 1004-1010, 1996.*
Lee et al. (2014) Recurrent point mutations in the kinetochore gene KNSTRN in cutaneous squamous cell carcinoma. Nat. Genet. 46, 1060-1062.
Lee et al. (2018) Cancer-Associated Long Noncoding RNA SMRT-2 Controls Epidermal Differentiation. J. Invest. Dermatol, doi:10.1016/j.jid.2018.01.003.

* cited by examiner

*Primary Examiner* — Deepak R Rao
(74) *Attorney, Agent, or Firm* — Pamela J. Sherwood; Bozicevic, Field & Francis LLP

(57) ABSTRACT

Methods are provided for treatment of skin cancers and squamous cell carcinomas by inhibition of RET activity. The treatment can reduce cancer development and progression; and can reduce metastasis and invasion, including perineural invasion.

16 Claims, 35 Drawing Sheets
Specification includes a Sequence Listing.

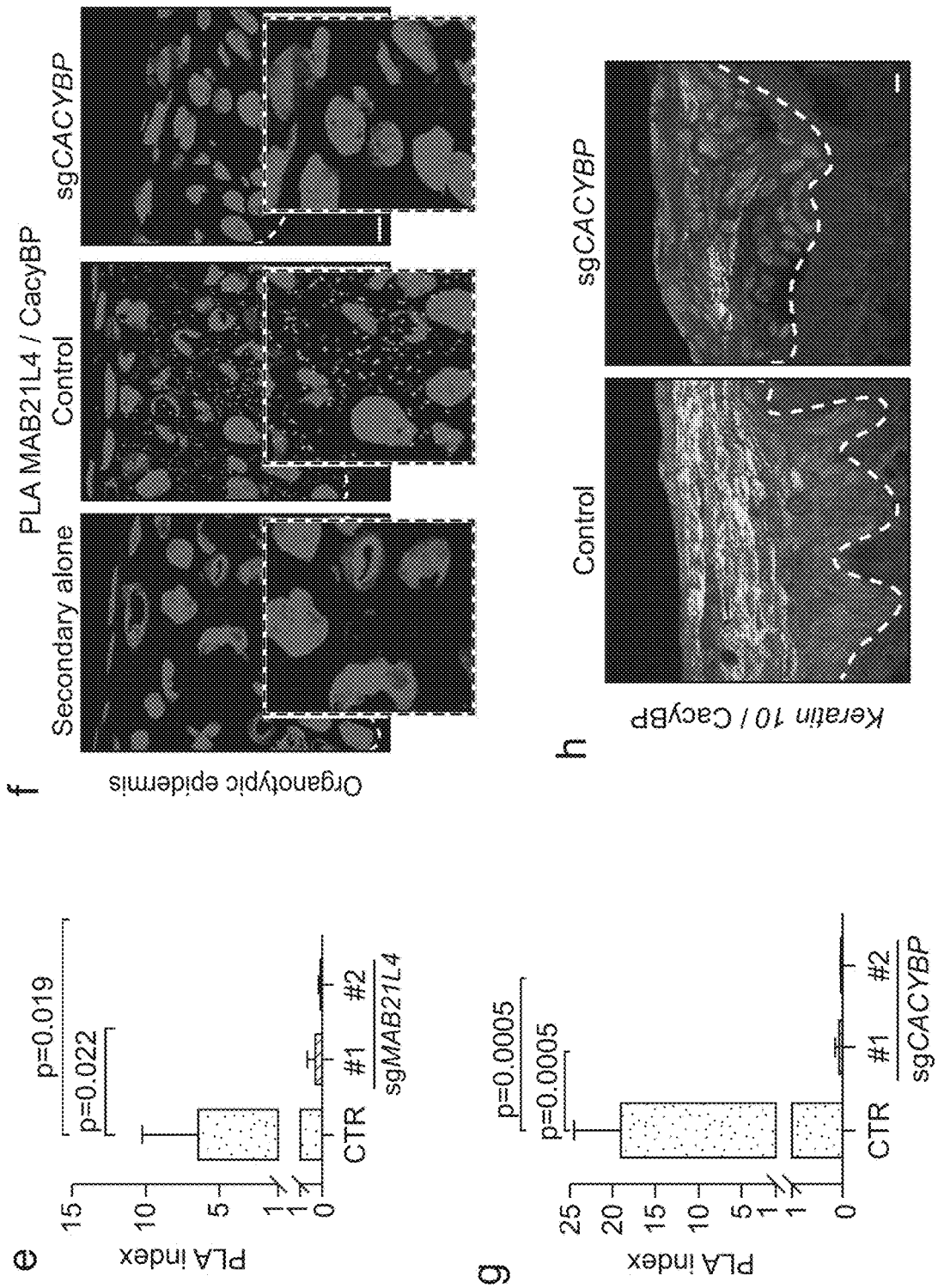

a b c

Genetic Gain-of-Function in
Oncogenic Ras-transformed tissue d d e

Normal human skin f

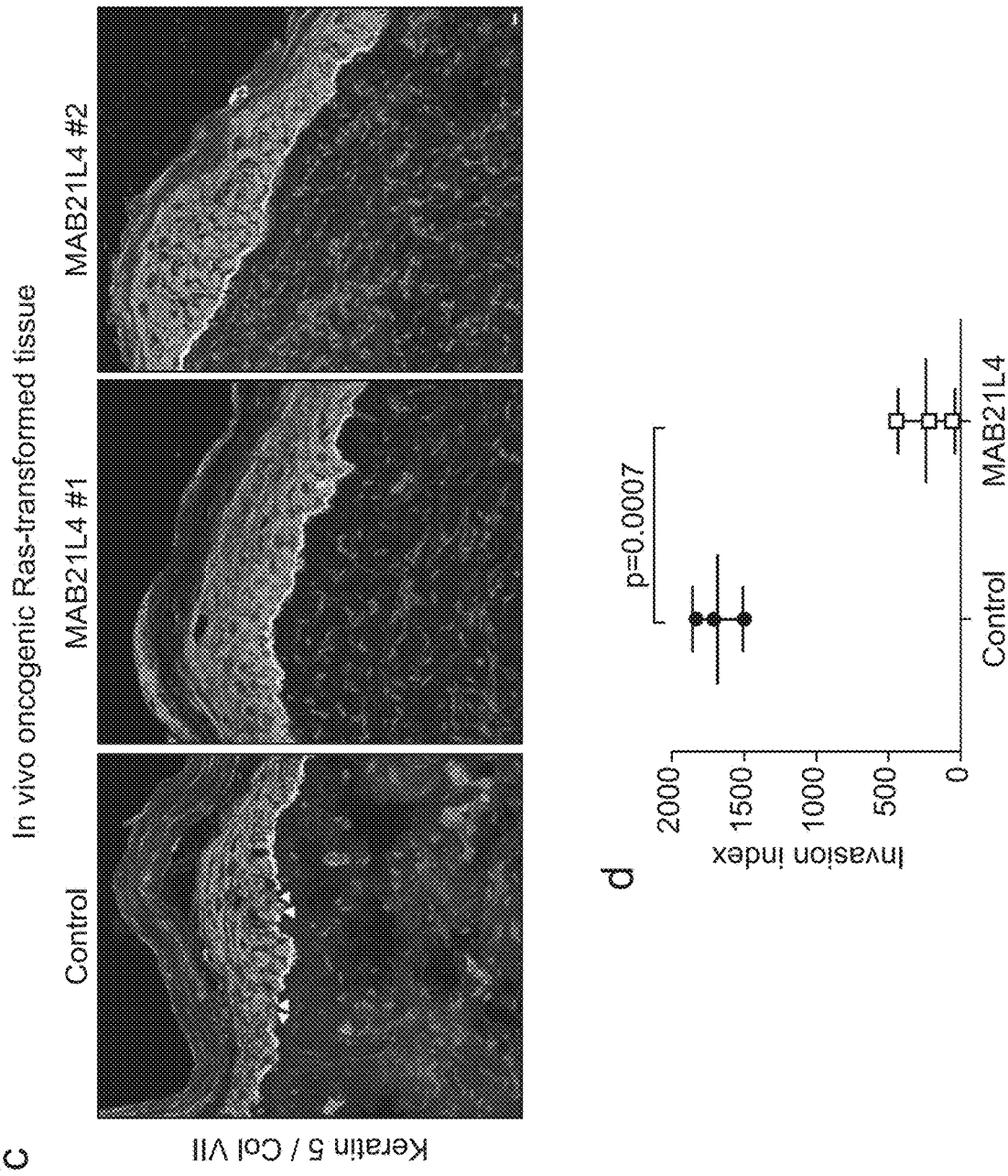

C

Human skin xenografts

Oncogenic Ras- transformed tissue

DIAGNOSIS AND REGULATION OF EPIDERMAL DIFFERENTIATION AND CANCER CELL ACTIVITY

BACKGROUND

Cutaneous squamous cell carcinoma (SCC) is the second most common cancer, with approximately one million cases treated in the United States each year[1]. While surgical management of small SCC is often curative, PD-1 blockade with cemiplimab represents the sole targeted therapy approved by the Food and Drug Administration for treatment of advanced SCC. Despite the pressing clinical need for additional targeted agents to treat SCC, particularly those that might be effective against early lesions, the development of new therapeutic strategies appears to be lagging. The most common genetic alterations in SCC are not necessarily actionable; somatic mutations in canonical tumor suppressor genes, such as TP53, 2 CDNK2A, and FAT1, occur at high frequencies in SCC, while recurrent tumor-promoting mutations are relatively rare events and include single nucleotide substitutions in HRAS and KNSTRN. Genes implicated in epidermal differentiation, such as NOTCH1/2, CASP8, PARD3, and RIPK4, are also often mutationally inactivated in SCC, highlighting the potential importance of their function in this setting.

Like many other cancers, loss of differentiation in SCC predicts tumor recurrence, metastasis, and worse overall survival. Analyses of human SCC bolstered by studies in mice indicate that aberrant expression of proteins controlling skin differentiation contributes functionally to tumorigenesis. Increased expression of cyclin D1 is frequently observed in SCC and transgenic mice with enforced skin-specific expression of cyclin D1 are more susceptible to DMBA carcinogenesis. Primary keratinocytes cultured from these mice are notably resistant to calcium-induced differentiation, suggesting that a failure to differentiate might underlie carcinogen susceptibility and supporting reports of decreased cyclin D1 expression in keratinocytes that are irreversibly committed to terminal differentiation. Similarly, moderate overexpression of ΔNp63α, the p63 isoform primarily responsible for regulating epidermal proliferation and differentiation, is detected in human SCC and also enhances DMBA carcinogenesis when expressed in transgenic mice. By contrast, loricrin, the major structural component of the epidermal cornified cell envelope, is down-regulated in SCC and mice deficient in loricrin are prone to ultraviolet-induced skin injury and DNA damage. Deregulated expression of epidermal differentiation mediators in SCC thus appears to create conditions that are permissive for tumorigenesis, although the full suite of affected genes and the nature of their functional roles have not been fully defined.

The compositions and methods described herein are directed towards identifying agents that can detect and modulate proteins associated with SCC tumorigenesis

SUMMARY

Compositions and methods are provided for the diagnosis and treatment of skin cancers and squamous cell carcinomas, including e.g. and without limitation, squamous cell carcinoma (SCC) and basal cell carcinoma. In some embodiments the cancer is advanced cutaneous squamous cell carcinoma.

MAB21L4 is a previously uncharacterized protein, also referred to as "C2orf54" that is shown herein to control skin differentiation and to function as a tumor suppressor in skin cancer, including cutaneous squamous cell carcinoma (SCC). Expression of MAB21L4 is upregulated in differentiation of human keratinocytes and is profoundly down-regulated in SCC compared to patient-matched normal skin. MAB21L4 protein is necessary as well as sufficient for epidermal differentiation and reduces invasiveness in an in vivo model of human SCC.

Demonstrated herein is a tumor suppressive role for MAB21L4 that involves RET inhibition, and identifies RET as a therapeutic target in SCC. RET is shown to regulate epidermal differentiation, as well as the development of keratinocyte cancers. In some embodiments a therapeutic use of selective RET inhibitors and/or MAB21L4 mimics in skin cancers is provided. These and related compounds, particularly those that can be delivered to the skin topically, are a valuable addition to existing treatment options for skin cancer, including SCC and its precursor lesions.

In some embodiments a method is provided for treatment of skin cancers and squamous cell carcinomas. In some embodiments the cancer is a cutaneous squamous cell carcinoma. In some embodiments a method is provided for preventive treatment of pre-cancerous epidermal lesions, e.g. actinic keratosis. In such embodiments, the cancer or pre-cancer is contacted with a therapeutically effective dose of a RET pathway inhibitor. The RET inhibitor may inhibit RET directly; or may mimic the activity MAB21L4 and thereby inhibit RET. In some embodiments the RET inhibitor is a selective RET inhibitor, including without limitation pralsetinib or selpercatinib. The contacting may be topical. The treatment can reduce cancer development and progression; and can reduce metastasis and invasion, including perineural invasion.

In other embodiments a method is provided for the treatment of skin cancers and squamous cell carcinomas or pre-cancers by contacting with a therapeutically effective dose of a MAB21L4 mimic.

In some embodiments, prior to treatment the cancer is analyzed for reduced expression of MAB21L4, relative to a normal sample. A reduction or loss of MAB21L4 is indicative that there is a lack of RET regulation, and the individual may be selected for treatment with a RET inhibitor and/or MAB21L4 mimic. The contacting of a cancer cells may be performed in vivo, e.g. for therapeutic purposes, and in vitro, e.g. for screening assays and the like.

Treatment of a patient diagnosed with SCC with the compositions described herein can be combined with other medical means for treating SCC, such as surgery, radiotherapy, and chemotherapy. In some embodiments therapy is combined with one or more additional anti-cancer treatments. Where a combination of agents is provided, the agents can be administered concomitantly, i.e. each agent is administered within about 45 days, 30 days, 15 days, 7 days, 3 days, 2 days, 1 day or substantially simultaneously with respect to the other agent(s) in the combination. The agents can be considered to be combined if administration scheduling is such that the both agents are at a therapeutic level in the individual for at least overlapping periods of time. A benefit can be the use of lowered doses of one or more of the agents relative to the dose required as a monotherapy; and or a synergistic therapeutic effect. Further, the combination can provide for increased overall survival of the individual that is treated. Administration may be repeated as necessary for depletion of the cancer cell population.

SCC can be selected from the group consisting of skin cancer, lung cancer, head cancer, gastric cancer, colorectal cancer, throat cancer, cancer of the urinary tract, cancer of the reproductive tract, esophageal cancer, and bronchiogenic carcinoma. In some embodiment the cancer is cutaneous squamous cell carcinoma or a precancer thereof, e.g. actinic keratosis.

These and other features of the compositions and methods described herein will become more apparent from the detailed description below.

BRIEF DESCRIPTION OF THE DRAWINGS

Aspects of the invention can be more fully understood with respect to the following drawings. In the drawings, similar elements are referenced with like numbers.

DETAILED DESCRIPTION

Figure 1:
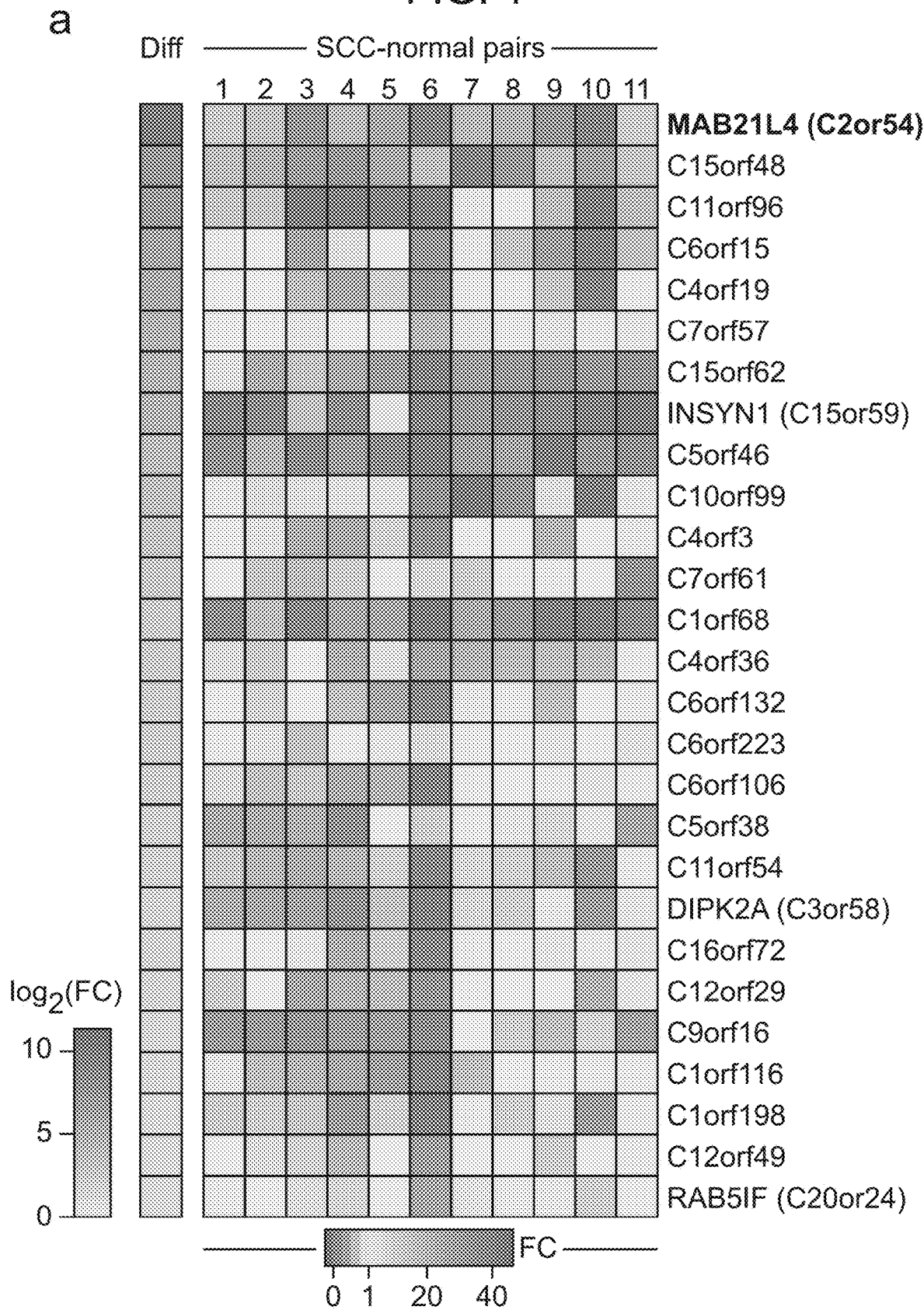
FIG. 1. Expression of MAB21L4 in epidermal differentiation and cancer (a) RNA-seq heatmap of uncharacterized ORFs upregulated in primary human keratinocytes after 6 days of calcium-induced differentiation compared to undifferentiated, sub-confluent keratinocytes as control. 11 primary human SCC with individual-matched normal skin as control were analyzed by RNA-seq and the expression fold change for each ORF is shown. FC, fold change. (b) MAB21L4 transcript induction during keratinocyte differentiation by quantitative qRT-PCR; undifferentiated cells (day 0) and days 3 and 6 of calcium-induced differentiation. Data shown are representative of n=3 independent experiments. Bars represent mean±SD, three technical replicates per experiment. (c) MAB21L4 protein induction over 6 days of calcium-induced differentiation in primary keratinocytes. Data shown are representative of n=3 biological replicates. (d) Expression of MAB21L4 in normal human adult skin. The dotted white line demarcates the basal layer from the suprabasal layers and collagen VII (green) decorates the basement membrane zone. Scale bar, 10 µm. (e) Gene Ontology terms of genes with low expression when MAB21L4 expression is low using publicly available microarray data (p-values were adjusted using the Benjamini-Hochberg procedure with FDR of 0.05). (f) Quantification of MAB21L4 expression in normal skin, pre-cancerous actinic keratoses (AK), and cutaneous squamous cell carcinoma (SCC). (g) Somatic MAB21L4 deletion in individual cancer types. Somatic deletion segments that do not span known tumor suppressor genes are shown in red. GISTIC-identified peak regions are shown in green. The position of the MAB21L4 locus is shown in pink.
Figure 1:
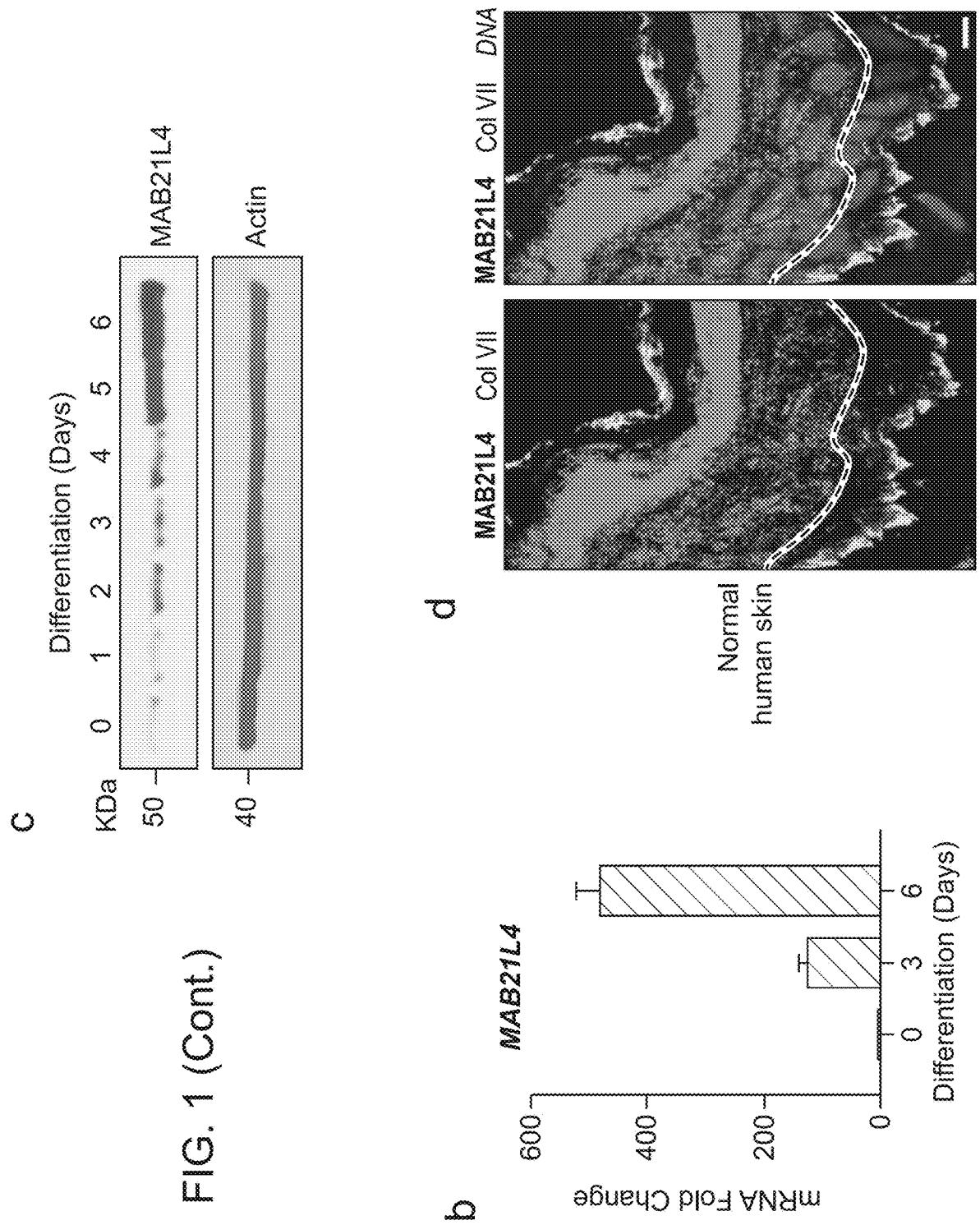
Figure 1:
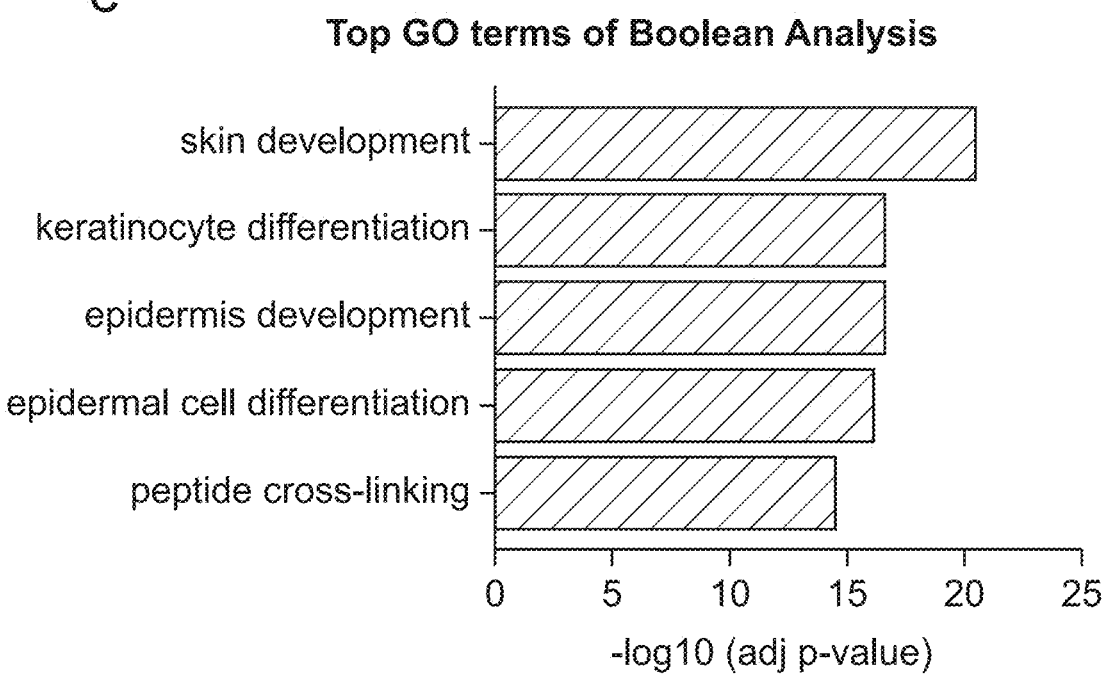
Figure 1:
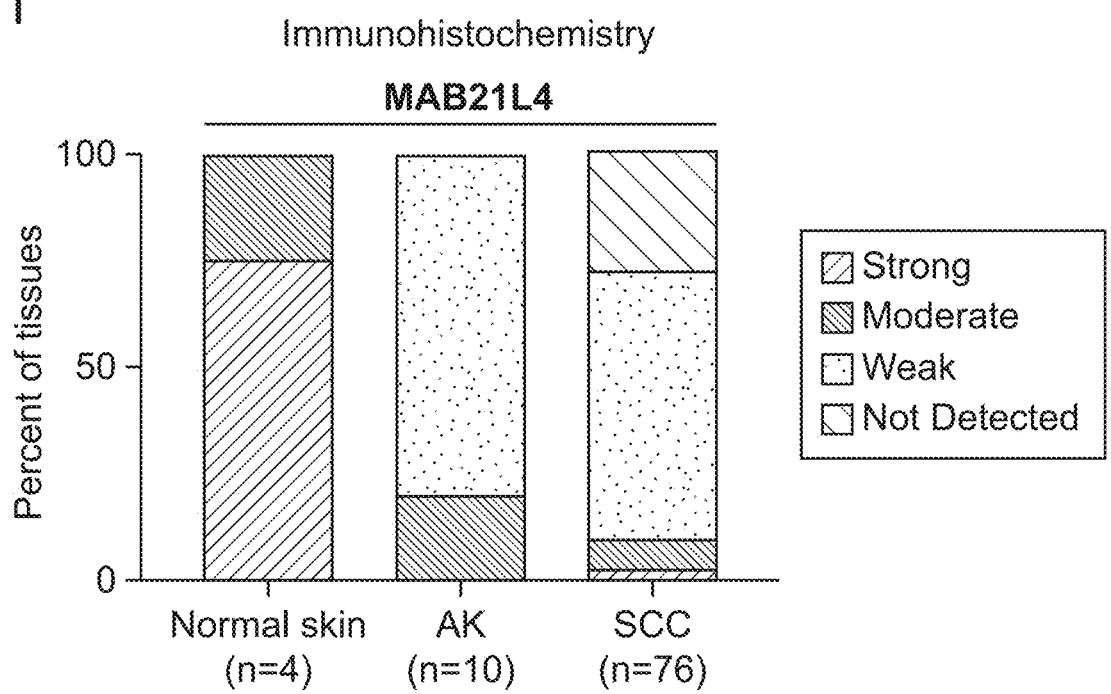
Figure 1:
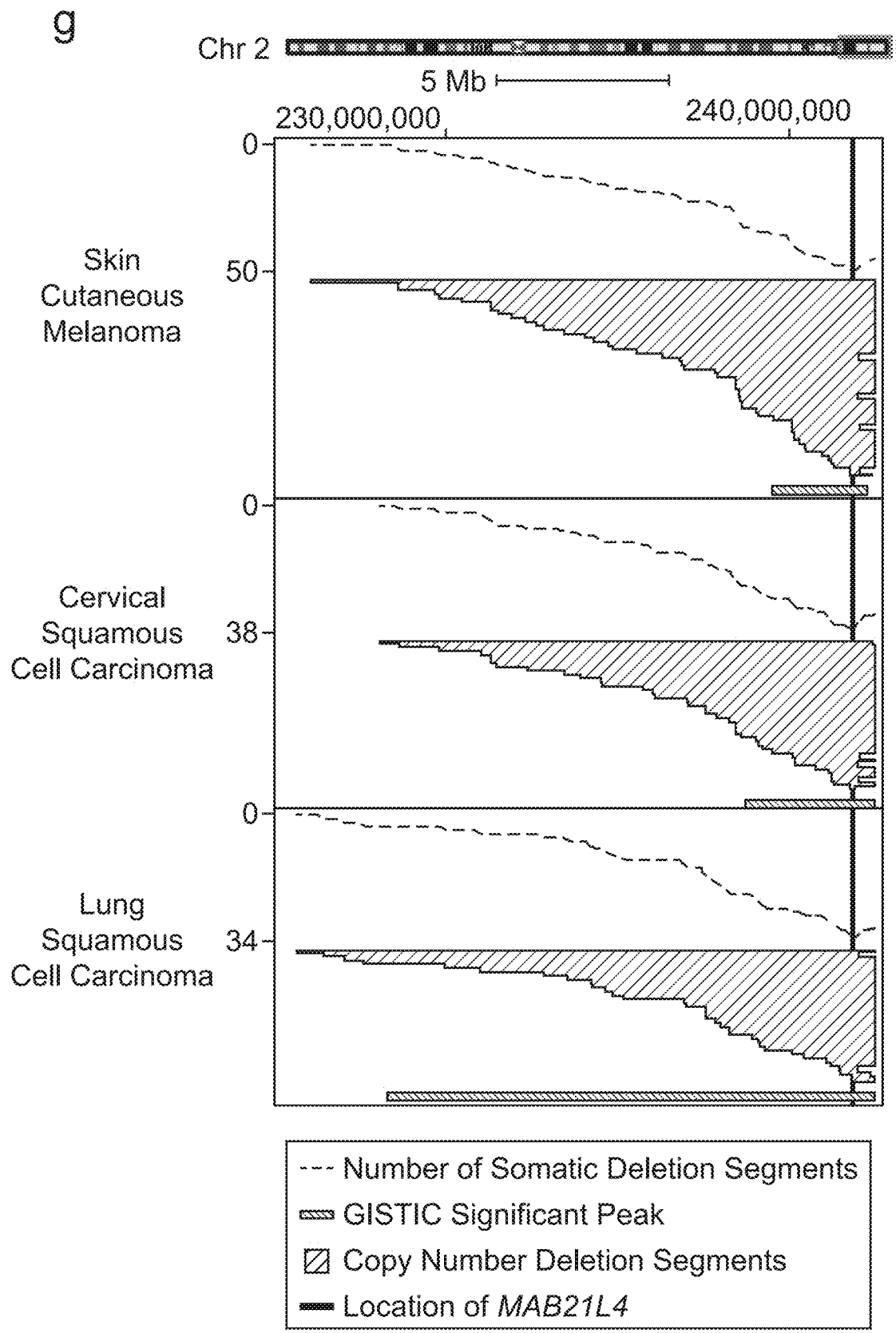

It is shown herein that reduction or loss of MAB21L4 polynucleotide and amino acid sequences are associated with skin cancer. Loss or reduced expression of MAB21L4 leads to overexpression of wild type RET and epidermal cancer development. It is believed that MAB21L4-CacyBP interaction is required for RET ubiquitination by Siah1, which targets RET for proteasome-mediated degradation. Loss of MAB21L4 stabilizes RET by preventing its Siah1-mediated degradation, resulting in RET upregulation.

RET maintains keratinocytes in an undifferentiated state; normal differentiation requires endogenous levels of RET and can be enhanced by reducing RET expression intrinsically below wild type levels. Loss of differentiation is coupled to cancer-enabling behaviors. Inhibition of RET signaling in epidermal cancer reduces cancer development and progression; and can reduce metastasis and invasion, including perineural invasion.

Diagnostic methods; therapeutic methods, and screening methods are provided relating to this newly identified tumor suppressor protein and its interaction with RET.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise.

Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Definitions

Biological sample. The term "sample" with respect to an individual encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations, such as cancer cells. The definition also includes samples that have been enriched for particular types of molecules, e.g., nucleic acids, polypeptides, etc.

DNA samples, e.g. samples useful in genotyping, are readily obtained from any nucleated cells of an individual, e.g. hair follicles, cheek swabs, white blood cells, etc., as known in the art.

The term "biological sample" encompasses a clinical sample. The types of "biological samples" include, but are not limited to: tissue obtained by surgical resection, tissue obtained by biopsy, cells in culture, cell supernatants, cell lysates, tissue samples, organs, bone marrow, blood, plasma, serum, fine needle aspirate, lymph node aspirate, cystic aspirate, a paracentesis sample, a thoracentesis sample, and the like.

Obtaining and assaying a sample. The term "assaying" is used herein to include the physical steps of manipulating a biological sample to generate data related to the sample. As will be readily understood by one of ordinary skill in the art, a biological sample must be "obtained" prior to assaying the sample. Thus, the term "assaying" implies that the sample has been obtained. The terms "obtained" or "obtaining" as used herein encompass the act of receiving an extracted or isolated biological sample. For example, a testing facility can "obtain" a biological sample in the mail (or via delivery, etc.) prior to assaying the sample. In some such cases, the biological sample was "extracted" or "isolated" from an individual by another party prior to mailing (i.e., delivery, transfer, etc.), and then "obtained" by the testing facility upon arrival of the sample. Thus, a testing facility can obtain the sample and then assay the sample, thereby producing data related to the sample.

The terms "obtained" or "obtaining" as used herein can also include the physical extraction or isolation of a biological sample from a subject. Accordingly, a biological sample can be isolated from a subject (and thus "obtained") by the same person or same entity that subsequently assays the sample. When a biological sample is "extracted" or "isolated" from a first party or entity and then transferred (e.g., delivered, mailed, etc.) to a second party, the sample was "obtained" by the first party (and also "isolated" by the first party), and then subsequently "obtained" (but not "isolated") by the second party. Accordingly, in some embodiments, the step of obtaining does not comprise the step of isolating a biological sample.

In some embodiments, the step of obtaining comprises the step of isolating a biological sample (e.g., a pre-treatment biological sample, a post-treatment biological sample, etc.). Methods and protocols for isolating various biological samples (e.g., a blood sample, a serum sample, a plasma sample, a biopsy sample, an aspirate, etc.) will be known to one of ordinary skill in the art and any convenient method may be used to isolate a biological sample.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assaying may be relative or absolute. For example, "assaying" can be determining whether the expression level is less than or "greater than or equal to" a particular threshold, (the threshold can be pre-determined or can be determined by assaying a control sample). On the other hand, "assaying to determine the expression level" can mean determining a quantitative value (using any convenient metric) that represents the level of expression (i.e., expression level, e.g., the amount of protein and/or RNA, e.g., mRNA).

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human. The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The term "diagnosis" is used herein to refer to the identification of a molecular or pathological state, disease or condition, such as the identification of a molecular subtype of cancer, or identification of a cancer suitable for treatment by RET inhibition.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

"Concomitant administration" of a cancer therapeutic drug, tumor-directed antibody, etc. with a pharmaceutical composition of the present invention means administration at such time that both the drugs will have a therapeutic effect. Such concomitant administration may involve concurrent (i.e. at the same time), prior, or subsequent administration with respect to the administration of a compound of the invention. A person of ordinary skill in the art would have no difficulty determining the appropriate timing, sequence and dosages of administration for particular drugs and compositions of the present invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

A "therapeutically effective dose" or "therapeutic dose" is an amount sufficient to effect desired clinical results (i.e., achieve therapeutic efficacy). For purposes of this invention, a therapeutically effective dose of an agent is an amount that is sufficient to palliate, ameliorate, stabilize, reverse, prevent, slow or delay the progression of the disease state.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

"Cancer" has its standard meaning and is intended to refer to any malignant tumor of potentially unlimited growth that expands locally by proliferation and systemically by metastasis. "Neoplasm" has its standard meaning and is intended to refer to the abnormal growth of a tissue, such as a tumor. "Tumorigenesis" has its standard meaning and is intended to refer to the basic developmental processes that produce tumors. These basic properties include the ability to proliferate or invade nearby normal cells and the ability to migrate from the site where the tumor initiated, i.e. metastasis.

Skin cancer is the most common type of cancer and commonly develops in sun-exposed areas of skin. Basal and squamous cell skin cancers are the most common types of skin cancer. They start in the top layer of skin, the epidermis, and may be referred to as epidermal cancers. The incidence is highest among outdoor workers, sportsmen, and sunbathers and is inversely related to the amount of melanin skin pigmentation; fair-skinned people are most susceptible. Skin cancers may also develop years after therapeutic x-rays or exposure to carcinogens. Over 5.4 million new cases of skin cancer are diagnosed in over 3.3 million people in the United States yearly. The most common forms of skin cancer are basal cell carcinoma; squamous cell carcinoma, and melanoma. Less common forms of skin cancer are Paget disease of the nipple or extramammary Paget, Kaposi sarcoma, Merkel cell carcinoma, atypical fibroxanthomas, tumors of the adnexa, cutaneous T-cell lymphoma (mycosis fungoides). Bowen disease is a superficial squamous cell carcinoma. Keratoacanthoma may be a well-differentiated form of squamous cell carcinoma. Initially, skin cancers are often asymptomatic. The most frequent presentation is an irregular red or pigmented lesion that does not go away. If treated early, most skin cancers are curable.

Cutaneous squamous cell carcinoma is a malignant tumor of epidermal keratinocytes that invades the dermis; this cancer usually occurs in sun-exposed areas. Local destruction may be extensive, and metastases occur in advanced stages. Diagnosis is by biopsy. Treatment depends on the tumor's characteristics and may involve curettage and electrodesiccation, surgical excision, cryosurgery, or, occasionally, radiation therapy. Squamous cell carcinoma is the 2nd most common type of skin cancer after basal cell carcinoma, with >1 million cases annually in the United States, and 2500 deaths. It may develop in normal tissue, in a preexisting actinic keratosis, in a patch of oral leukoplakia, or in a burn scar.

The clinical appearance is highly variable, but any non-healing lesion on sun-exposed surfaces should be suspect. The tumor may begin as a red papule or plaque with a scaly or crusted surface and may become nodular or hyperkeratotic, sometimes with a warty surface. In some cases, the bulk of the lesion may lie below the level of the surrounding skin. Eventually the tumor ulcerates and invades the underlying tissue.

Regional and distant metastases of squamous cell carcinomas on sun-exposed skin are uncommon but do occur, particularly with poorly differentiated tumors. Characteristics of more aggressive tumors include size>2 cm in diameter, invasion depth of>2 mm, perineural invasion, and location near the ear or vermilion border. About one third of lingual or mucosal cancers have metastasized before diagnosis.

Late-stage disease, which may require extensive surgery, is far more likely to metastasize. It spreads initially regionally to surrounding skin and lymph nodes and eventually to nearby organs. Cancers that occur near the ears or the vermilion border, in scars, or that have perineural invasion are more likely to metastasize. The overall 5-year survival rate for metastatic disease is 34% despite therapy.

Conventional treatment of squamous cell carcinoma includes curettage and electrodesiccation, surgical excision, cryosurgery, topical chemotherapy (imiquimod or 5-fluorouracil) and photodynamic therapy, or, occasionally, radiation therapy. Treatment and follow-up must be monitored closely because of the risk of metastasis.

Actinic keratoses are precancerous changes in skin cells (keratinocytes) that are a frequent, consequence of many years of sun exposure. People with blonde or red hair, blue eyes, and skin type I or II are particularly susceptible. Actinic keratoses are usually pink or red, poorly marginated, and feel rough and scaly on palpation, although some are light gray or pigmented, giving them a brown appearance.

Basal cell carcinoma is the most common type of skin cancer, with >4 million new cases yearly in the United States. It is most common among fair-skinned people with a history of sun exposure and is very rare in darkly pigmented people. Basal cell carcinomas are also associated with genetic syndromes and may arise in a nevus sebaceous. *Xeroderma pigmentosum* represents an inherited defect in DNA repair that can result in nonmelanoma skin cancer and in melanoma. Basal cell nevus syndrome (Gorlin syndrome) is an autosomal dominant disorder that results in multiple basal cell carcinomas as well as in medulloblastomas, meningiomas, breast cancers, non-Hodgkin lymphomas, and ovarian cancers. Bazex syndrome is a rare genodermatosis that can result in the early onset of multiple basal cell carcinomas.

The clinical manifestations and biologic behavior of basal cell carcinomas are highly variable. The most common types are nodular: small, shiny, firm, almost translucent to pink nodules with telangiectases, usually on the face Superficial are red or pink, marginated, thin papules or plaques, commonly on the trunk, that are difficult to differentiate from psoriasis or localized dermatitis. Morpheaform are flat, scarlike, indurated plaques that can be flesh-colored or light red and have vague borders. Nodular and superficial basal cell carcinomas can produce pigment (sometimes called pigmented basal cell carcinomas).

The clinical appearance, size, site, and histologic subtype determine choice of treatment—curettage and electrodesiccation, surgical excision, cryosurgery, topical chemotherapy (imiquimod or 5-fluorouracil) and photodynamic therapy, or, occasionally, radiation therapy. Recurrent or incompletely treated cancers, large cancers, cancers at recurrence-prone sites (eg, head and neck), and morphea-like cancers with vague borders are often treated with Mohs microscopically controlled surgery, in which tissue borders are progressively excised until specimens are tumor-free (as determined by microscopic examination during surgery).

If patients have metastatic or locally advanced disease and are not candidates for surgery or radiation therapy, vismodegib and sonidegib may be given. Both drugs inhibit the hedgehog pathway.

"Squamous cell carcinoma" has its standard meaning and is intended to refer to any neoplasm or tumor of epithelial cells.

Association in this context means that the amino acid and polynucleotide sequences are either differentially expressed or altered in SCCs or neoplastic epithelial cells as compared to normal epithelial tissue. "SCC" refers herein to any malignant neoplasm or tumor of epithelial cells. Specific examples of epithelial cells include squamous cells, squamous carcinoma cells, keratinocytes, mucosal epithelial cells, such as oral mucosal cells, gastrointestinal epithelial cells, corneal epithelium of the eye, and epithelial cells of the urinary and reproductive tract. Specific examples of SCC carcinomas arising from neoplastic epithelial cells include skin, lung, head, neck, oral, gastric, colorectal, throat, urinary tract, reproductive tract, esophageal, etc.

SCC is commonly sun-induced, i.e., actinically derived SCC. SCC can also result from transplant or invasive surgery, or follow other immunosuppressive situations. Chronic inflammation can lead to development of SCC at the site of inflammation, e.g., a burn or scar, Majolin's ulcer, etc. SCC can be virally induced, for example, SCC can result from human papillomavirus-induced (HPV) infection. SCC can include adenoid (acantholytic) SCC, spindle cell SCC, verrucous carcinoma (VC), keratoacanthoma (KA), nodular SCC periungual SCC, and other epithelial carcinomas.

Mab21L4. Chromosome 2 open reading frame 54, otherwise known as Mab21L4, is a protein that in humans is encoded by the C2orf54 gene. Prior to the present disclosure, the activity of the encoded protein was not known. Sequences of the human protein and gene may be found at Genbank, RefSeq (mRNA): NM_001085437; NM_001282921; NM_024861 and RefSeq (protein): NP_001078906; NP_001269850; NP_079137.

RET. The RET proto-oncogene encodes a receptor tyrosine kinase for members of the glial cell line-derived neurotrophic factor (GDNF) family ligands (GFL). RET loss of function mutations are associated with the development of Hirschsprung's disease, while gain of function mutations are associated with the development of various types of human cancer, including medullary thyroid carcinoma, multiple endocrine neoplasias type 2A and 2B, pheochromocytoma and parathyroid hyperplasia.

The human gene RET is localized to chromosome 10 (10q11.2) and contains 21 exons. The natural alternative splicing of the RET gene results in the production of 3 different isoforms of the protein RET. RET51, RET43 and RET9 contain 51, 43 and 9 amino acids in their C-terminal tail respectively. The biological roles of isoforms RET51 and RET9 are the most common isoforms. Common to each isoform is a domain structure. Each protein is divided into three domains: an N-terminal extracellular domain with four cadherin-like repeats and a cysteine-rich region, a hydrophobic transmembrane domain and a cytoplasmic tyrosine kinase domain, which is split by an insertion of 27 amino acids. Within the cytoplasmic tyrosine kinase domain, there are 16 tyrosines (Tyrs) in RET9 and 18 in RET51. Tyr1090 and Tyr1096 are present only in the RET51 isoform. The extracellular domain of RET contains nine N-glycosylation sites.

In order to activate RET, GFLs form a complex with a glycosylphosphatidylinositol (GPI)-anchored co-receptor. The co-receptors themselves are classified as members of the GDNF receptor-α (GFRα) protein family. Different members of the GFRα family (GFRα1, GFRα2, GFRα3, GFRα4) exhibit a specific binding activity for a specific GFLs. Upon GFL-GFRα complex formation, the complex then brings together two molecules of RET, triggering trans-autophosphorylation of specific tyrosine residues within the tyrosine kinase domain of each RET molecule. Tyr900 and Tyr905 within the activation loop (A-loop) of the kinase domain have been shown to be autophosphorylation sites. Phosphorylation of Tyr905 stabilizes the active conformation of the kinase, which, in turn, results in the autophosphorylation of other tyrosine residues mainly located in the C-terminal tail region of the molecule. Phosphorylation of Tyr981 and the additional tyrosines Tyr1015, Tyr1062 and Tyr1096 have been shown to be important to the initiation of intracellular signal transduction processes.

METHODS

Methods are provided for treatment of skin cancers and squamous cell carcinomas. In some embodiments the cancer is a cutaneous squamous cell carcinoma. In some embodiments a method is provided for preventive treatment of pre-cancerous epidermal lesions, e.g. actinic keratosis. In such embodiments, the cancer or pre-cancer is contacted with a therapeutically effective dose of a RET inhibitor, which may be a selective RET inhibitor, or a multi-kinase inhibitor. The treatment can reduce cancer development and progression; and can reduce metastasis and invasion, including perineural invasion.

Oncogenic RET fusions and activating germline or somatic RET mutations are known to be drivers of certain cancers. The findings of the present disclosure demonstrate that a loss of MAB21L4 can also result in inappropriate RET activity, and increased invasiveness in skin cancers. RET inhibitors are therefore useful in the treatment of skin cancers and squamous cell carcinomas, particularly cutaneous SCC. In some embodiments the cancer is characterized by a loss of MAB21L4 activity.

For example, selective RET inhibitors include BLU-667 (pralsetinib), which targets cancer cells with activating RET mutations as well as fusions and has demonstrated clinical activity in RET-altered solid tumors (see clinical trial NCT03037385). Pralsetinib is shown herein to be active against RET in skin cancers, e.g. cancer characterized by a loss of MAB21L4 activity. LOXO-292 (Selpercatinib) selectively targets RET and has activity against activating RET fusions/mutations, potential resistance mutations, and brain metastases (see clinical trial NCT03157128).

A number of approved multi-kinase inhibitors (mKIs) have in vitro activity against wild-type (WT) RET, including for example cabozantinib, vandetanib, and lenvatinib, which have been repurposed for treating RET-driven diseases. The pyrazolopyrimidines PP1 and PP2 and the 4-anilinoquinazoline ZD6474 display a strong inhibitory activity (IC50≤100 nM) towards active oncogenic RET kinases (Carlomagno, et al. (2004) Oncogene 23: 6056-6063). SU5416 is a 3-substituted indolin-2-one compound that blocks RET kinase activity.

In some embodiments, prior to treatment the cancer is analyzed for reduced expression of MAB21L4, relative to a normal sample. A reduction or loss of MAB21L4 is indicative that there is a lack of RET regulation, and the individual may be selected for treatment with a RET inhibitor and/or MAB21L4 mimic.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip.™. expression arrays, Lockhart, Nature Biotechnology, 14:1675-1680 (1996), hereby expressly incorporated by reference. Other techniques include, but are not limited to, quantitative reverse transcriptase PCR, Northern analysis and RNase protection. As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored.

MAB21L4 expression coincides with engagement of the terminal differentiation gene expression program in the skin. Reduced expression of MAB21L4 is found in SCC as well as actinic keratoses (AK), the earliest clinically detectable SCC precursors. Reduction in expression relative to a normal control can be analyzed at the mRNA level or the protein level. The reduction may be at least about 25%, at least about 50%, at least about 75%, and may be reduced 1-fold, 2-fold, 3-fold, 4-fold or more. In some embodiments, somatic loss of MAB21L4 is analyzed, for the absence of one or both MAB21L4 alleles in a cancer sample. MAB21L4 is found to be deleted across all tumor types in 18.8% and places it in a focal peak of deletion in 21 Cancer Genome Atlas (TCGA) cancer types, including cervical SCC and cutaneous melanoma. Loss or reduced expression of MAB21L4 is tumor promoting. Specifically MAB21L4 is shown to suppress Ras-driven invasion in human skin tissue, and effectively blocks neoplastic progression in vivo.

In other embodiments, bioactive agents having a desired pharmacological activity are identified as mimicking the activity of MAB21L4. Examination of 10,844 tumor-normal pairs from The Cancer Genome Atlas (TCGA) consortium reveals deletion of the MAB21L4 locus in 21 common cancer types, where it is frequently associated with reduced survival.

The disclosure herein on MAB21L4 role in skin differentiation and early tumor progression demonstrate that its dependent pathways can provide novel therapeutic targets in SCC. In a drug-repositioning screen with the MAB21L4 gene signature, existing drugs predicted to mimic its function were identified. This analysis highlighted several drugs that target key cancer mechanisms, including HDAC inhibitors, mTOR inhibitors, and PI3K inhibitors, and provide therapeutic candidates for treatment of SCC, particularly where MAB21L4 expression is reduced. These candidates are validated for tumor-suppressing effects in a mouse model of human SCC, with a particular focus on FDA-approved agents to bypass the time and cost required to bring a new drug to market.

Also provided are methods of treating SCC by administering an effective dose of an agent identified as a mimic of MAB21L4. Mimics include, without limitation:

| | | |
|---|---|---|
| PAC-1 | Procaspase-3 activator | Approved |
| Mocetinostat | HDAC inhibtor | Approved |
| BI-2536 | PLK inhibitor | Investigational |
| A443654 | AKT inhibitor | Not Approved |
| Rottlerin | PKC inhibitor | Not Approved |
| GF 109203X | PKC inhibitor | Not Approved |
| ISOX | HDAC inhibtor | Not Approved |
| Doxorubicin | Topoisomerase inhibitor | Approved |
| YM-201636 | PIKfyve inhibitor | Not Approved |
| CGP-60474 | Cdk1/2 inhibitor | Not Approved |
| Torin 1 | mTOR inhibitor | Not Approved |
| NVP-TAE684 | ALK inhibitor | Not Approved |
| BMS-345541 | IKK inhibitor | Not Approved |
| Vorinostat | HDAC inhibtor | Approved |
| JAK3 Inhibitor VI | JAK inhibitor | Not Approved |
| Trichostatin A | HDAC inhibtor | Not Approved |
| Wortmannin | PI3K inhibitor | Not Approved |
| Ingenol 3, 20-dibenzoate | PKC agonist | Not Approved |
| Chaetocin | Histone methyltransferase inhibitor | Not Approved |
| AZD8055 | mTOR inhibitor | Investigational |
| PLX-4720 | BRAF inhibitor | Not Approved |

RET inhibitors or MAB21L4 mimics agents can be delivered directly or in pharmaceutical compositions along with suitable carriers or excipients, as well known in the art. Present methods of treatment include embodiments providing for administration of an effective amount of such a compound to a patient in need of treatment.

An effective amount of such agents can readily be determined by routine experimentation, as can the most effective and convenient route of administration and the most appropriate formulation. Various formulations and drug delivery systems are available in the art. (See, e.g., Remington's Pharmaceutical Sciences, supra.)

Topical administration is of particular interest. Others-Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot, microneedle, or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Dosage amount and interval may be adjusted individually to provide tissue levels of the active moiety which are sufficient to affect the expression or activity of RET, as desired, i.e. minimal effective concentration (MEC). The MEC will vary for each agent but can be estimated from, for example, in vitro data, such as the concentration necessary to achieve 50-90% inhibition of MFP activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as squamous cell carcinoma or other cancers and conditions associated with altered expression of RET.

In some embodiments, the therapeutic dosage of a RET inhibitor may range from about 0.0001 to 100 mg/cm$^2$, and more usually 0.01 to 5 mg/cm$^2$, of the skin lesion. For example dosages can be about 0.1; 0.5; 1; 5; 10; 25; 50; 75; 100; 250; 500; 750; 1000 or more mg administered directly to a lesion or systemically, e.g. orally, administered. An exemplary treatment regime entails administration daily, twice dialed, every other day; every 3 days; weekly; once every two weeks; once a month, etc. Therapeutic entities can be administered on multiple occasions. Intervals between single dosages can be weekly, monthly or yearly. Intervals can also be irregular as indicated by measuring levels of the therapeutic entity in the patient. Alternatively, therapeutic entities of the present invention can be administered as a sustained release formulation, in which case less frequent administration is required. Dosage and frequency vary depending on the half-life of the drug in the patient.

In prophylactic applications, e.g. treatment of pre-malignant or pre-cancerous lesions, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cutaneous SCC. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50.

Dosages preferably fall within a range of circulating concentrations that includes the ED50 with little or no toxicity. Dosages may vary within this range depending upon the dosage form employed and the route of administration utilized. The exact formulation, route of administration, and dosage should be chosen, according to methods known in the art, in view of the specifics of a subject's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the compositions and instructions for use, for example reagents for determining expression of MAB21L4; and an inhibitor of RET. The kit can further contain a least one additional reagent, e.g. a chemotherapeutic drug, etc. Kits typically include a label indicating the intended use of the contents of the kit. The term label includes any writing, or recorded material supplied on or with the kit, or which otherwise accompanies the kit.

In some embodiments, a method is provided to evaluate the effect of a candidate drug on a squamous cell carcinoma. In some embodiments a SCC is contacted with candidate drug. A number of different assays can be used to evaluate the effect of the candidate drug. For example, the expression profile of the cell sample can be determined and compared with an expression profile of a healthy individual. In some embodiments, the cell sample can be analyzed for the presence or absence of MAB21L4 associated with SCC development before and after treatment with a candidate drug. In yet other embodiments, the size of the tumor before and after treatment with a candidate drug can be analyzed to determine if the drug is effective in inhibiting the invasion of nearby normal cells.

In screening assays for the small molecules, the effect of adding a candidate agent to cells in culture is tested with a panel of cells and cellular environments, where the cellular environment includes one or more of: electrical stimulation including alterations in ionicity, drug stimulation, and the like, and where panels of cells may vary in genotype, in prior exposure to an environment of interest, in the dose of agent that is provided, etc., where usually at least one control is included, for example a negative control and a positive control. Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free. The effect of the altering of the environment is assessed by monitoring multiple output parameters, including morphogical, functional and genetic changes.

In the screening assays for genetic agents, polynucleotides are added to one or more of the cells in a panel in order to alter the genetic composition of the cell. The output parameters are monitored to determine whether there is a change in phenotype. In this way, genetic sequences are identified that encode or affect expression of proteins in pathways of interest. The results can be entered into a data processor to provide a screening results dataset. Algorithms are used for the comparison and analysis of screening results obtained under different conditions.

Parameters are quantifiable components of cells, particularly components that can be accurately measured, desirably in a high throughput system. A parameter can also be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Variability is expected and a range of values for each of the set of test parameters will be obtained using standard statistical methods with a common statistical method used to provide single values.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide. A parameter may be defined by a specific monoclonal antibody or a ligand or receptor binding determinant.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Cardiovascular Drugs; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:I to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As used herein, the term "genetic agent" refers to polynucleotides and analogs thereof, which agents are tested in the screening assays of the invention by addition of the genetic agent to a cell. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Introduction of an expression vector encoding a polypeptide can be used to express the encoded product in cells lacking the sequence, or to over-express the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode an anti-sense sequence; be an antisense oligonucleotide; RNAi, encode a dominant negative mutation, or dominant or constitutively active mutations of native sequences; altered regulatory sequences, etc.

Antisense and RNAi oligonucleotides can be chemically synthesized by methods known in the art. Preferred oligonucleotides are chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity, e.g. morpholino oligonucleotide analogs. The □-anomer of deoxyribose may be used, where the base is inverted with respect to the natural □-anomer. The 2'-OH of the ribose sugar may be altered to form 2'-O-methyl or 2'-O-allyl sugars, which provides resistance to degradation without comprising affinity.

Agents are screened for biological activity by adding the agent to at least one and usually a plurality of cells, in one or in a plurality of environmental conditions, e.g. following stimulation with a β-adrenergic agonist, following electric or mechanical stimulation, etc. The change in parameter readout in response to the agent is measured, desirably normalized, and the resulting screening results may then be evaluated by comparison to reference screening results, e.g. with cells having other mutations of interest, normal cardiac fibroblasts, cardiac fibroblasts derived from other family members, and the like. The reference screening results may include readouts in the presence and absence of different environmental changes, screening results obtained with other agents, which may or may not include known drugs, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of selected parameters, in addition to the functional parameters described above. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

The comparison of a screening results obtained from a test compound, and a reference screening results(s) is accomplished by the use of suitable deduction protocols, AI systems, statistical comparisons, etc. Preferably, the screening results is compared with a database of reference screening results. A database of reference screening results can be compiled. These databases may include reference results from panels that include known agents or combinations of agents, as well as references from the analysis of cells treated under environmental conditions in which single or multiple environmental conditions or parameters are removed or specifically altered. Reference results may also be generated from panels containing cells with genetic constructs that selectively target or modulate specific cellular pathways.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

EXAMPLES

MAB21L4 Controls RET-Dependent Epidermal Differentiation and Neoplastic Invasion Few targeted therapies are available to treat advanced cutaneous squamous cell carcinoma (SCC). By focusing on uncharacterized proteins in transcriptomic analyses comparing human SCC to differentiating primary keratinocytes, we identified reciprocal expression of MAB21L4, a mab-21-like protein of unknown function. Genetic ablation of MAB21L4 prevented induction of key differentiation genes in normal human skin organoids and accelerated conversion to invasive neoplasia. Proximal proteomics applied to MAB21L4 revealed a critical role for ubiquitin ligase-associated CacyBP and disruption of the MAB21L4-CacyBP interaction stabilized expression of the RET proto-oncogene by preventing its ubiquitination. RET was required to maintain the undifferentiated cell state in human epidermal tissue and selective inhibition of RET effectively suppressed transformation of normal human skin organoids into invasive neoplasia. Taken together, these data demonstrate a tumor suppressive role for the uncharacterized protein MAB21L4 that involves RET inhibition and identify RET as a therapeutic target in SCC.

Uncharacterized open reading frames (ORFs) in the human genome frequently lack detectable homology to proteins of known function, which may delay their experimental characterization. Despite these challenges, an increasing number of genes originally from this pool are currently appreciated to control a diverse range of fundamental cellular and biological processes, including regulation of Wnt signaling, cell cycle progression, and effector T cell homing. In this study, we searched this group of uncharacterized candidates for a regulator of epidermal differentiation with a functional role in SCC development and focused on its interactions with established cancer pathways to inform future efforts aimed at developing molecular targeted therapy for this malignancy.

Figure 8:
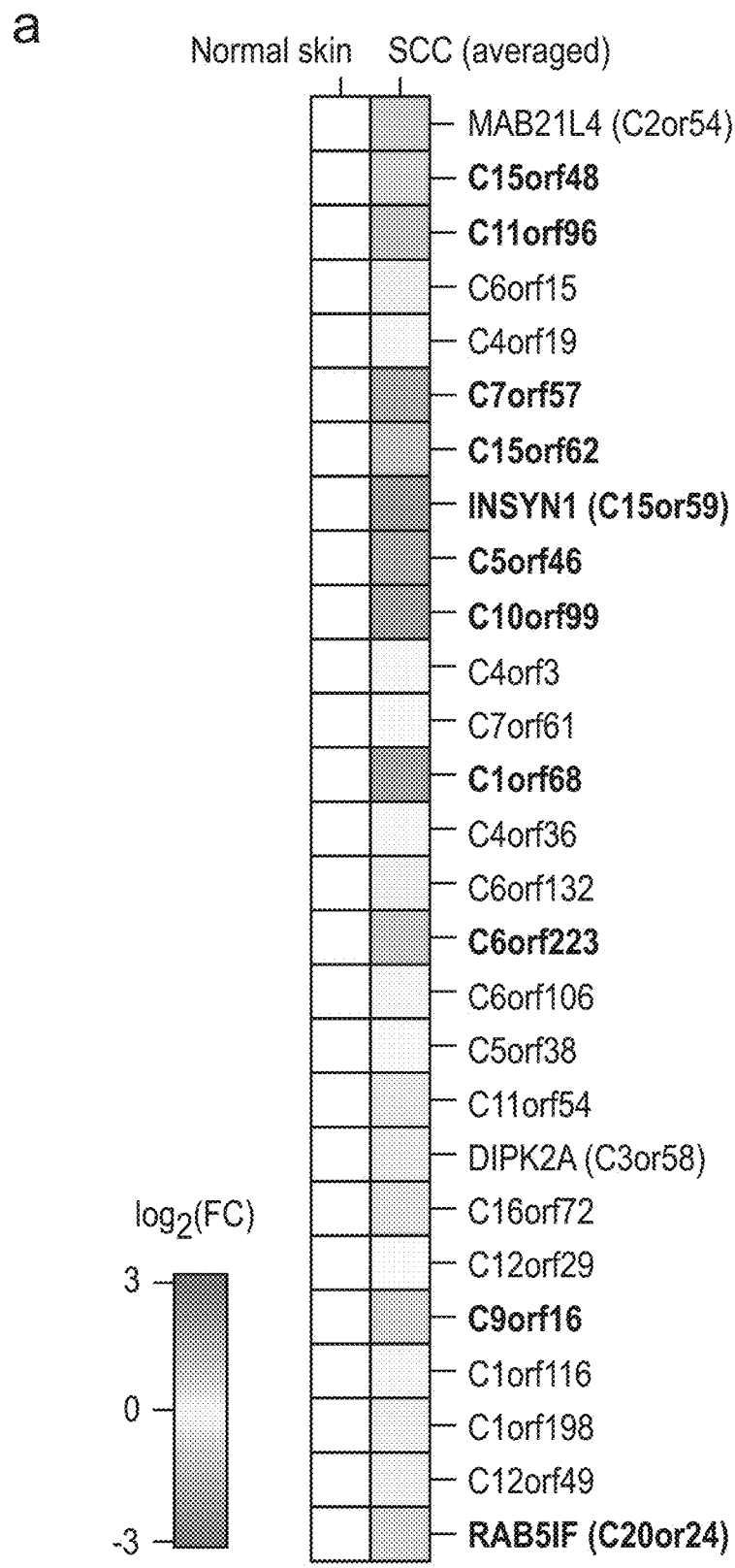
FIG. 8. Decreased expression of MAB21L4 in human cancers (a) Expression of uncharacterized ORFs upregulated in differentiation was assessed in 11 SCC using RNA-seq. Bolded gene names indicate a log 2 fold change (FC) with an adjusted p-value<0.05. (b) Representative images of MAB21L4 expression levels in SCC tissues. Scale bar, 50 µm. (c) Deletion frequency of the MAB21L4 locus in 23 TCGA cancer types. Analysis was restricted to genomic segments that do not include known tumor suppressor genes. (d) Cox multivariable analysis of MAB21L4 expression and survival in the TCGA head and neck SCC (HNSC) cohort after adjusting for age, sex, and clinical stage.
Figure 8:
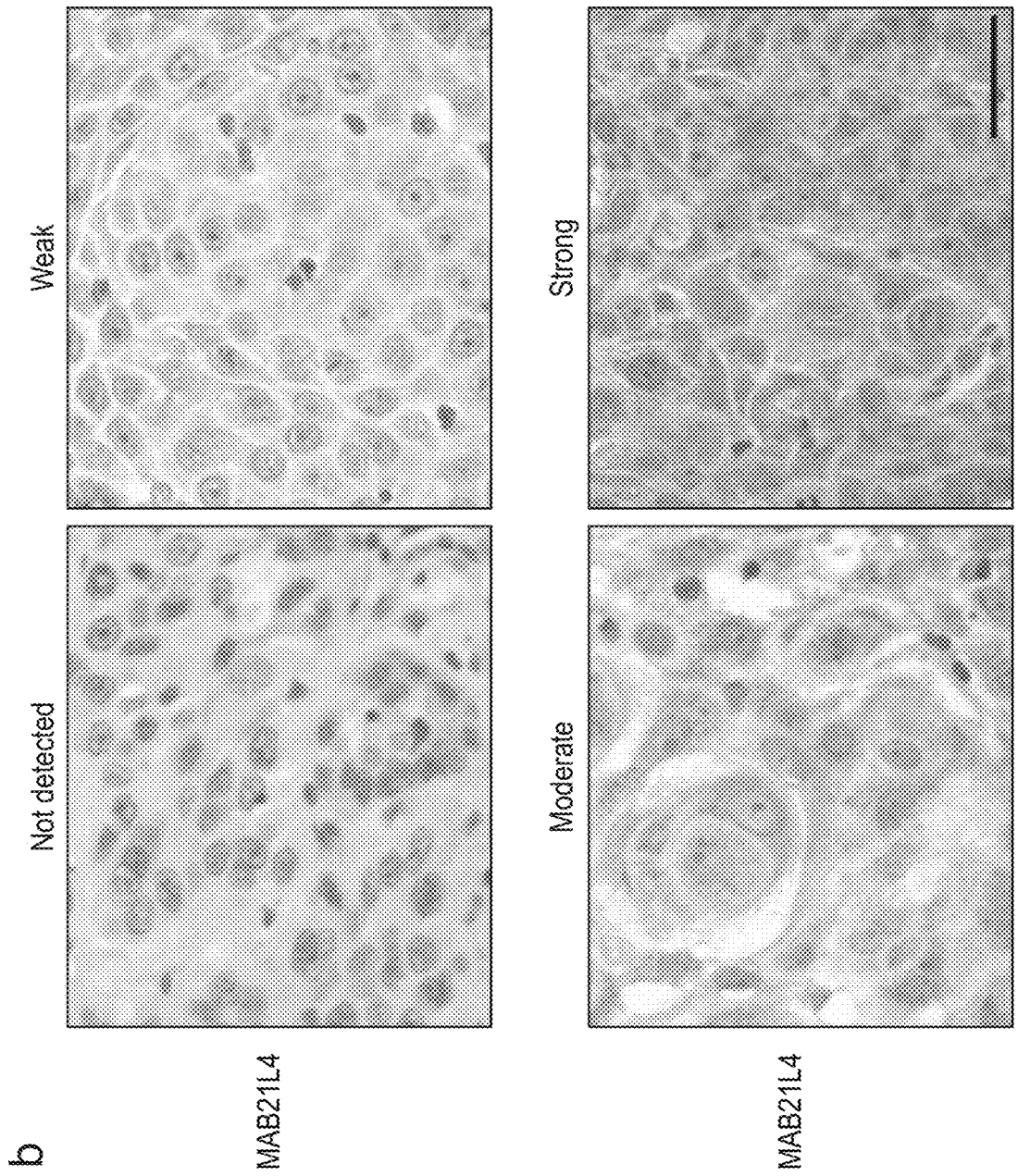
Figure 8:
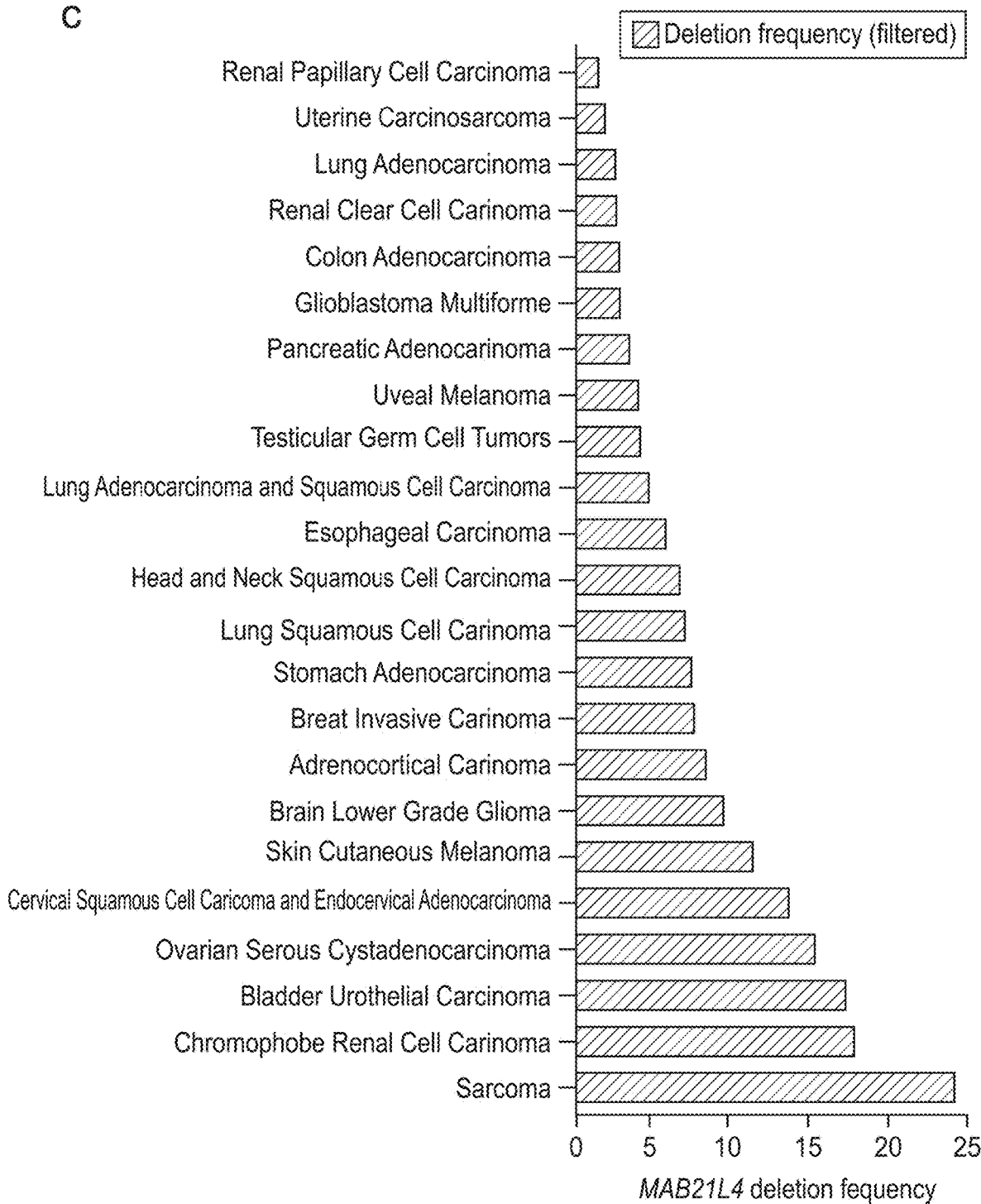
Figure 8:
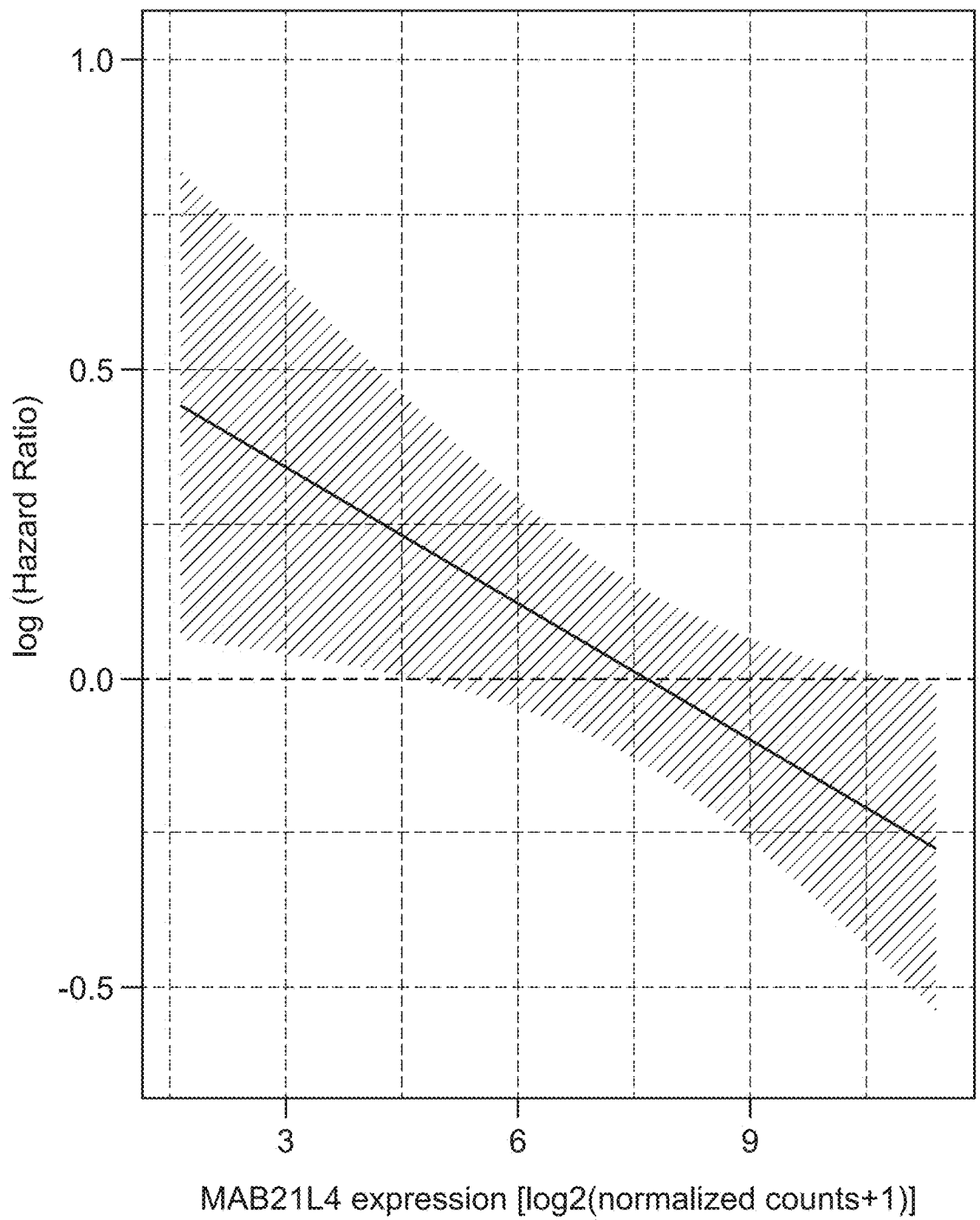

Uncharacterized protein MAB21L4 is targeted in differentiation and cancer. To identify regulators of epidermal differentiation disrupted in malignancy, we interrogated RNA sequencing data from progenitor and differentiating human keratinocytes as well as eight SCC with patient-matched normal skin to complement the three tumor-normal pairs previously reported. This effort highlighted 27 uncharacterized ORFs that are increased at least 2-fold at the mRNA level during differentiation, most notably MAB21L4 (also known as C2ORF54), which encodes a 447 amino acid protein of unknown function that was increased >480-fold in cultured primary keratinocytes on day 6 of differentiation in calcium-containing medium and significantly downregulated in human SCC (FIG. 1a and FIG. 8a). Progressive induction of MAB21L4 during epidermal differentiation was confirmed at both the mRNA and protein levels (FIG. 1b,c).

Consistent with this pattern of expression, MAB21L4 protein was detected in the suprabasal compartment of normal human skin by immunofluorescence (FIG. 1d). Subsequent analysis of publicly available microarray data for genes that possess Boolean implications with MAB21L4 revealed low expression of MAB21L4 correlates with low expression of genes assigned to skin development and differentiation (FIG. 1e). These data indicate MAB21L4 expression coincides with engagement of the terminal differentiation gene expression program in the skin and may regulate this process. To verify the opposite pattern of MAB21L4 expression in cancer, immunohistochemistry was performed and demonstrated reduced expression of MAB21L4 in SCC as well as actinic keratoses (AK), the earliest clinically detectable SCC precursors (FIG. 1f and FIG. 8b).

These data are consistent with the downregulation of MAB21L4 observed at the mRNA level in SCC and suggest that loss of MAB21L4 expression occurs early in SCC development. We next investigated whether MAB21L4 is subject to somatic copy number alterations (SCNAs) as genes frequently inactivated through deletion may function as tumor suppressors. SCNAs were analyzed in 9,927 pairs of tumor and matching normal genomes in 27 human cancer types in The Cancer Genome Atlas (TCGA) data set after filtering out genomic segments containing known tumor suppressor genes. Somatic loss of MAB21L4 occurred at a frequency >10% in multiple TCGA cancer types, including cervical SCC and cutaneous melanoma (FIG. 8c). In these and other malignancies, MAB21L4 was present at the nadir of the peak formed by aligning regions of somatic copy number deletions (FIG. 1g). Further support for somatic MAB21L4 loss was provided using the GISTIC algorithm, which finds MAB21L4 deleted across all tumor types in 18.8% and places it in a focal peak of deletion in 21 TCGA cancer types.

We then performed Cox proportional hazard analysis of MAB21L4 expression in the TCGA head and neck SCC cohort and observed that increased expression is associated with longer survival (FIG. 8d). After adjusting for gender, age, and clinical stage, each unit of decreased MAB21L4 expression was revealed to result in an additional 7% increase in the hazard for death (Table 1). Taken together, these data support a model whereby loss of MAB21L4 is tumor promoting.

TABLE 1

Cox proportional hazard model of survival in the TCGA head and neck SCC (HNSC) cohort.

| Variable | HR (Multivariable) |
| --- | --- |
| Age | 1.02 (1.01-1.03, p = 0.003) |
| Gender | |
| Female | Reference |
| Male | 0.77 (0.57-1.04, p = 0.084) |
| Clinical Stage | |
| Stage 1 | Reference |
| Stage 2 | 1.06 (0.47-2.37, p = 0.890) |
| Stage 3 | 1.27 (0.57-2.83, p = 0.562) |
| Stage 4 | 1.35 (0.63-2.90, p = 0.443) |
| MAB21L4 mRNA Expression | 0.93 (0.88-0.99, p = 0.015) |

Parentheses indicate 95% confidence intervals and p-value. HR, hazard ratio.

MAB21L4 controls differentiation in human epidermal tissue. MAB21L4 is named for its resemblance to the mab-21 gene, which acts cell autonomously to control tail pattern in C. elegans males as well as non-autonomously to specify cell fate outside of the tail region. Three homologs of mab-21, termed mab-21-like 1 (MAB21L1), mab-21-like 2 (MAB21L2), and mab-21-like 3 (MAB21L3) have been characterized in vertebrates that together control early embryogenesis and differentiation, impacting eye, head, neural tube, and body wall development. By contrast, MAB21L4 has not been functionally characterized, with only one published report implicating its differential expression in esophageal cancer. With the exception of mab21l3, which has been shown to control differentiation in Xenopus embryonic epidermis, the role of mab-21 proteins in the skin is largely unknown.

Figure 2:
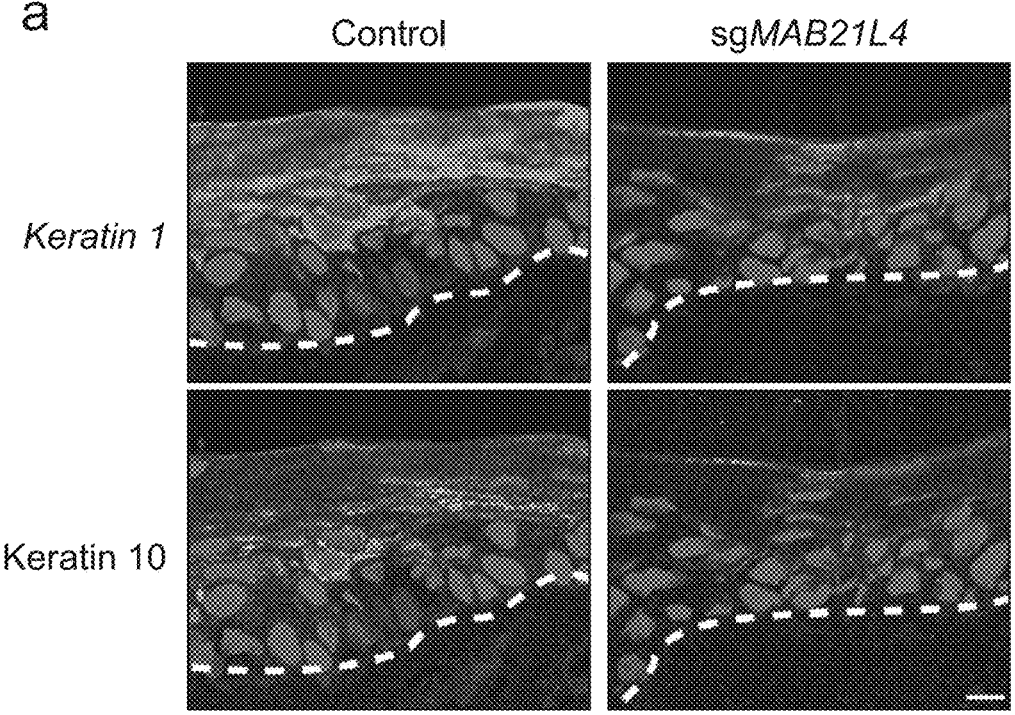
FIG. 2. MAB21L4 controls differentiation in human epidermal tissue (a) Expression of differentiation proteins in MAB21L4-ablated (sgMAB21L4) human skin organoids generated by CRISPR/Cas9-mediated genetic disruption compared to a nontargeting control after 3 days of growth on dermis; differentiation proteins detected by immunofluorescence in red (keratin 1) and green (keratin 10), dotted line indicates basement membrane zone. Scale bar, 10 µm. (b) Differentiation gene mRNA quantitation in human skin organoids generated using two independent MAB21L4 sgRNAs compared to control sgRNA and after 3 days of growth on dermis. Bars represent mean±SD, three technical replicates per experiment. (c) Expression of differentiation proteins in human skin organoids generated from keratinocytes transduced to express MAB21L4 at near-physiologic levels and after 3 days of growth on dermis; differentiation proteins detected by immunofluorescence in red (keratin 1) and green (keratin 10), dotted line indicates basement membrane zone. Scale bar, 10 µm. (d) Differentiation gene mRNA quantitation in human skin organoids with enforced expression of MAB21L4 compared to a control vector and after 3 days of growth on dermis. Bars represent mean±SD, three technical replicates per experiment. For all panels, data are representative of n=3 biological replicates.
Figure 2:
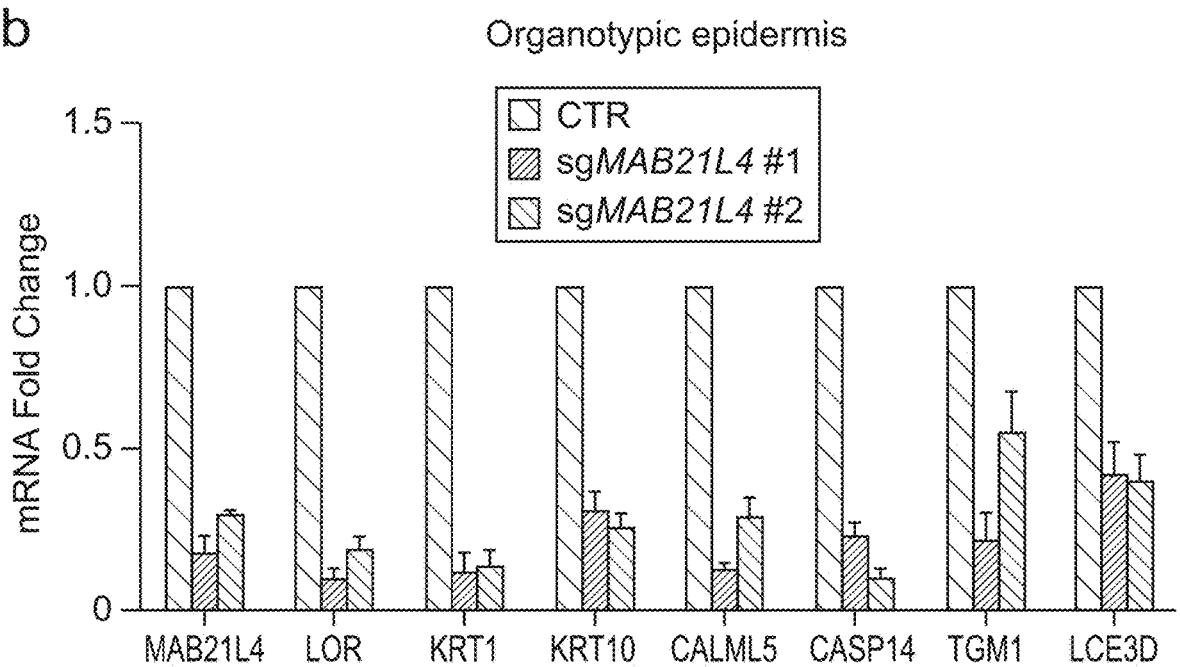
Figure 2:
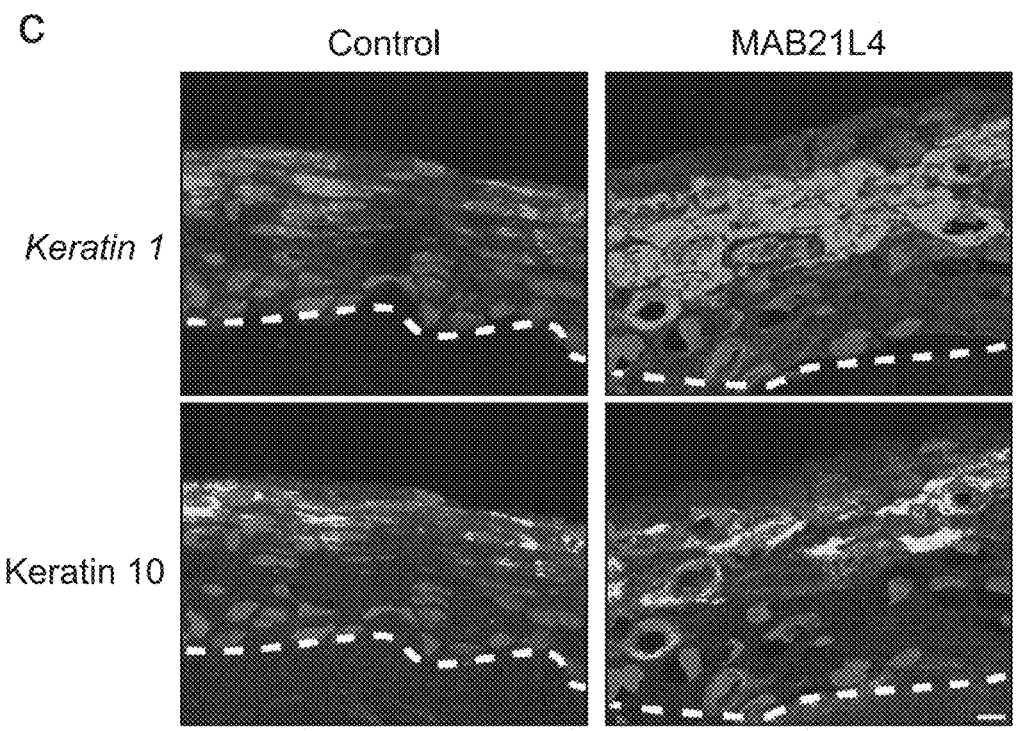
Figure 2:
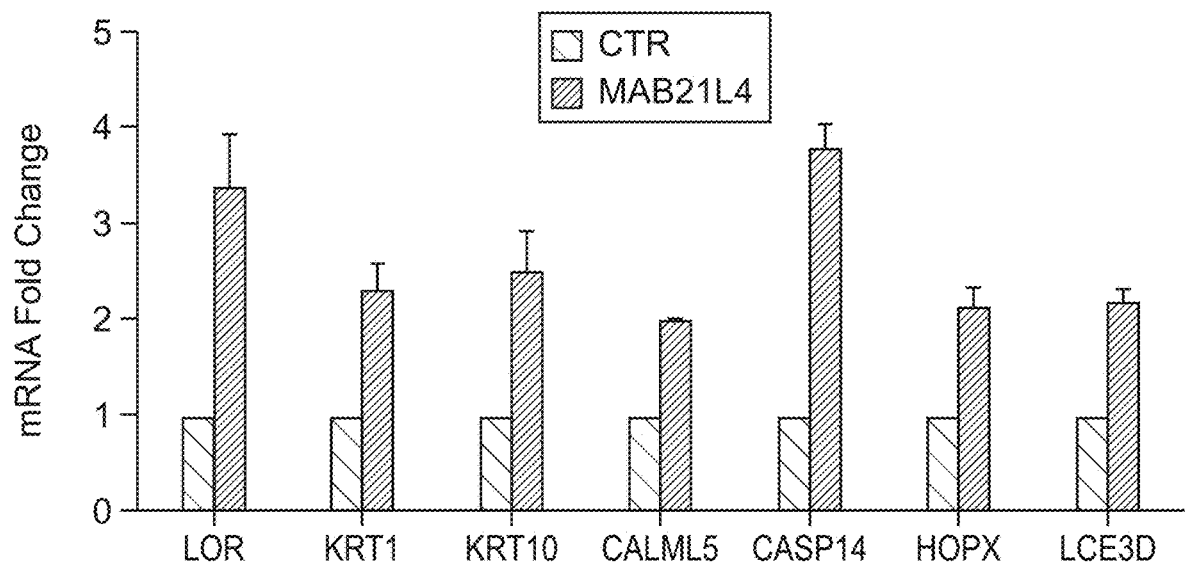

To define MAB21L4 function in the epidermis, we investigated the effects of MAB21L4 loss and gain in three-dimensional human skin organoids, a setting that faithfully recapitulates the architecture and gene expression profile of normal skin. CRISPR/Cas9-mediated genetic disruption with two independent single guide RNAs (sgRNAs) was used to create pools of MAB21L4-ablated primary human keratinocytes. These gene-targeted cells were then placed onto human dermis and grown for three days at the air-liquid interface to generate organotypic skin tissue. Deletion of MAB21L4 attenuated the expression of both early (KRT1, KRT10, CALML5, CASP14) and late (TGM1, LOR, HOPX, LCE3D) differentiation markers in regenerated skin tissue without affecting epidermal stratification (FIG. 2a,b). Conversely, enforced expression of MAB21L4 resulted in increased expression of these genes (FIG. 2c,d). These results together illustrate that MAB21L4 is required for epidermal differentiation.

Figure 3:
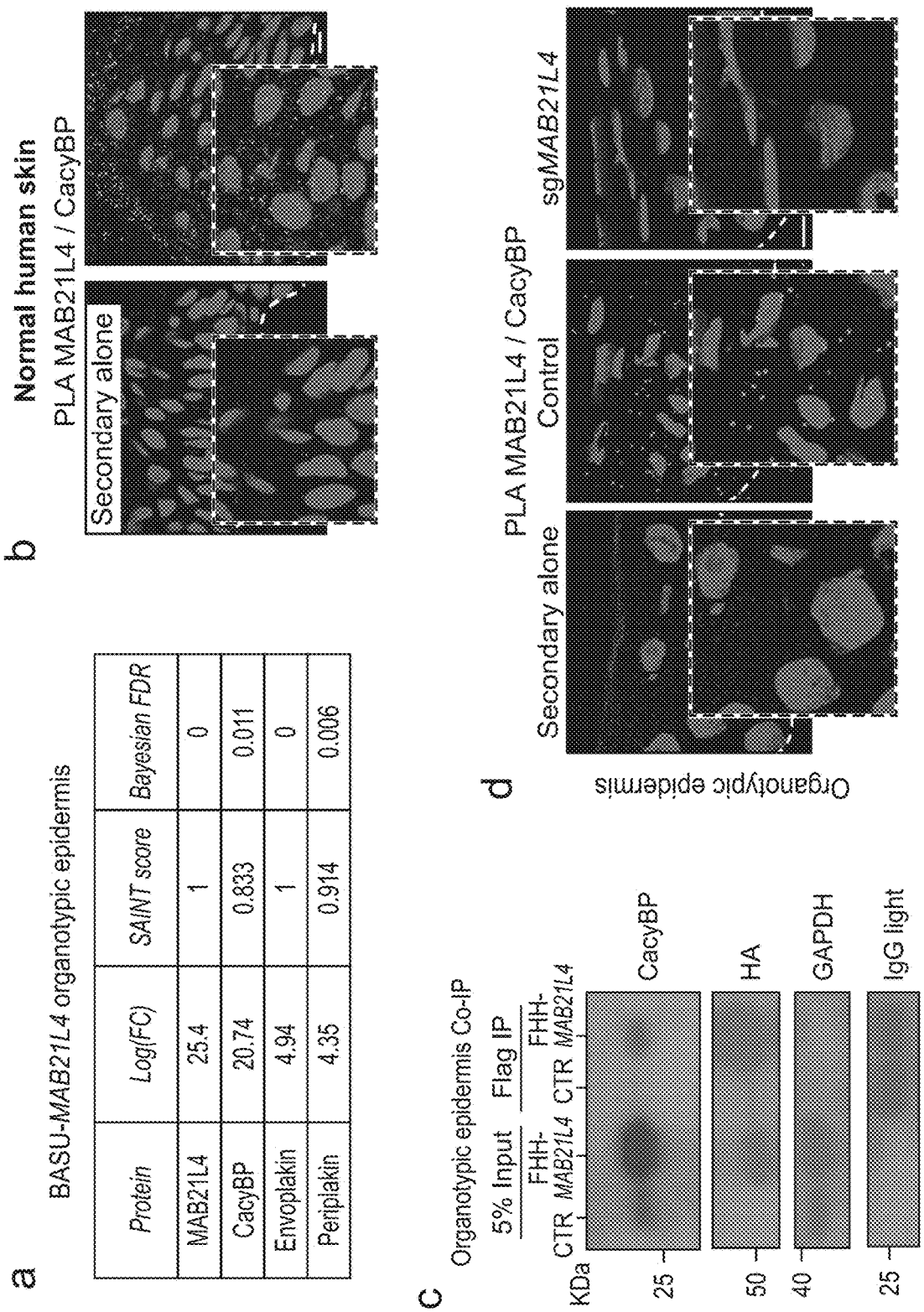
FIG. 3. CacyBP is a MAB21L4-proximal protein in human epidermis (a) Top MAB21L4-proximal proteins identified by BioID performed in human skin organoids. Data represent 3 biological replicates each performed in technical triplicate. (b) PLA of endogenous MAB21L4 and CacyBP in normal human adult skin. PLA was performed in the absence of primary antibodies as a control (Secondary alone). Scale bar, 10 µm. (c) Western blot analysis of FLAG co-immunoprecipitation of empty vector (CTR) or FLAG-HA-6×HIS (FHH)-MAB21L4 with endogenous CacyBP in human organotypic epidermis. Data shown represent n=3 pooled technical replicates. (d) PLA of endogenous MAB21L4 and CacyBP in human skin organoids generated from MAB21L4-ablated primary keratinocytes (sgMAB21L4) compared to control sgRNA and after 3 days of growth on dermis. Scale bar, 10 µm. (e) Quantitation of PLA analysis in (d) with two independent MAB21L4 sgRNAs; PLA index is the number of dots per number of nuclei in n=3 fields of view. Data shown represent the mean±SD; significance was calculated using one-way ANOVA. (f) PLA of endogenous MAB21L4 and CacyBP in human skin organoids generated from CACYBP-ablated primary keratinocytes (sgCACYBP) compared to control sgRNA and after 3 days of growth on dermis. Scale bar, 10 µm. (g) Quantitation of PLA analysis in (f) with two independent CACYBP sgRNAs; data represent the mean PLA index of n=3 fields of view ±SD; significance was calculated using one-way ANOVA. (h) Expression of differentiation marker keratin 10 (green) in CACYBP (red)-ablated human skin organoids generated by CRISPR/Cas9-mediated genetic disruption compared to a non-targeting control after 3 days of growth on dermis; dotted line indicates basement membrane zone. Data are representative of 3 biological replicates. Scale bar, 10 µm. (i) Differentiation gene mRNA quantitation in human skin organoids generated using two independent CACYBP sgRNAs compared to control sgRNA and after 3 days of growth on dermis. (j) Venn diagram illustrating overlap between downregulated (↓) genes in CACYBP-ablated and MAB21L4-ablated organotypic epidermis (n=2 biological replicates). (k) Top GO terms associated with the 1,027 genes downregulated when CACYBP or MAB21L4 are deleted in organotypic epidermis (pvalues were adjusted using the Benjamini-Hochberg procedure). Data are representative of 3 biological replicates; bars represent mean±SD, three technical replicates per experiment. All insets provide a close-up view of PLA signal.
Figure 3:
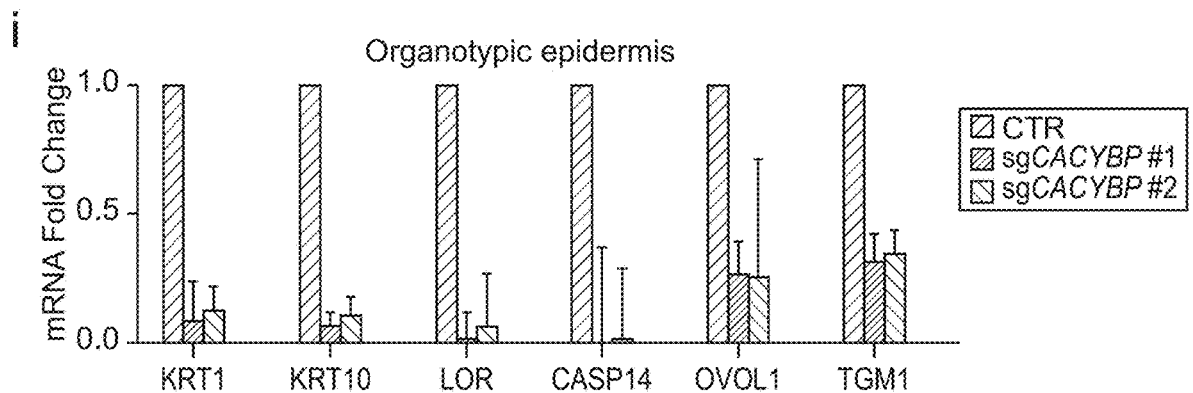
Figure 3:
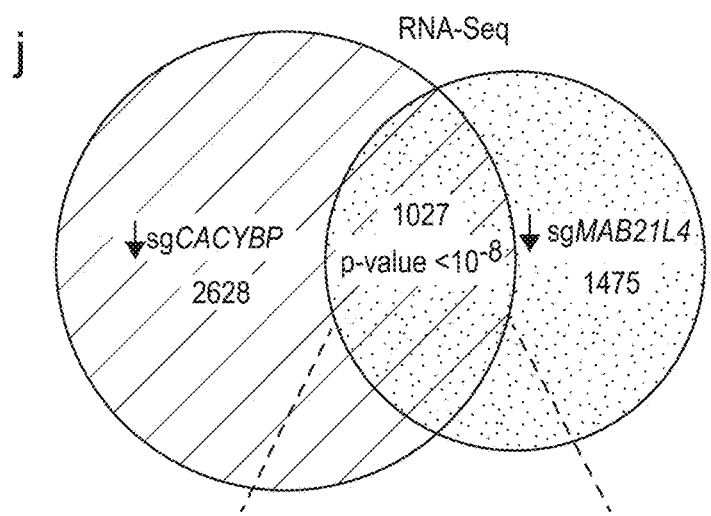
Figure 3:
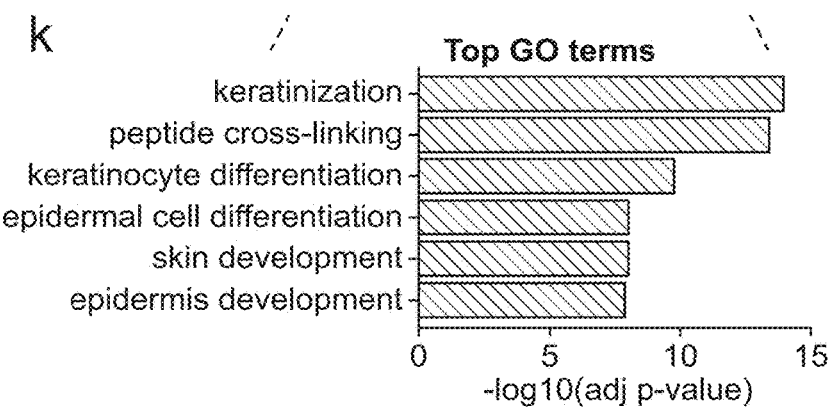
Figure 9:
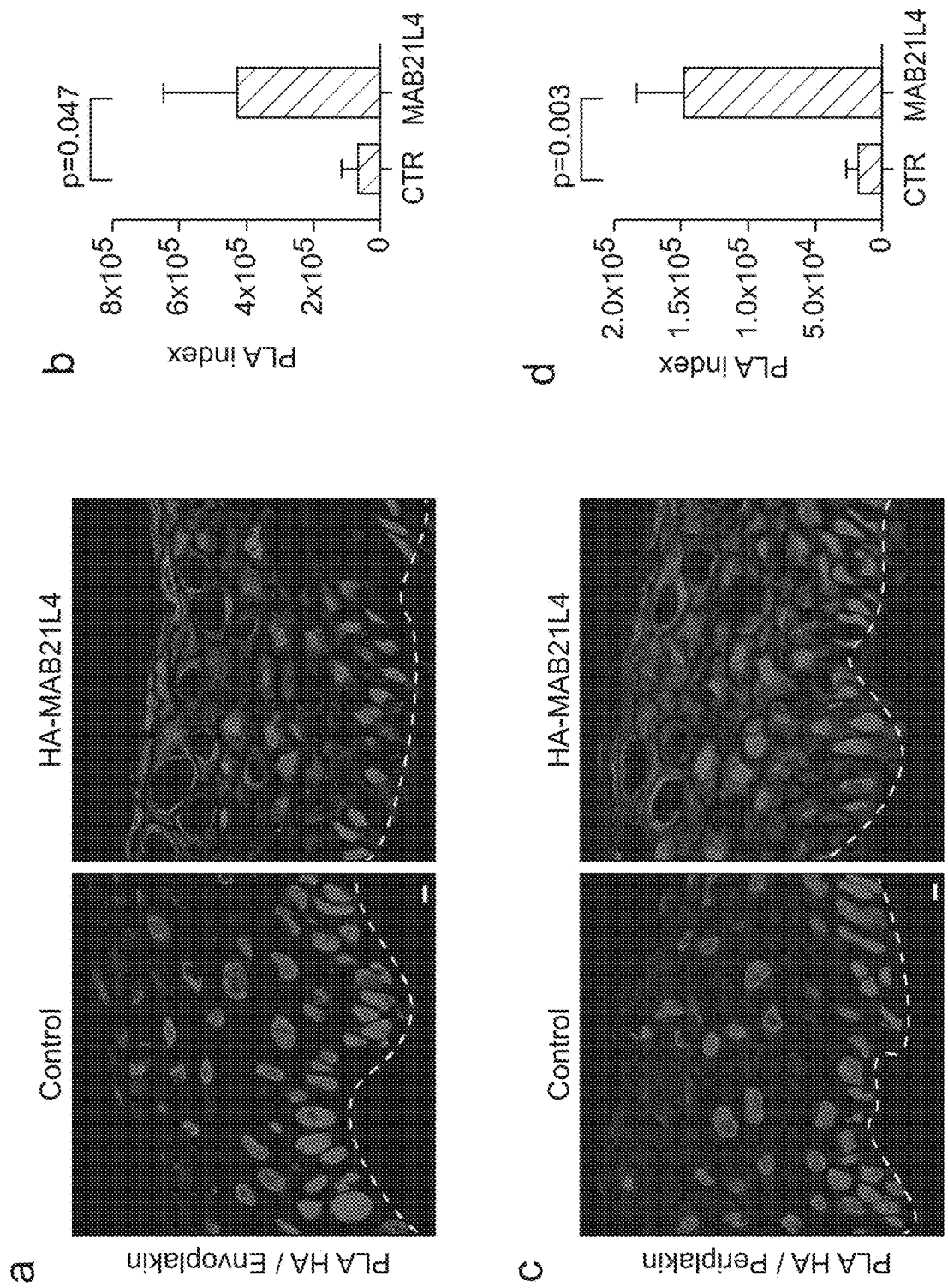
FIG. 9. MAB21L4-proximal proteins in human epidermis (a) PLA of endogenous envoplakin and HA in human skin organoids generated from human primary keratinocytes transduced to express HA-MAB21L4 or an empty vector (Control). Scale bar, 10 µm. (b) Quantitation of PLA analysis in (a); PLA index (integrated density of signal per number of nuclei) was calculated for 3 fields of view. (c) PLA of endogenous periplakin and HA in human skin organoids generated from human primary keratinocytes transduced to express HA-MAB21L4 or an empty vector (Control). Scale bar, 10 µm. (d) Quantitation of PLA index in (c); PLA index (integrated density of signal per number of nuclei) was calculated for 3 fields of view. (e) Expression of CacyBP (red) in normal human adult skin; collagen VII (green) decorates the basement membrane zone. Scale bar, 10 µm. (f) PLA of endogenous CacyBP and HA in human skin organoids generated from human primary keratinocytes transduced to express HA-MAB21L4 or an empty vector (Control). Scale bar, 10 µm. (g) Quantitation of PLA index in (f); PLA index (% of number of dots per number of nuclei) was calculated for 3 fields of view. (h) Western blot analysis of MAB21L4 expression in organotypic epidermis generated from MAB21L4-ablated human primary keratinocytes via two independent sgRNAs 36 (sgMAB21L4) compared to a non-targeting control sgRNA (Control). (i) Western blot analysis of CacyBP expression in organotypic epidermis generated from CACYBP-ablated human primary keratinocytes via two independent sgRNAs (sg CACYBP) compared to a non-targeting control sgRNA (Control). All skin organoids were harvested 6 days after seeding onto dermis. All quantitations of PLA index represent the mean±SD; significance was calculated using a two tailed t-test.
Figure 9:
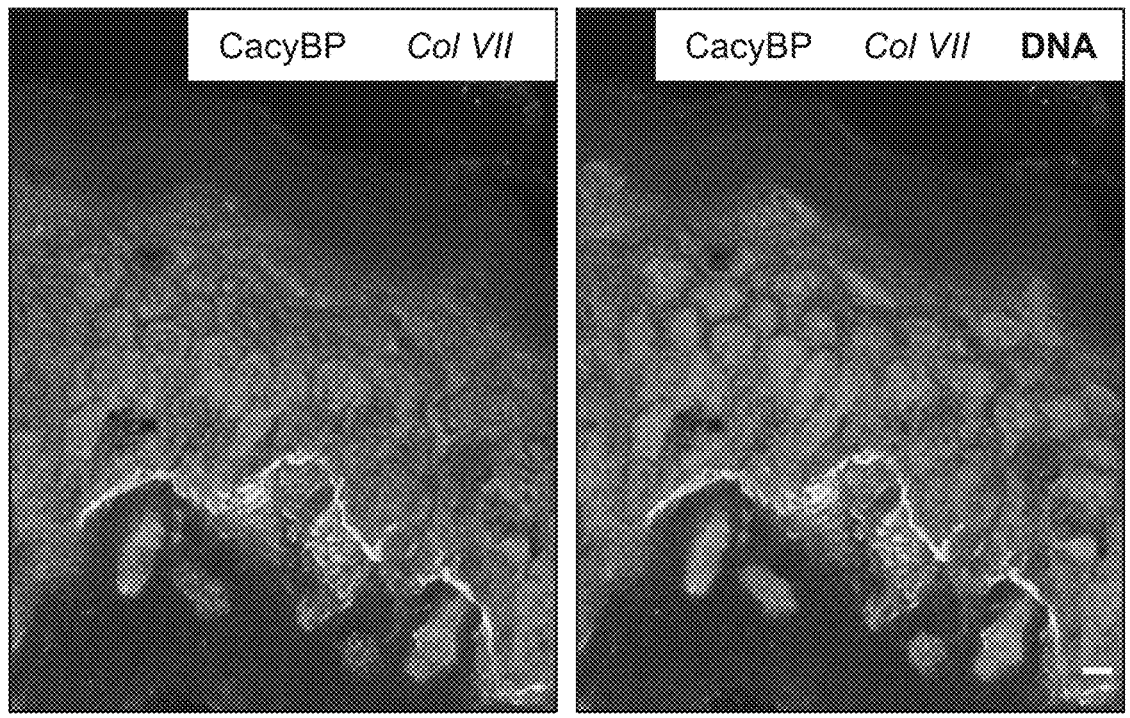
Figure 9:
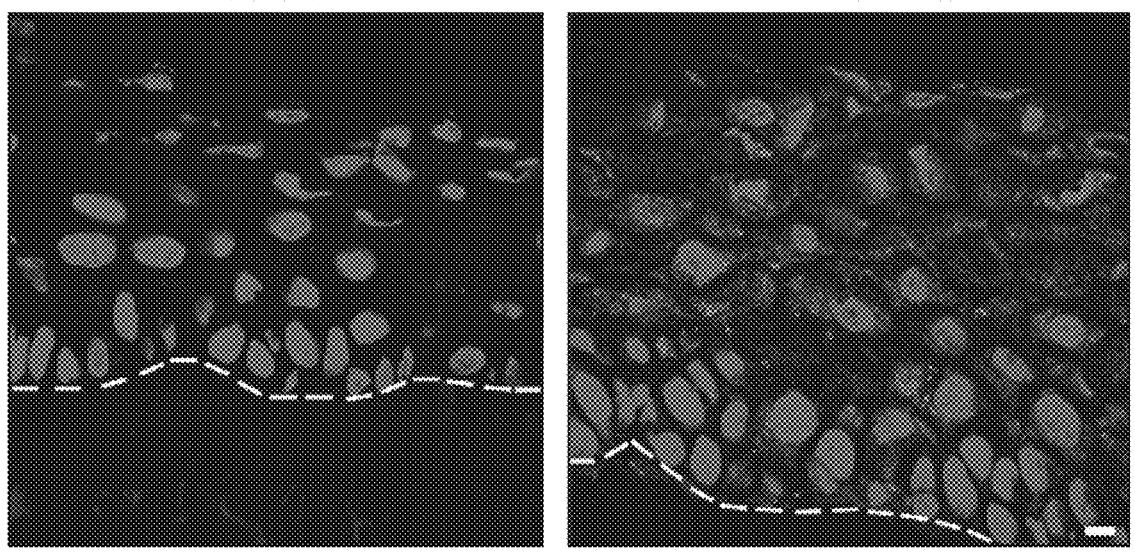
Figure 9:
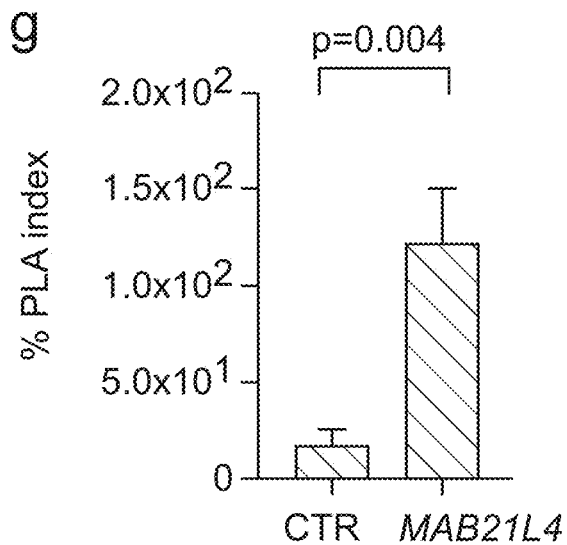
Figure 9:
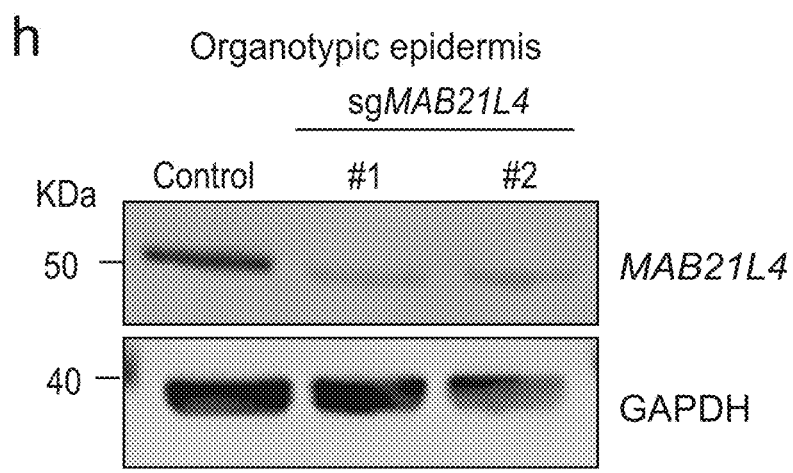
Figure 9:
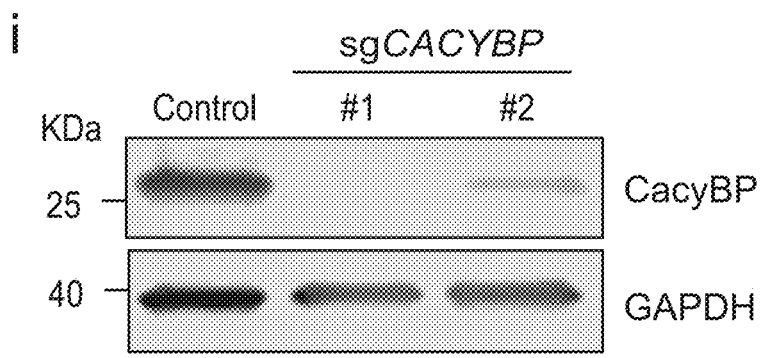

MAB21L4 proximity to CacyBP regulates epidermal differentiation. To gain insight into the molecular mechanisms underlying MAB21L4's impacts on differentiation, we defined its protein interaction partners in organotypic human skin tissue using proximity-dependent biotin identification (BioID). MAB21L4 was fused to BASU, a Bacillus subtilis-derived biotin ligase with faster labeling kinetics and an improved signal-to-noise ratio compared to E.coli BirA. Primary human keratinocytes transduced to express the BASUMAB21L4 fusion protein at levels approximating endogenous MAB21L4 expression or BASU only as control were used to generate human skin organoids. Following biotin labeling, streptavidin pull-down, and mass spectrometry analysis, the top MAB21L4-proximal proteins based on fold change over control and significance analysis of interactome (SAINT) score included those known to be essential for epidermal barrier function, such as envoplakin and periplakin, as well as proteins that are uncharacterized in skin, such as calcyclin-binding protein (CacyBP), also known as Siah-1 interacting protein (SIP) (FIG. 3a). Proximity ligation assays (PLA) confirmed MAB21L4 co-localization with envoplakin (FIG. 9a,b) and periplakin (FIG. 9c,d).

We next focused on CacyBP, which is known to interact with members of the S100 family, cytoskeletal proteins, and components of E3 ubiquitin ligases, but whose expression and activity have not been studied in skin. Immunostaining of CacyBP in adult human skin demonstrated its presence throughout the epidermis as well as in fibroblasts, suggesting it might co-localize with MAB21L4 in the suprabasal compartment (FIG. 9e). We first confirmed the physical proximity of endogenous MAB21L4 and CacyBP in adult human skin by PLA (FIG. 3b). We then generated human skin organoids from keratinocytes transduced to express epitope-tagged MAB21L4 and demonstrated the association between these proteins by PLA (FIG. 9f,g) as well as co-immunoprecipitation (FIG. 3c). To further support this interaction, we next ablated either MAB21L4 or CACYBP using CRISPR/Cas9 in human organotypic epidermal tissue. In each case, two independent sgRNAs were used to target MAB21L4 or CACYBP in keratinocytes that were then used to generate skin organoids for PLA analysis (FIG. 9h,i). Loss of either MAB21L4 (FIG. 3d,e) or CacyBP (FIG. 3f,g) abolished MAB21L4-CacyBP fluorescent PLA signal. These data establish the physical proximity of MAB21L4 and CacyBP in three-dimensionally intact skin tissue. We confirmed a previously unrecognized role for CacyBP in maintaining epidermal homeostasis by demonstrating impaired expression of differentiation markers in CACYBPablated human skin organoids that recapitulated the effects of MAB21L4 depletion (FIG. 3h,i). To more fully investigate the relationship between MAB21L4 and CacyBP, we then analyzed MAB21L4- or CACYBP-deficient organotypic human skin tissues by RNA sequencing. This effort distilled a set of 1,027 coordinately downregulated genes enriched with those assigned to keratinization, keratinocyte differentiation, and skin development gene ontology (GO) terms (FIG. 3j,k). We also observed enrichment of peptide cross-linking genes that encode transglutaminases and multiple cornified envelope components essential for the mechanical integrity and barrier function of the skin (FIG. 3k). These results suggest that MAB21L4-dependent control of epidermal differentiation requires CacyBP.

MAB21L4 suppresses Ras-driven invasion in human skin tissue. The newly defined role of MAB21L4 in epidermal differentiation, coupled with its somatic loss and/or downregulation in malignancy, prompted us to consider its function in SCC. To investigate MAB21L4 function in cancer, we generated human skin organoids programmed by oncogenic H-Ras and cyclin dependent kinase Cdk4 to transform into invasive epidermal neoplasia that faithfully recapitulates the histology and global gene expression profile of human SCC. MAB21L4 expression is decreased in this setting compared to non-transformed skin tissue, consistent with its downregulation in human SCC (FIG. 10a).

Figure 4:
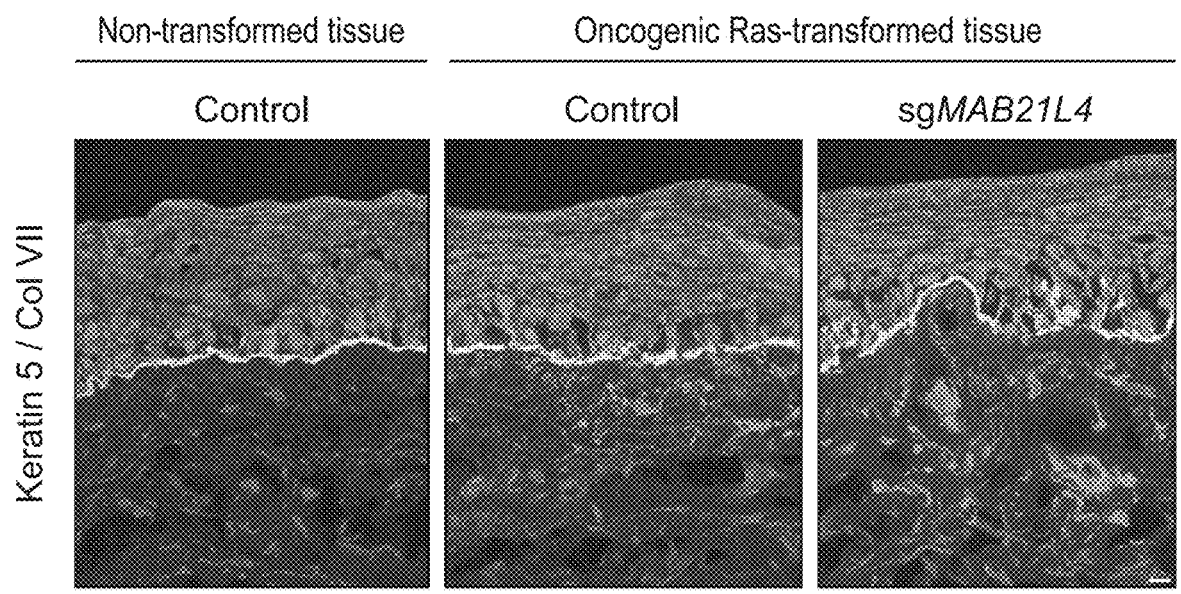
FIG. 4. MAB21L4 impact on invasive human epidermal neoplasia (a) Normal primary human keratinocytes seeded onto dermis do not breach the epithelial boundary defined by the basement membrane (left); however, oncogenic Ras-expressing keratinocytes (keratin 5, red) invade into the stroma in this model (middle). Depletion of MAB21L4 using CRISPR/Cas9-mediated genetic disruption (sgMAB21L4) potentiates invasion (right). Data representative of n=3 technical replicates. Scale bar, 10 µm. (b) Quantitation of invasion index in (a) with two independent MAB21L4 sgRNAs, calculated as the integrated density of keratin 5 staining beneath the basement membrane divided by the length of the basement membrane in n=4 fields of view. The invasion index of each field is shown along with the mean±SD; significance was calculated using one-way ANOVA. (c) Normal primary human keratinocytes seeded onto dermis do not breach the epithelial boundary defined by the basement membrane (left); however, oncogenic Ras-expressing keratinocytes (keratin 5, red) invade into the stroma (middle) and enforced expression of MAB21L4 suppresses Ras-driven invasion (right). Data representative of n=3 independent experiments, each performed with 3 technical replicates. Scale bar, 10 µm. (d) Quantitation of invasion index in (c), calculated as the integrated density of keratin 5 staining beneath the basement membrane divided by the length of the basement membrane in n=3 fields of view. The invasion index of each field is shown along with the mean±SD; significance was calculated using a two-tailed t-test.
Figure 4:
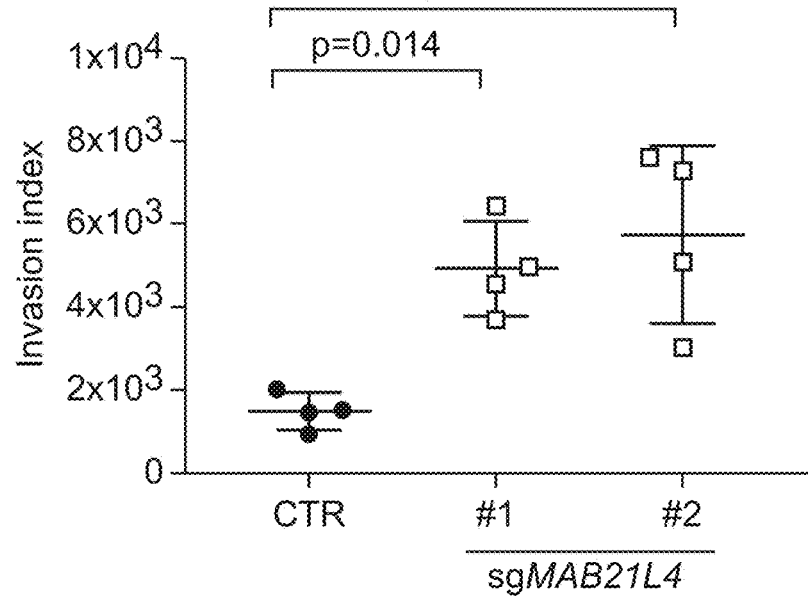
Figure 4:
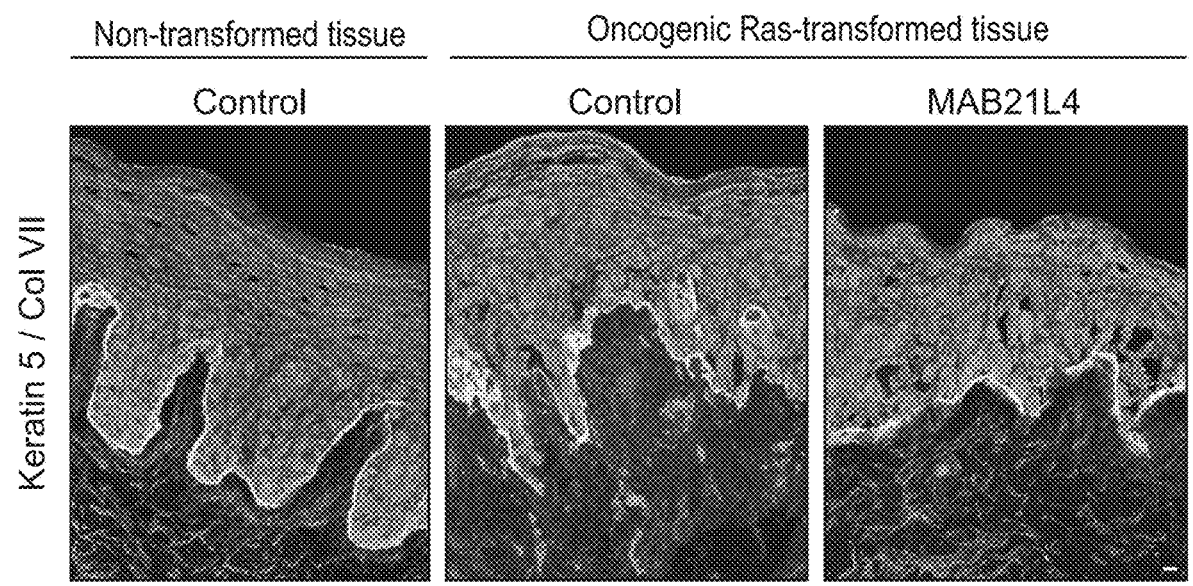
Figure 4:
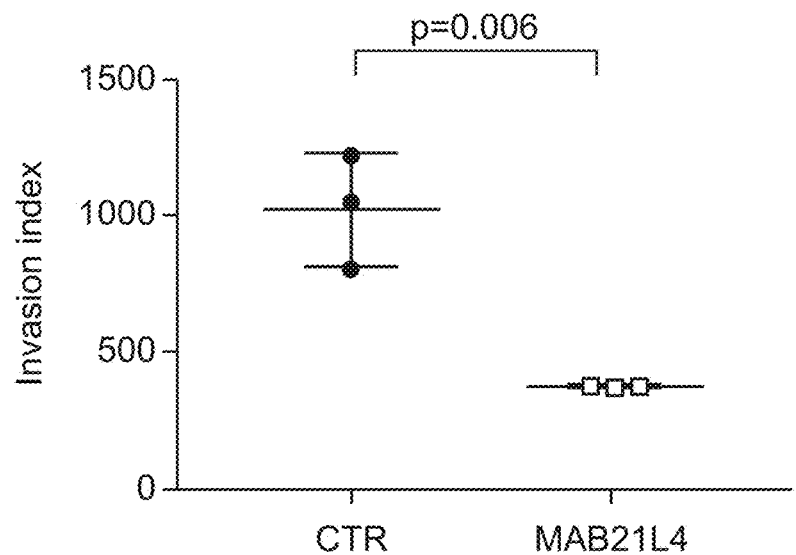

Genetic ablation of MAB21L4 with two independent sgRNAs potentiated Ras-driven neoplastic invasion, as evidenced by an increase in the number of keratinocytes present beyond the epidermal dermal boundary (FIG. 4a,b). Enforced expression of MAB21L4 had the reverse effect; basement membrane degradation and neoplastic invasion were profoundly suppressed in human skin organoids generated from keratinocytes transduced to express MAB21L4 and then programmed to transform by oncogenic H-Ras and Cdk4 (FIG. 4c,d and FIG. 10b).

Figure 10:
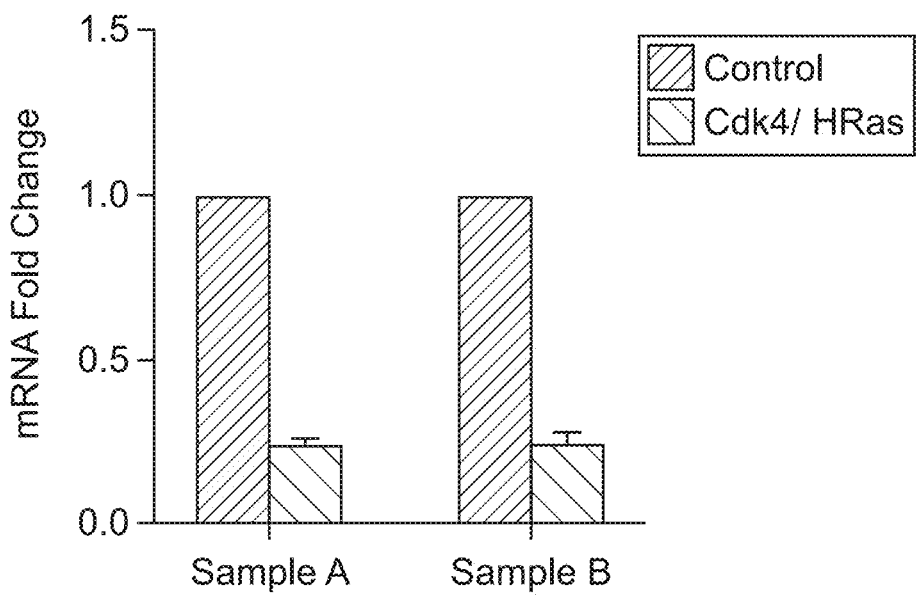
FIG. 10. MAB21L4 expression and impact on invasive human epidermal neoplasia (a) MAB21L4 transcript downregulation in organotypic human skin tissues programmed to transform into malignancy by oncogenic Cdk4/Ras and measured by quantitative qRT-PCR; sample A and B are biological replicates. Bars represent mean±SD, three technical replicates per experiment. (b) Western blot analysis of keratinocytes used to generate invasive human epidermal neoplasia. (c) Immunofluorescence of keratin 5 (red) and collagen VII (green) in xenografted epidermal tissues programmed to transform by oncogenic Cdk4/Ras; primary human keratinocytes were first transduced to express MAB21L4 or an empty vector as control. Arrowheads indicate areas of basement membrane disruption. Each experimental group contained n=3 mice and data show representative images from one Cdk4/Ras control xenograft as well as two different Cdk4/Ras/MAB21L4 xenografts. Scale bar, 10 µm. (d) Quantitation of invasion index in (c), calculated as the integrated density of keratin 5 staining beneath the basement membrane divided by the length of the basement membrane in 3 fields of view (one field per mouse). The invasion index of each field is shown along with the mean±SD; significance was calculated using a two-tailed t-test.
Figure 10:
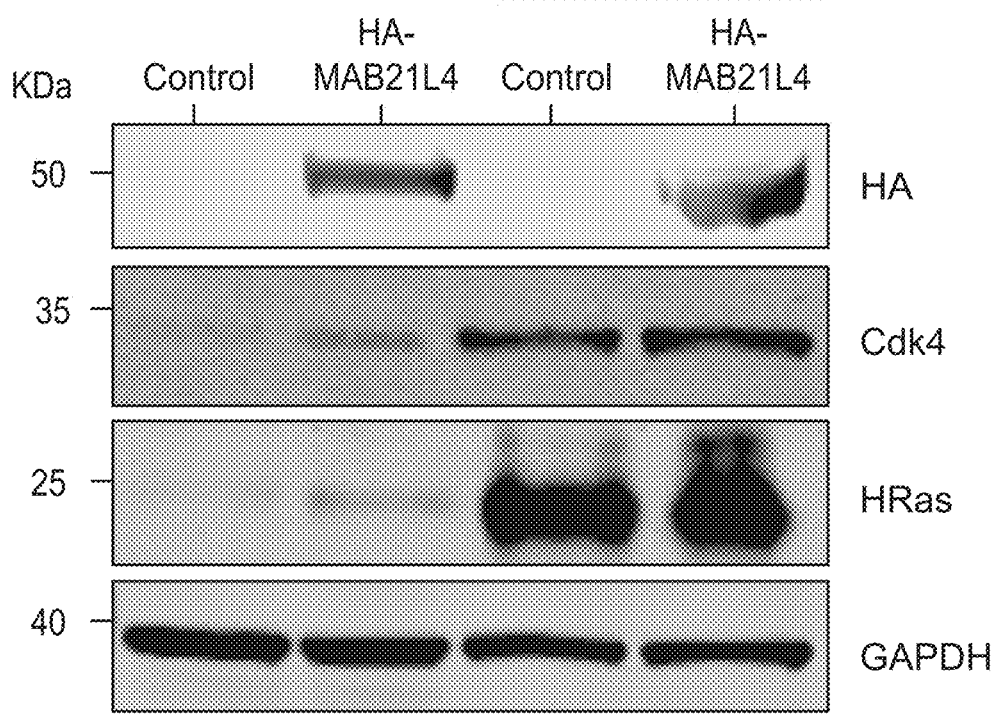

We then xenografted Ras-transformed human skin organoids that overexpress MAB21L4 or a control vector onto immune-deficient mice and confirmed that MAB21L4 effectively blocks neoplastic progression in vivo (FIG. 10c,d). Taken together, these loss—and gain of—function studies in human tissue indicate a tumor-suppressive role for MAB21L4 in the skin.

The MAB21L4-CacyBP interaction recruits RET for ubiquitination. Having established a role for MAB21L4 in the cancer setting, we explored the mechanism of its tumor-suppressive action by examining its dependent genes along with those of its binding partner, CacyBP. We therefore compared the differentially expressed genes identified in human skin organoids with MAB21L4 overexpression, MAB21L4 or CACYBP gene ablation, and human SCC. To focus on cancer-promoting genes that might be targeted by MAB21L4, we first investigated genes that were downregulated in the setting of enforced MAB21L4 expression and upregulated upon its deletion. The resulting gene set was then overlapped with the list of genes upregulated by CACYBP loss as well as those with increased expression in our series of 11 SCC.

Figure 5:
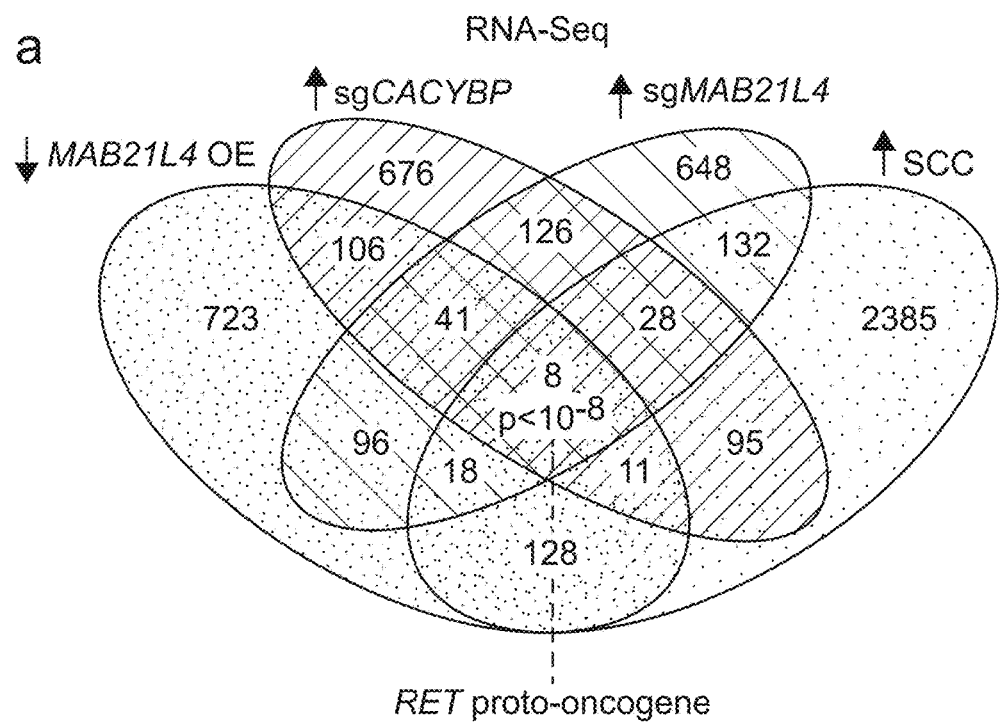
FIG. 5. The MAB21L4-CacyBP interaction mediates RET proximity and ubiquitination (a) Venn diagram illustrating overlap between genes upregulated in 11 human SCC compared to patient-matched normal skin as control (↑SCC), genes upregulated in MAB21L4-ablated organotypic epidermis (↑TsgMAB21L4), genes downregulated when MAB21L4 is overexpressed in regenerated epidermal tissue (↓MAB21L4 OE), and genes upregulated in CACYBP-ablated organotypic epidermis (↑sgCACYBP); the p-value for the intersection of all four datasets is shown and was determined by bootstrap resampling. (b) Quantitation of RET expression in normal skin and SCC. (c) PLA of endogenous CacyBP and RET in normal human adult skin. PLA was performed in the absence of primary antibodies as a control (Secondary alone). (d) PLA of endogenous CacyBP and RET in human skin organoids generated from MAB21L4-ablated primary keratinocytes (sgMAB21L4) compared to control sgRNA after three days of growth on dermis. (e) Quantitation of PLA analysis in (d) with two independent MAB21L4 sgRNAs. (f) PLA of endogenous ubiquitin and RET in human skin organoids generated from MAB21L4-ablated primary keratinocytes (sgMAB21L4) compared to control sgRNA and after 3 days of growth on dermis. (g) Quantitation of PLA analysis in (f) with two independent MAB21L4 sgRNAs. (h) PLA of endogenous ubiquitin and RET in human skin organoids generated from CACYBP-ablated primary keratinocytes (sgCACYBP) compared to control sgRNA and after 3 days of growth on dermis. (i) Quantitation of PLA analysis in (h) with two independent CACYBP sgRNAs. (j) PLA of endogenous Siah-1 and RET in human skin organoids generated from CACYBP-ablated primary keratinocytes (sgCACYBP) compared to control sgRNA and after 3 days of growth on dermis. (k) Quantitation of PLA analysis in (j) with two independent CACYBP sgRNAs. For all PLA images: scale bar, 10 µm. All insets provide a close-up view of PLA signal. PLA index is the number of dots per number of nuclei in n=3 fields of view and in each case the mean±SD is shown; significance was calculated using one-way ANOVA.
Figure 5:
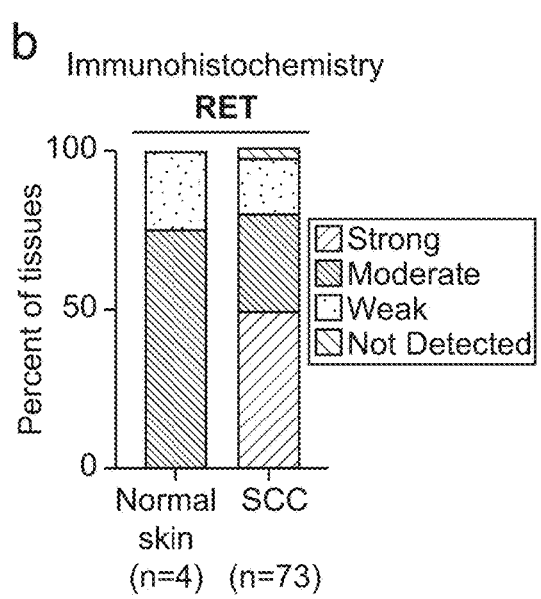
Figure 5:
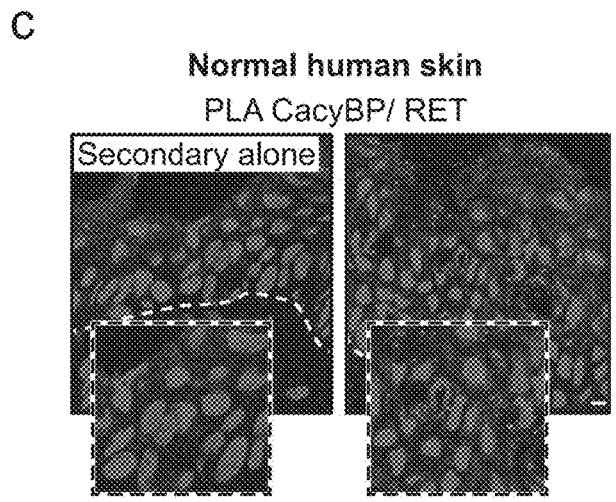
Figure 5:
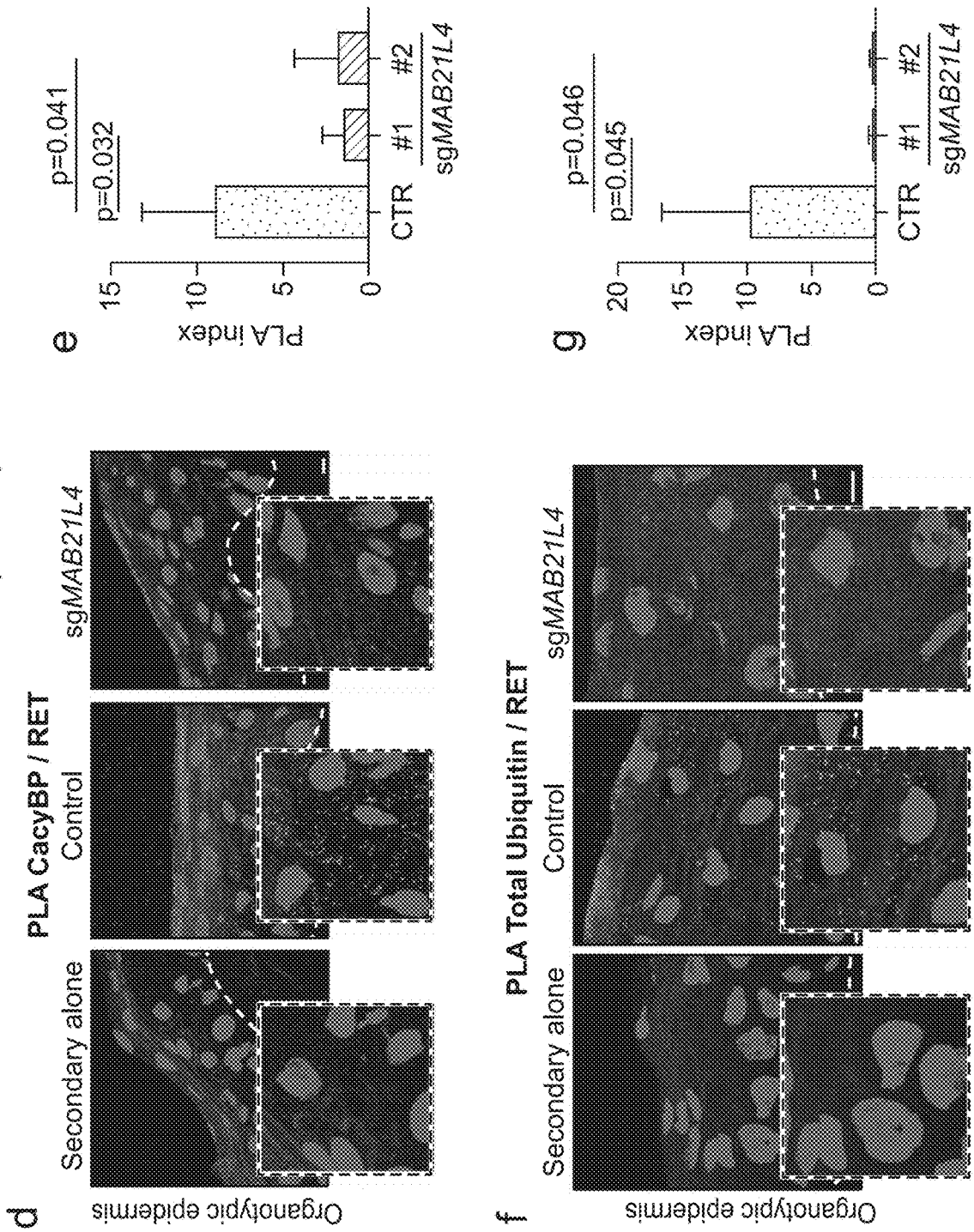
Figure 5:
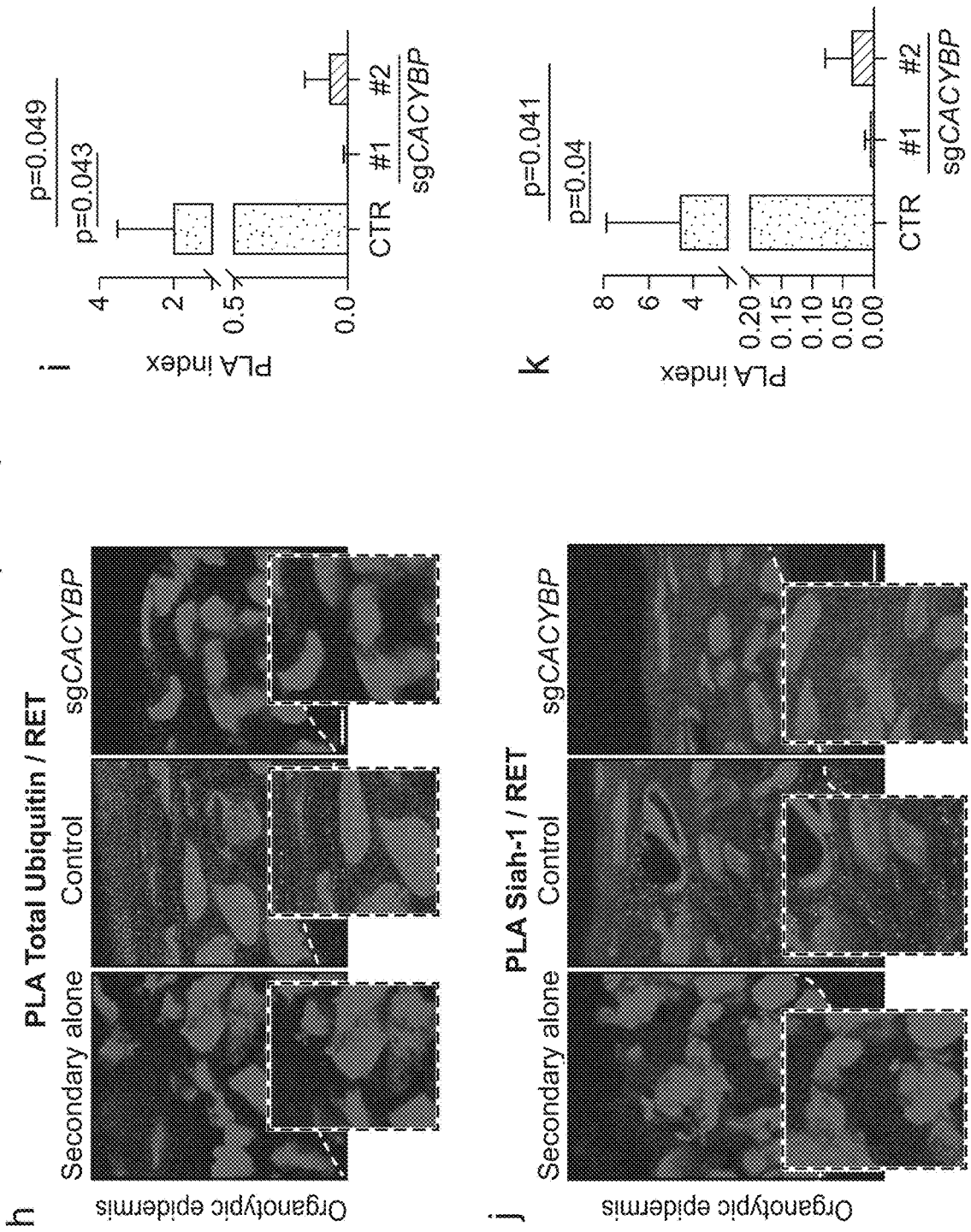

Among the eight genes contained in the intersection of these four datasets was the protooncogene RET, a receptor tyrosine kinase with established cancer relevance (FIG. 5a). Activating mutations in RET are common in medullary thyroid carcinomas and cause multiple endocrine neoplasia type 2, a hereditary cancer syndrome; chromosomal rearrangements involving RET that enable its ligand-independent activation have also been reported in papillary thyroid carcinoma as well as non-small cell lung cancer. While less common, aberrant RET activation may also result from overexpression of the wild type protein, such as occurs in breast cancer as well as head and neck SCC. In the skin, RET fusions have been reported at low frequencies in spitzoid melanocytic neoplasms and ret transgenic mice are born with systemic melanosis from which spontaneous melanomas capable of metastasis arise; however, a role for RET in SCC development has not previously been described.

Figure 11:
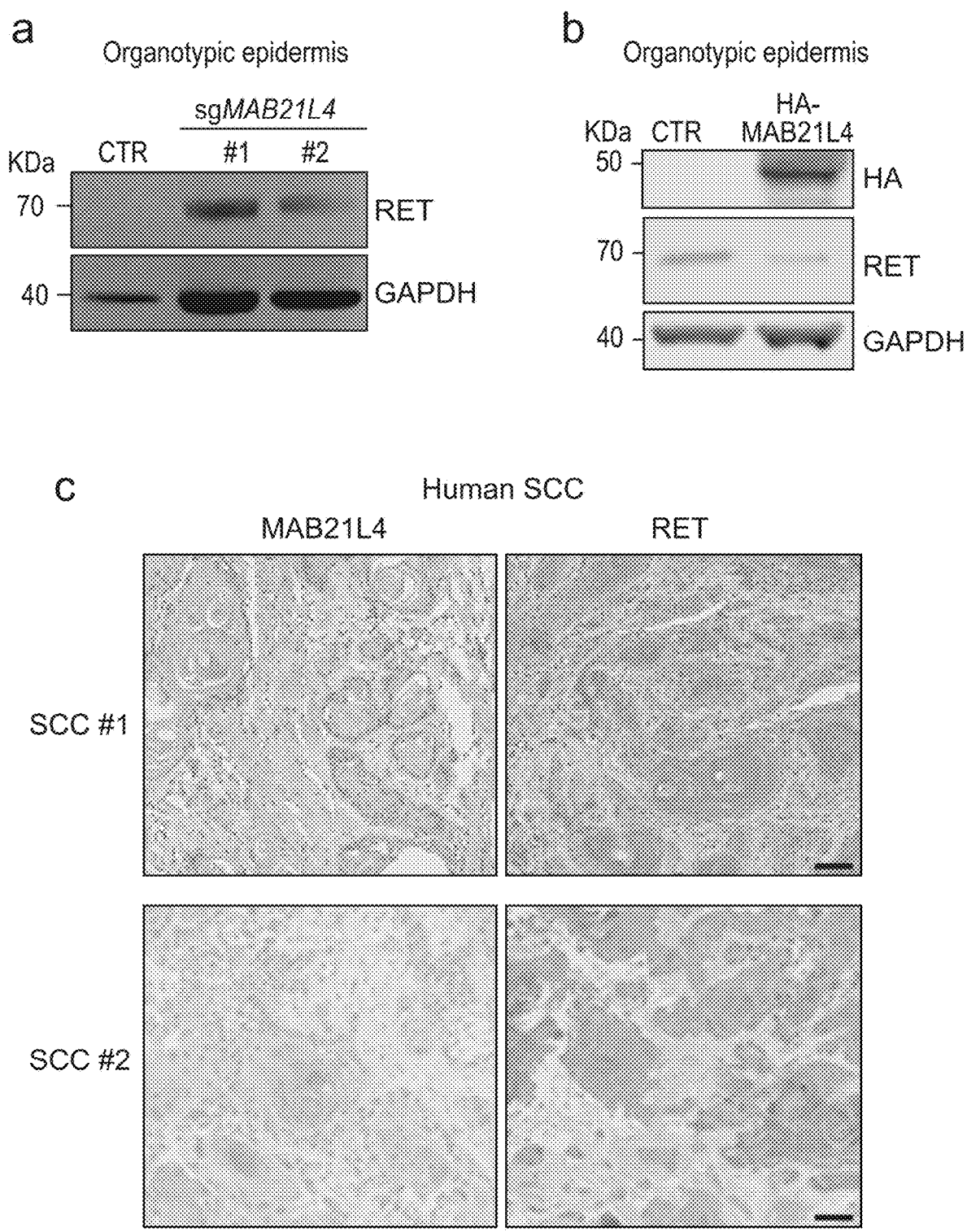
FIG. 11. MAB21L4 controls RET expression in human epidermis and SCC (a) Western blot analysis of RET expression in organotypic epidermis generated from MAB21L4-ablated human primary keratinocytes via two independent sgRNAs (sgMAB21L4) compared to a non-targeting control sgRNA (CTR). Data shown represent n=2 pooled technical replicates. (b) Western blot analysis of RET and HA expression in organotypic epidermis generated from human primary keratinocytes transduced to express HA-MAB21L4 or an empty vector (CTR). Data shown represent n=2 pooled technical replicates. (c) Representative images of MAB21L4 and RET expression strength in SCC tissues. Scale bar, 50 µm. (d) Quantitation of CacyBP expression in normal skin and SCC. (e) PLA of endogenous MAB21L4 and RET in normal human adult skin. (f) Western blot analysis of RET co-immunoprecipitation of empty vector (CTR) or HA-MAB21L4 with endogenous ubiquitin in human HEK 293T cells. Arrowheads indicate a band of identical molecular weight present in both the ubiquitin and RET Western blots. (g) Western blot analysis of RET expression in human skin organoids grown for 3 days on dermis and treated with MG132 (20 µM) or vehicle only (DMSO) for 12 hrs. Data represent n=2 pooled technical replicates. (h) Densitometric analysis of protein expression in (g).
Figure 11:
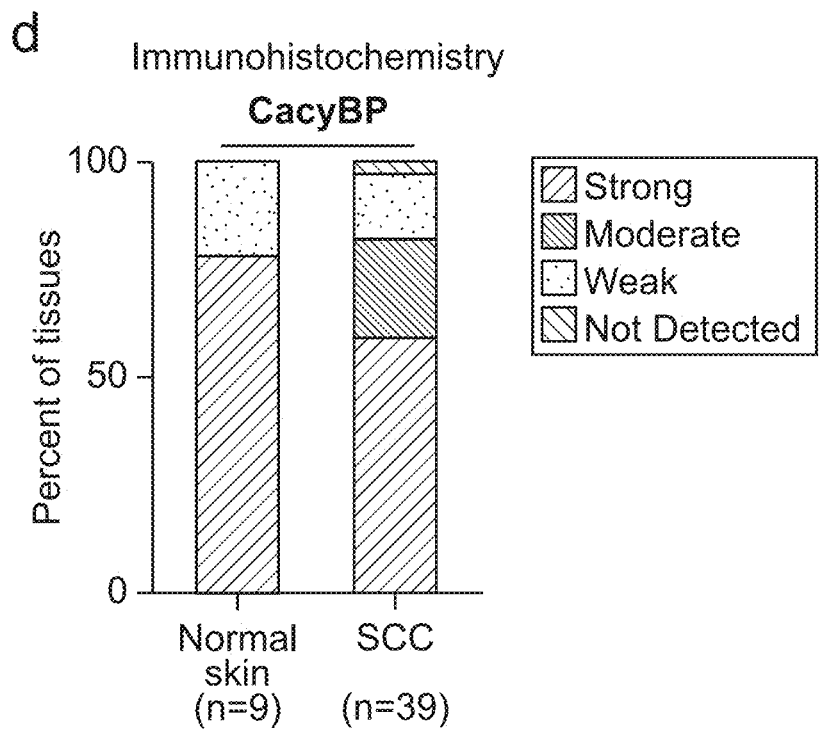
Figure 11:
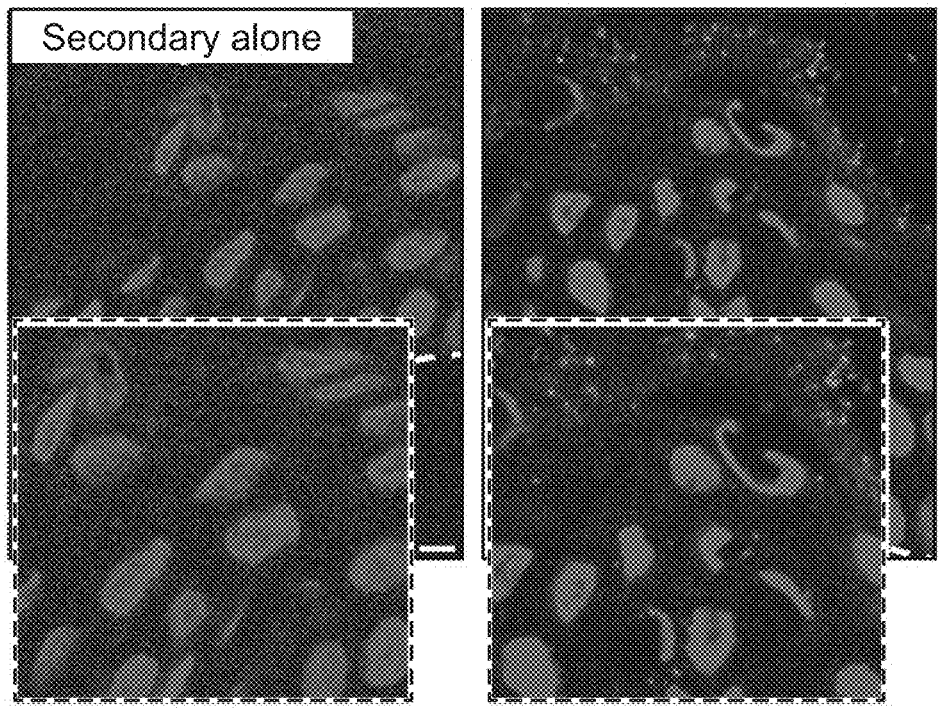
Figure 11:
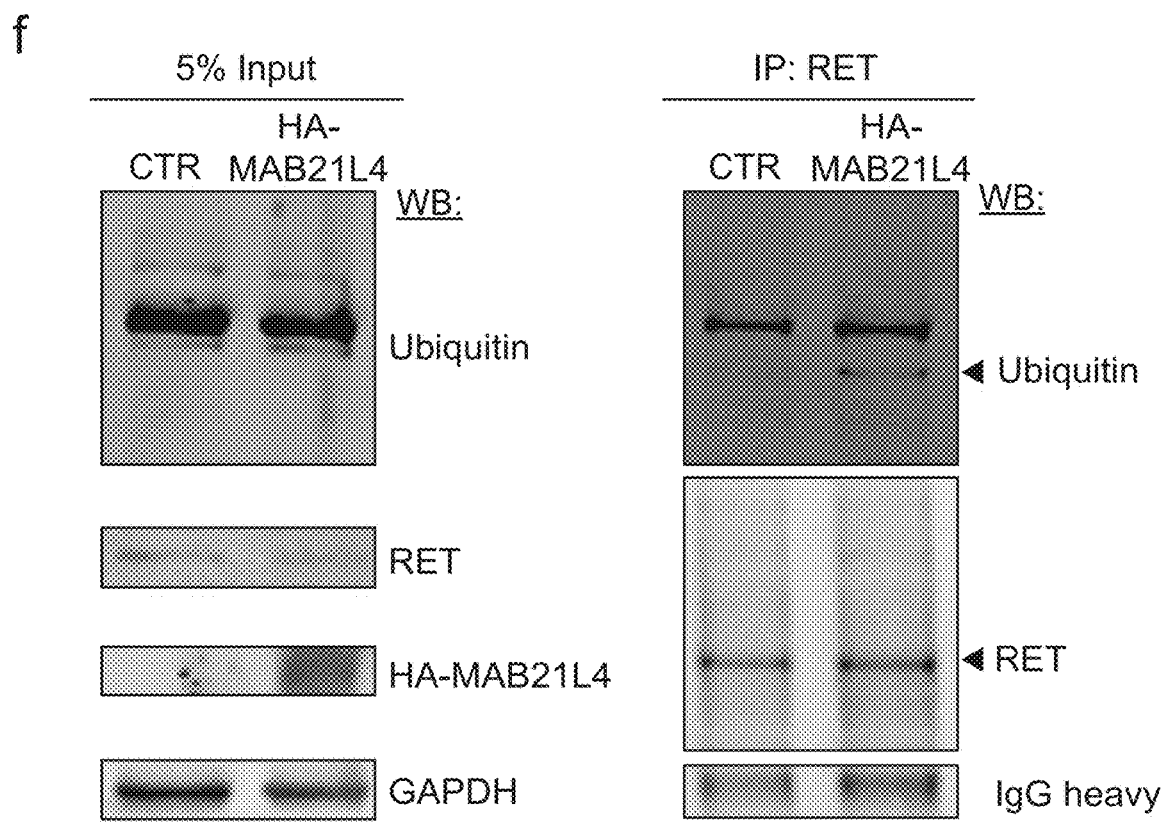

We first assessed RET expression in human skin organoids generated from MAB21L4-ablated primary keratinocytes as well as from cells transduced to overexpress MAB21L4 and confirmed our differential expression analysis of RNA-Seq data in each case (FIG. 11a,b). To further support our RNA-Seq analysis, we next investigated RET expression in SCC by immunohistochemistry and observed frequent upregulation in this setting (FIG. 5b). Interestingly, expression of MAB21L4 and RET were often inversely correlated within a given SCC (FIG. 11c); 51 of 58 (87.9%) SCC noted to have strong or moderate expression of RET had weak or no detectable expression of MAB21L4. These data suggest that loss of MAB21L4 leads to overexpression of wild type RET and might enable SCC development.

Our earlier observation that MAB21L4 binds CacyBP to regulate epidermal differentiation prompted us to consider the role of this interaction in malignancy. Importantly, we did not detect a significant change in the expression of CacyBP in SCC by immunohistochemistry (FIG. 11d), which encouraged us to examine its localization instead. We first confirmed CacyBP-RET as well as MAB21L4-RET proximity in normal adult skin by PLA analysis (FIG. 5c and FIG. 11e). Loss of MAB21L4 by CRISPR/Cas9 genetic disruption with two independent sgRNAs in organotypic human epidermis significantly diminished the PLA signal of CacyBP and RET (FIG. 5d,e). These results are consistent with a model whereby MAB21L4 functions as a scaffold protein that binds CacyBP and brings it into proximity of RET. CacyBP has notably been shown to interact with and bridge the E3 ubiquitin ligase Siah-1 to the adaptor Skp1, an essential component of Skp1-Cullin-F-Box protein (SCF) complexes; these interactions contribute to ubiquitination and degradation of β-catenin in response to genotoxic stressors that induce p53.

Given the proximity of CacyBP and RET, we wondered whether RET stability in the skin might be regulated by ubiquitination. Fluorescent PLA signal generated by RET and ubiquitin proximity was abolished in MAB21L4-ablated epidermis using two independent sgRNAs (FIG. 5f,g). A similar reduction in RET-ubiquitin PLA signal was observed in CacyBP-deficient epidermis (FIG. 5h,i) as well as disrupted proximity between Siah-1 and RET (FIG. 5j,k). Conversely, RET immunoprecipitated from human cells that overexpress MAB21L4 exhibited increased ubiquitination compared to cells transfected with a control plasmid (FIG. 11f). Treatment of normal skin organoids with the proteasome inhibitor MG132 resulted in RET accumulation (FIG. 11g,h), consistent with results obtained in thyroid medullary carcinoma cells. Taken together, these data suggest that MAB21L4-CacyBP interaction is required for RET ubiquitination by Siah1, which targets RET for proteasome-mediated degradation. Loss of MAB21L4, such as occurs in cancer, would stabilize RET by preventing its Siah1-mediated degradation and may explain RET upregulation in SCC.

Figure 6:
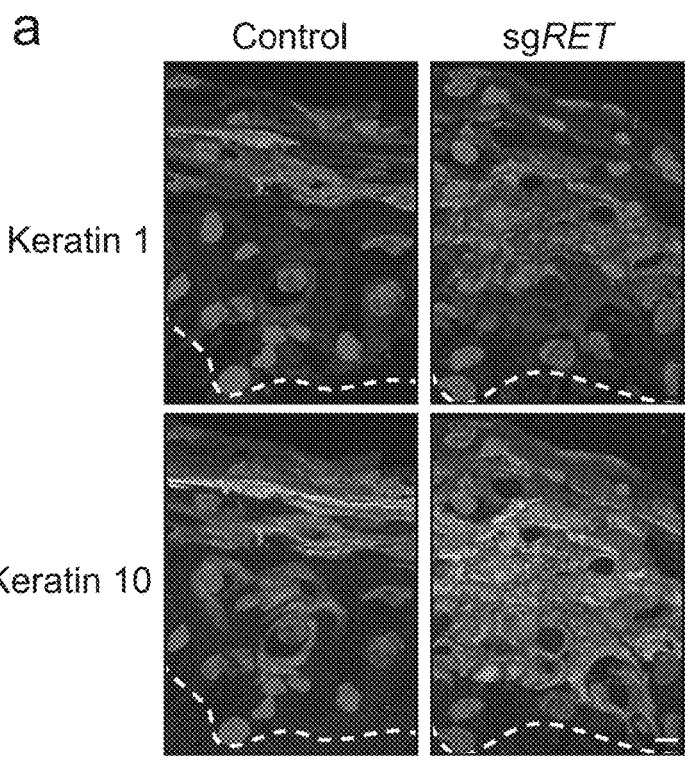
FIG. 6. Loss of RET potentiates differentiation and suppresses neoplastic invasion (a) Expression of differentiation proteins in RET-ablated (sgRET) human skin organoids generated by CRISPR/Cas9-mediated genetic disruption compared to a non-targeting control after 3 days of growth on dermis; differentiation proteins detected by immunofluorescence in red (keratin 1) and green (keratin 10), dotted line indicates basement membrane zone. Scale bar, 10 ⌈m. (b) Differentiation gene mRNA quantitation in human skin organoids generated using two independent RET sgRNAs compared to control sgRNA and after 3 days of growth on dermis. Bars represent mean±SD, three technical replicates per experiment. (c) Keratin 5 (red) and collagen VII (green) immunofluorescence of oncogenic Ras-transformed human skin organoids generated from CRISPR/Cas9 MAB21L4-ablated human primary keratinocytes (sgMAB21L4) or control sgRNA after 7 days of growth on dermis; tissue was regenerated in the presence or absence of BLU-667, a highly selective RET inhibitor. Data representative of n=3 technical replicates. Scale bar, 10 µm. (d) Quantitation of invasion index in (c) with two independent MAB21L4 sgRNAs, calculated as the integrated density of keratin 5 staining beneath the basement membrane divided by the length of the basement membrane in n=4 fields of view. The invasion index of each field is shown along with the mean±SD; significance was calculated using one-way ANOVA. (e) Keratin 5 (red) and collagen VII (green) immunofluorescence of oncogenic Ras-transformed human skin organoids after 7 or 14 days of growth on dermis; BLU-667 was initiated on day 7. Data representative of n=3 technical replicates. Scale bar, 50 µm. (f) Quantitation of invasion index in (e), calculated as the integrated density of keratin 5 staining beneath the basement membrane divided by the length of the basement membrane in n=3 fields of view. The invasion index of each field is shown along with the mean±SD; significance was calculated using one-way ANOVA. (g) Quantitation of invasion depth in (e), measured as the depth of the tumor front below the basement membrane in n=7 fields of view. The invasion depth of each field is shown along with the mean±SD; significance was calculated using a two-tailed t-test.
Figure 6:
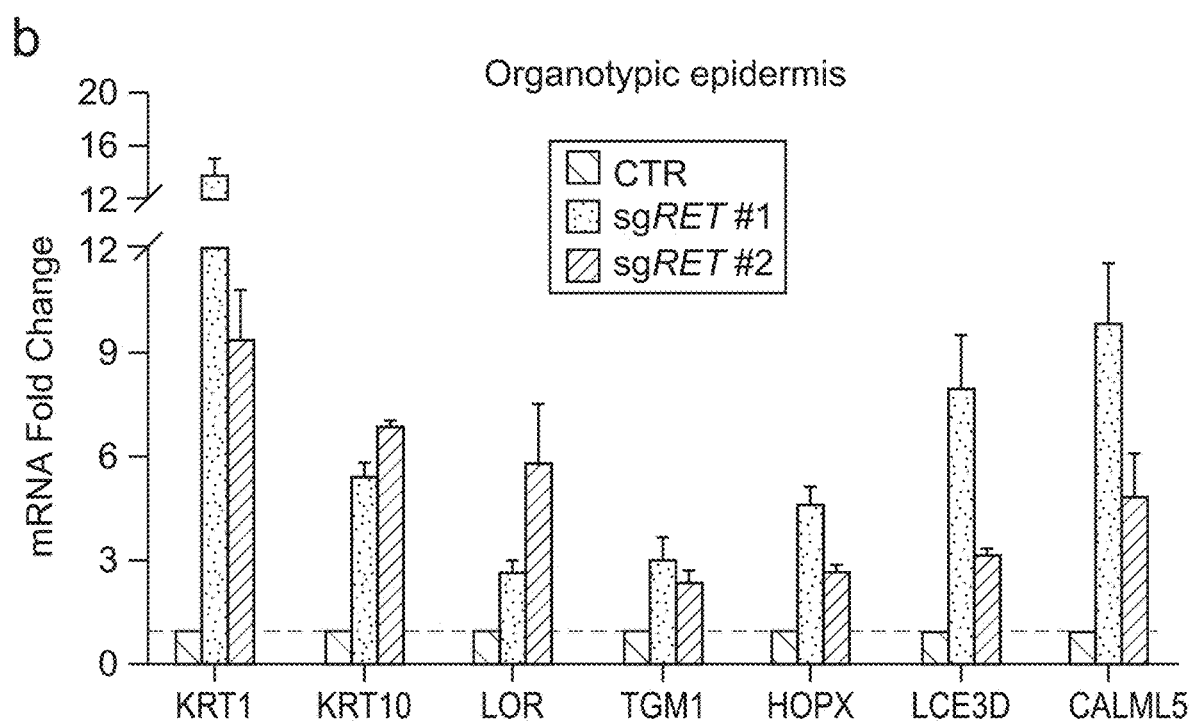
Figure 6:
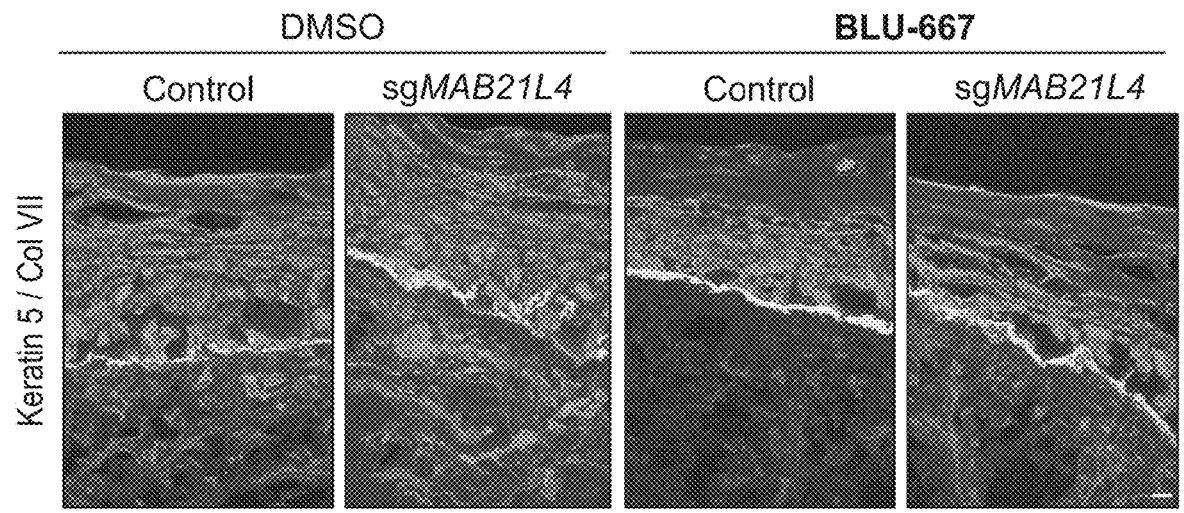
Figure 6:
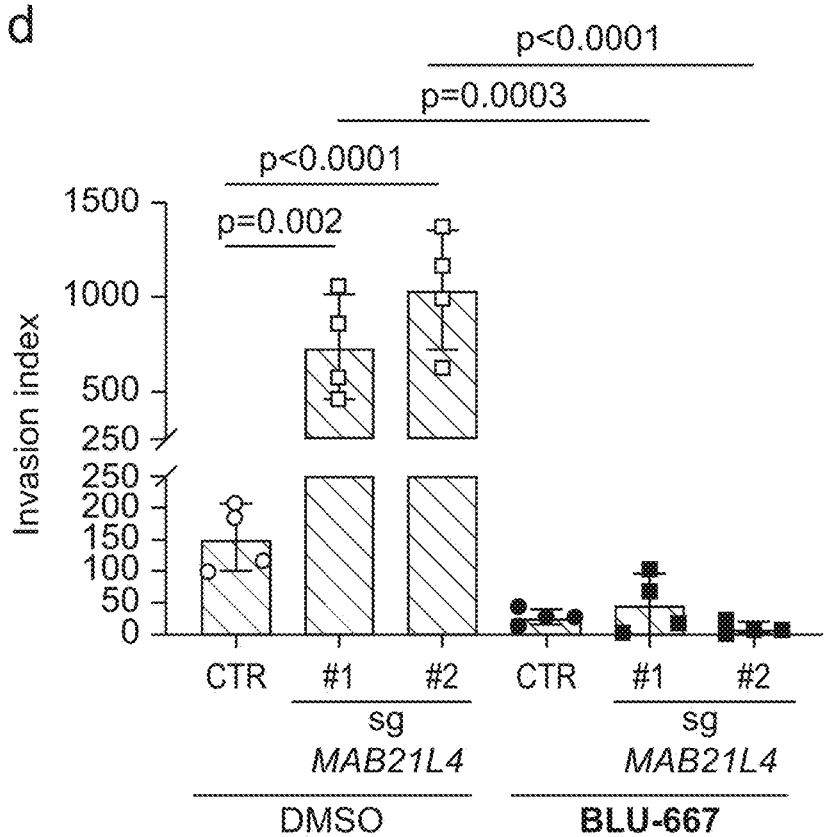
Figure 6:
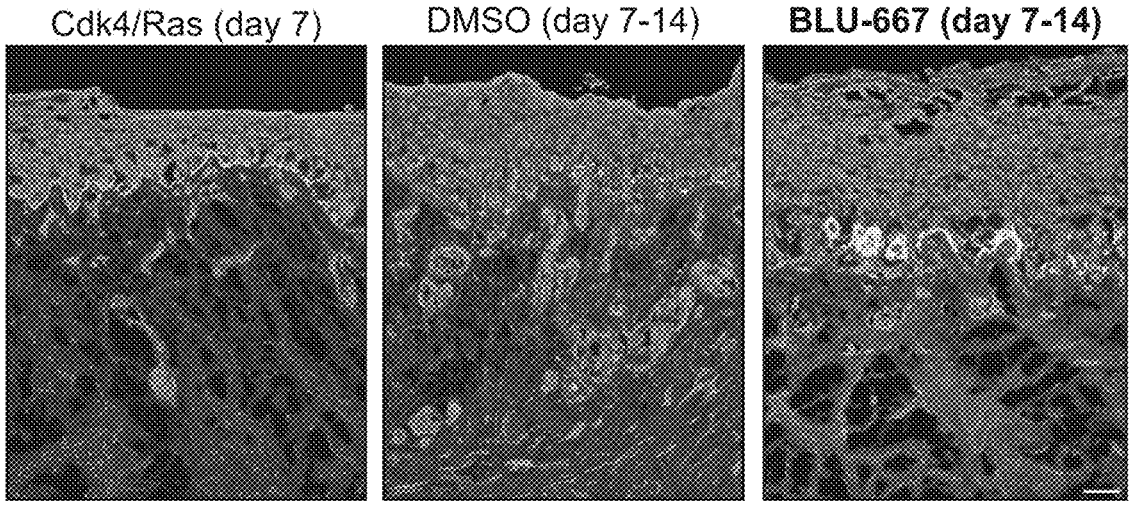
Figure 6:
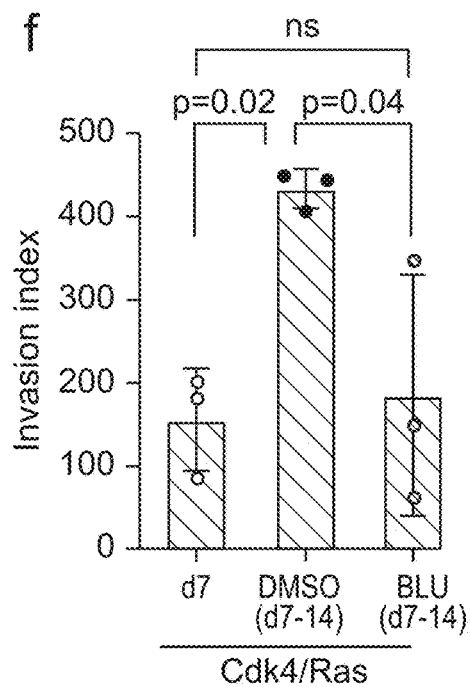
Figure 6:
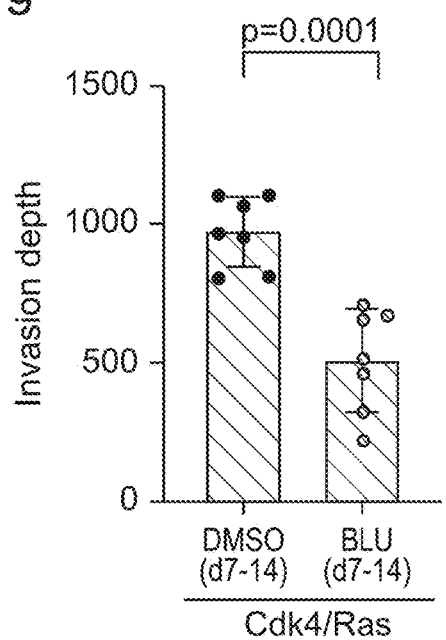
Figure 12:
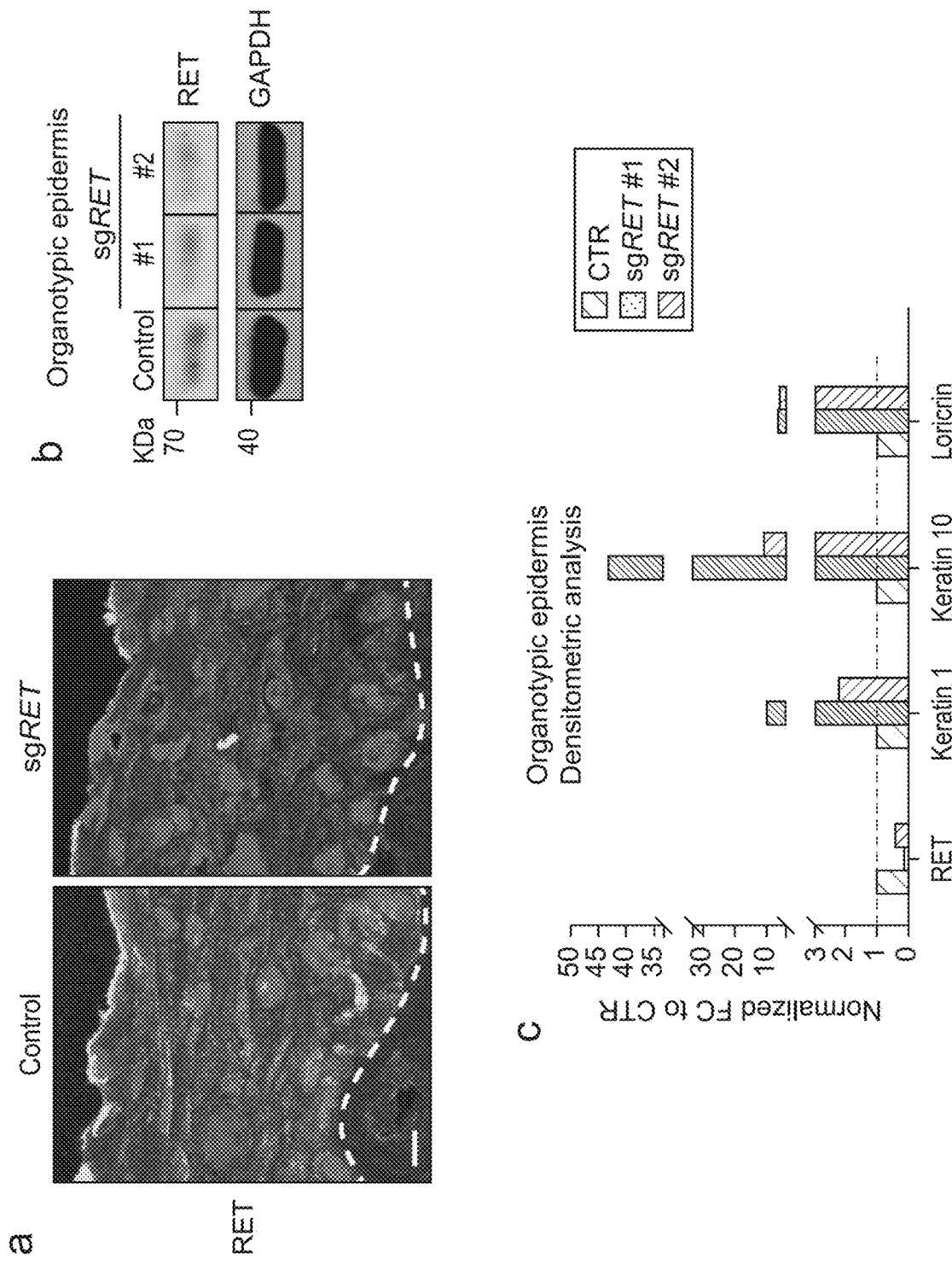
FIG. 12. Loss of RET potentiates differentiation in human epidermal tissue (a) Immunofluorescence analysis of RET expression in human skin organoids generated from RET-ablated human primary keratinocytes (sgRET) compared to a non-targeting control sgRNA and grown for 3 days on dermis. Data are representative of n=2 technical replicates. Scale bar, 10 µm. (b) Western blot analysis of RET expression in human skin organoids grown for 3 days on dermis. Data are representative of n=2 biological replicates. (c) Densitometric analysis of protein expression in human skin organoids generated from RET-ablated human primary keratinocytes via two independent sgRNAs (sgRET) compared to a non-targeting control 38 sgRNA (CTR) and grown for 3 days on dermis. Data are representative of n=2 biological replicates.

Loss of RET potentiates differentiation and suppresses neoplastic invasion. RET signaling is vital to early development; knockout studies in mice have demonstrated effects on kidney organogenesis, gut innervation, and germ cell survival in the developing male testis. However, RET inactivation has not been studied in human skin. To investigate its role in this context, we disrupted RET using two independent sgRNAs to create pools of gene targeted primary keratinocytes and placed these cells onto dermis to generate human skin organoids (FIG. 12a,b). RET depletion had the opposite effect of MAB21L4 or CacyBP loss and resulted in increased expression of differentiation markers without affecting epidermal stratification (FIG. 6a,b and FIG. 12c). These results are consistent with recent data in *Drosophila* demonstrating Ret expression in adult intestinal epithelial progenitor cells, but not their differentiated counterparts.

Taken together, our data demonstrate that RET is involved in maintaining keratinocytes in an undifferentiated state; normal differentiation requires endogenous levels of RET and can be enhanced by reducing RET expression intrinsically below wild type levels.

As loss of differentiation may be coupled to other cancer-enabling behaviors, we next considered the therapeutic implications of aberrant RET activation in SCC. The investigational RET inhibitor BLU-667 (pralsetinib) targets cancer cells with activating RET mutations as well as fusions and has demonstrated clinical activity in RET-altered solid tumors. We first generated non-transformed human skin organoids and subjected them to treatment with BLU-667 to confirm suppression of RET signaling, as measured by a reduction in RET phosphorylation at Y1062 (FIG. 13a,b).

Figure 13:
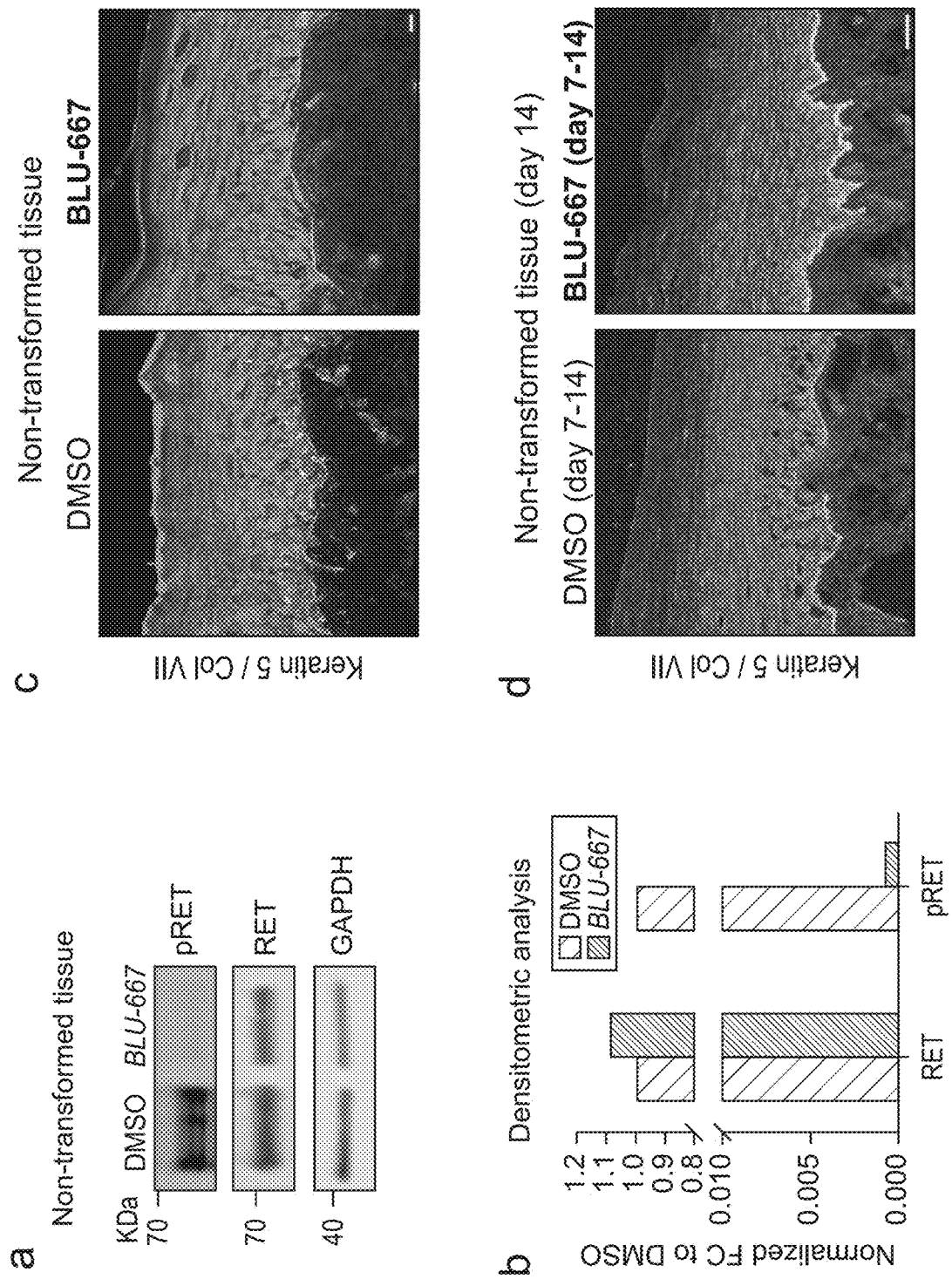
FIG. 13. Impact of BLU-667 on human epidermal tissue (a) Western blot analysis of RET and phospho-RET expression in human skin organoids grown for 7 days on dermis in the presence or absence of BLU-667 (15 nM). Data are representative of n=2 independent experiments. (b) Densitometric analysis of (a). (c) Immunofluorescence of keratin 5 (red) and collagen VII (green) of organotypic human epidermis regenerated in the presence of BLU-667 (15 nM) vs vehicle (DMSO) and grown for 7 days on dermis. Data shown are representative of n=2 independent experiments, each with 2 technical replicates. Scale bar, 10 µm. (d) Immunofluorescence of keratin 5 (red) and collagen VII (green) of organotypic human epidermis after 14 days of growth on dermis, with BLU-667 (15 nM) or vehicle (DMSO) initiated on day 7. Data shown are representative of n=2 technical replicates. Scale bar, 50 µm. 39

Organoids cultured in the continuous presence of BLU-667 did not differ substantially from vehicle controls in stratification and epidermal thickness, suggesting that RET inhibition does not result in tissue collapse or altered viability (FIG. 13c). We next used MAB21L4-intact or MAB21L4-ablated primary human keratinocytes to generate skin organoids programmed to undergo invasive neoplasia by oncogenic Ras and Cdk4. These neoplastic tissues were maintained in culture medium containing BLU-667 to investigate the contribution of RET to SCC development. Treatment with BLU-667 prevented basement membrane degradation and suppressed invasion accelerated by MAB21L4 loss (FIG. 6c,d).

These data implicate the MAB21L4-RET axis in epidermal neoplasia and prompted us to examine the effectiveness of BLU-667 on established invasion. To test this, we assessed neoplastic invasion in human skin organoids with BLU-667 added to the culture medium after early malignant transformation occurred. We first confirmed that late-onset BLU-667 treatment did not adversely affect epidermal stratification and thickness compared to vehicle controls (FIG. 13d). Human skin tissues undergoing malignant transformation by enforced expression of oncogenic Ras and Cdk4 were then subjected to BLU-667 treatment following the onset of early neoplastic invasion.

Inhibition of RET signaling by BLU-667 suppressed further migration of keratinocytes compared to vehicle controls; we observed both fewer keratinocytes below the basement membrane as well as a reduction in tumor infiltration depth (FIG. 6e-g). Taken together, these results indicate an underappreciated role for RET in SCC development and progression and provide a clinical indication for RET inhibitors in skin cancer.

In this study, a transcriptome-wide screen for uncharacterized ORFs with reciprocal patterns of expression in skin differentiation and SCC was followed by loss- and gain-of-function studies in human skin organoids to reveal MAB21L4 as a regulator of epidermal homeostasis that functions as a tumor suppressor in the skin. MAB21L4 expression is frequently downregulated in our analyses of human SCC as well as precancerous AK and subject to somatic deletion in other TCGA tumor types.

Figure 7:
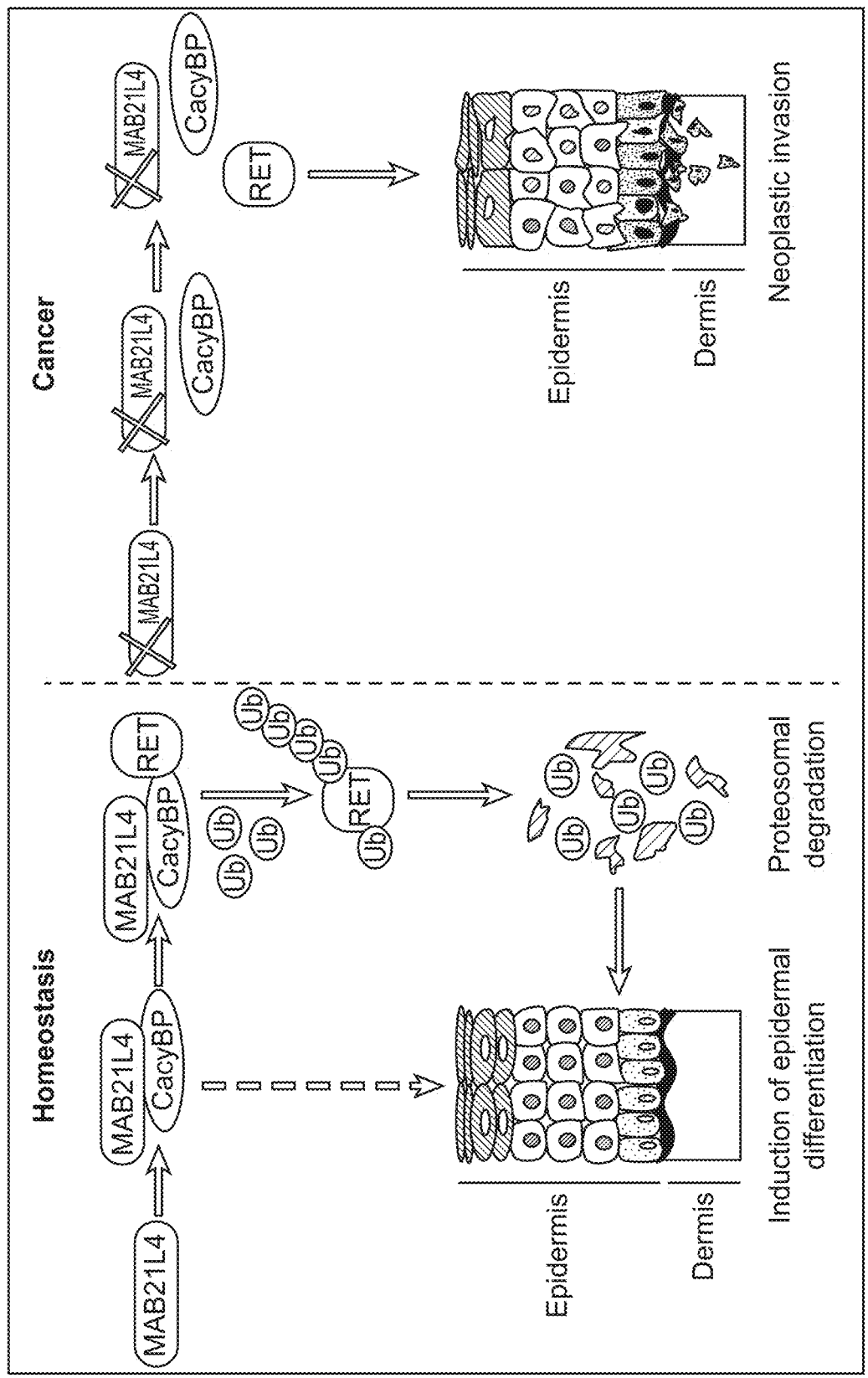
FIG. 7. MAB21L4-CacyBP interaction controls RET stability and is disrupted in cancer 20 Proposed model of MAB21L4-dependent regulation of RET stability in epidermal differentiation and neoplasia.

Proximity proteomics in living skin organoids suggests that MAB21L4-dependent control of epidermal differentiation is mediated by the physical proximity of MAB21L4 to CacyBP, a molecular bridge in ubiquitin E3 complexes. This interaction is required for CacyBP proximity to the RET proto-oncogene and controls RET stability through Siah1-mediated ubiquitination and proteasomal degradation (FIG. 7). While CacyBP is upregulated in differentiating H9c2 rat cardiomyoblasts and NB2a mouse neuroblastoma cells, a role in epidermal differentiation has not been described. Our findings indicate that MAB21L4-CacyBP proximity is required for full engagement of the terminal differentiation gene expression program in the skin. CacyBP is known to regulate ubiquitination and proteasomal degradation of β-catenin through interaction with Siah-1 and Skp1; our analyses suggest that CacyBP may control RET stability in a similar manner. Recent data also indicate CacyBP may promote autophagy through interaction with the ubiquitin ligase Nrdp1 and the inhibitor of apoptosis protein BRUCE. These studies are intriguing given the role of autophagic degradation in epidermal development and differentiation.

Our findings demonstrate that a physical proximity relationship between MAB21L4 and CacyBP is critical to RET-mediated epidermal differentiation and neoplastic invasion. Interplay between other mab-21 proteins and RET may also exist.

Our data indicate that RET ablation enhances the terminal differentiation gene expression program in the skin and highlight a role for RET in maintaining the undifferentiated cell state in the epidermis. BLU-667's effectiveness in SCC may be a result of returning inappropriately high expression of activated RET to endogenous levels, thus reenabling differentiation. Increased expression of RET, as seen in SCC, is further known to engage integrin signaling and promote cell migration. Our discovery that selective pharmacologic inhibition of RET suppresses keratinocyte invasion in human skin tissues undergoing malignant transformation supports the effectiveness of β1 integrin blockade in attenuating Ras-driven human epidermal neoplasia mimicking SCC.

Perineural invasion is characterized histologically by tumor invasion and growth along nerves; like many other cancers, its presence in SCC is associated with aggressive tumor behavior and an increased risk of death. The glial cell-derived neurotrophic factor (GDNF) family of ligands (GFLs), when complexed together with GDNF Family Receptors α (GFRα1-4), enable activation of RET signaling by binding to RET and inducing its phosphorylation at specific tyrosine residues. Perineural invasion may be the result of a chemotactic gradient formed by GFLs and soluble forms of GFRα1 secreted by neurons and nerve-supporting cells that encourages RET expressing tumor cells to migrate away from their tissue of origin and towards the central nervous system. Our data showing MAB21L4-RET interaction in human epidermal neoplasia represent a tumor cell-intrinsic relationship that impacts perineural invasion and as such, targeting RET dependency in SCC can improve clinical outcomes in patients whose tumors exhibit this adverse growth pattern.

In summary, this work presents the first characterization of MAB21L4 function, highlights a previously unrecognized contribution of RET to epidermal differentiation as well as the development of keratinocyte cancers, and the clinical use of selective RET inhibitors in SCC and precancerous AK. These and related compounds, particularly those that can be delivered to the skin topically, are a valuable addition to existing treatment options for SCC and its precursor lesions.

Materials and Methods

Human Tissue Samples All human tissues were studied under an IRB-approved protocol and all patients provided written informed consent. All samples were validated by histological analysis.

Cell Culture Primary human keratinocytes were isolated from freshly discarded skin surgical specimens and cultured in a 1:1 mixture of Keratinocyte-SFM (Life Technologies 17005-142) and Medium 154 (Life Technologies M-154-500) supplemented with bovine pituitary extract (BPE), epidermal growth factor (EGF), and human keratinocyte growth supplement (HKGS). Cells were maintained at 37° C. in 5% $CO_2$. Keratinocyte differentiation was induced in vitro by growing the cells at full confluence with 1.2 mM calcium added to the culture medium for up to 6 days. Primary human fibroblasts isolated from freshly discarded skin samples and HEK-293T cells were grown at 37° C. in 5% $CO_2$ in DMEM medium (GIBCO) supplemented with 10% FBS.

Human Skin Organoids and Skin Xenografts Generation of human skin organoids was performed as previously described. Briefly, $1 \times 10^6$ keratinocytes were seeded onto a 1 cm² section of devitalized human dermis and cultured at the air-liquid interface for up to 6 days for differentiation studies. To generate organotypic invasive epidermal neoplasia, devitalized human dermis was populated with human primary fibroblasts at least 1 week prior to keratinocyte seeding. Keratinocytes were transduced with oncogenic HRas as well as Cdk4 and seeded onto fibroblast-containing dermis. Neoplastic tissues were harvested for analysis up to 14 days post-seeding.

For xenograft studies, organotypic invasive epidermal neoplastic tissues were first generated as above. After 5 days of growth at the air-liquid interface, tissues were grafted onto the dorsal backs of 6-week old female hairless SCID mice (Charles River, SHO, strain code 474), then wrapped with petroleum-impregnated gauze followed by application of Tegaderm and Coban dressings (3M). Xenografts were unwrapped 7 days after initial grafting. All animal studies were performed under an IACUC-approved protocol.

Lentiviral Transduction Lenti-X 293T cells were transfected with FLAG-HA-6×HIS (FHH)-tagged MAB21L4 or an empty FHH vector along with the helper plasmids pCMV-dR8.91 and pUC-MDG to generate lentiviral medium. Human primary keratinocytes were transduced with FHH-MAB21L4 or FHH only with 5 µg/ml polybrene. Two days post-transduction, keratinocytes were trypsinized and plated in a larger culture flask in growth medium supplemented with 1 µg/ml puromycin. Cells were selected in puromycin for 2 days or until mock-transduced control cells were completely eradicated.

Retro viral Transduction Phoenix cells were transfected with plasmids containing the cDNA sequences of CDK4 or HRAS to generate retroviral medium. Human primary keratinocytes were transduced with retroviral medium supplemented with 5 µg/ml polybrene by centrifugation at 1000 rpm for 1 hour at room temperature. The retroviral medium was replaced with fresh growth medium immediately after centrifugation and cells were returned to 37° C. in 5% CO2.

CRISPR/Cas9 Gene Ablation Potential sgRNA sequences predicted to have high sensitivity as well as specificity were generated using a CRISPR design tool and cloned into the pLentiGuide plasmid. Concentrated lentiviral medium was generated for each sgRNA as well as Cas9 using the pLex_Cas9 plasmid65 as described above. For gene ablation studies, human primary keratinocytes from two different donors were pooled and transduced with Cas9 lentiviral medium. Two days post-transduction, the cells were trypsinized and plated in a larger culture flask in growth medium supplemented with 2 µg/ml blasticidin. Cells were selected in blasticidin for 2 days and then re-seeded and transduced with sgRNA lentiviral medium. Two days post sgRNA transduction, the cells underwent selection in growth medium supplemented with 1 µg/ml puromycin. For the CACYBP-ablation studies depicted in FIGS. 3d-g, keratinocytes immortalized by retroviral transduction with the pLXSN16 plasmid encoding the HPV E6 and E7 proteins served as the starting epithelial cell pool.

The following sgRNA sequences were used: Control (GACCGGAACGATCTCGCGTA) (SEQ ID NO: 1); MAB21L4 sg1 (GCAGCACGTTCTCTGCGCGC) (SEQ ID NO: 2); MAB21L4 sg2 (GAGTAGTCCACGAT-GAAGCGG) (SEQ ID NO: 3); CACYBP sg1 (TTATCTGACTGATCCCATCC) (SEQ ID NO: 4); CACYBP sg2 (ACTTACCTCTTCTGAAGCCA) (SEQ ID NO: 5); RET sg1 (TCCTCGTCGTACACGGTCAC) (SEQ ID NO: 6); RET sg2 (TGGCGTACTCCACGATGAGG) (SEQ ID NO: 7).

Proximity Proteomics in Human Skin Organoids A triple hemagluttinin (3×HA) tag and BASU biotin ligase34 were fused to the MAB21L4 protein in the pLEX vector. Primary human keratinocytes were transduced with 3×HA-BASU-MAB21L4 or 3×HA-BASU lentiviral medium as described above. Following selection in growth medium supplemented with 1 µg/ml puromycin, 1×10⁶ keratinocytes were seeded onto a 1 cm² section of devitalized human dermis and cultured in KGM (keratinocyte growth medium) at the air-liquid interface for 5 days. On day 6 post-seeding, proximal proteins were labeled by adding 50 µM biotin to the growth medium for 16 hours. The epidermis from each tissue was separated from the dermis, minced with a scalpel, rinsed in PBS to remove biotin-containing growth medium, lysed in high-SDS RIPA buffer (Pierce), and then sonicated using a Bioruptor (Diagenode). The cell lysates were then centrifuged through Microsep columns (Pall) to deplete free biotin and then incubated with Dynabeads MyOne Streptavidin C1 beads (Thermo Fisher) at 4° C. under rotation overnight (~16 h). Affinity purification was performed as previously described and proteins were analyzed by LC-MS/MS using a Proxeon EASY nanoLC system (Thermo Fisher Scientific) coupled to an Orbitrap Elite mass spectrometer (Thermo Fisher Scientific).

All mass spectra were analyzed with MaxQuant software version 1.5.5.1. MS/MS spectra were searched against the Homo sapiens Uniprot protein sequence database (version January 2017) and GPM cRAP sequences (commonly known protein contaminants). Precursor mass tolerance was set to 20 ppm and 4.5 ppm for the first search where initial mass recalibration was completed and for the main search, respectively. Product ions were searched with a mass tolerance 0.5 Da. The maximum precursor ion charge state used for searching was 7. Carbamidomethylation of cysteines was searched as a fixed modification, while oxidation of methionines and acetylation of protein N-terminal were searched as variable modifications. Enzyme was set to trypsin in a specific mode and a maximum of two missed cleavages was allowed for searching. The target-decoy-based false discovery rate (FDR) filter for spectrum and protein identification was set to 1%. Mass spectrometry proteomics data was analyzed for interactor candidates with SAINTq, using a SAINT probability score>0.867. Proteins were required to include at least one uniquely mapping peptide. Proteins that appeared in fewer than 60 out of 80 BioID experiments in the CRAPome, a database of negative controls and background contaminants, was used to further prioritize proteins.

RNA-seq of Human Skin Organoids To extract RNA from human skin organoids, tissues were minced with a scalpel and then subjected to homogenization in RLT Plus buffer (Qiagen) with β-mercaptoethanol added in Lysing Matrix D tubes (MP Biomedicals) using a FastPrep homogenizer (MP Biomedicals). RNA extraction was otherwise performed using the RNeasy Plus Mini Kit (Qiagen) according to the manufacturer's instructions. RNA integrity was verified using the RNA 6000 Nano Kit (Agilent) in combination with the 2100 Bioanalyzer (Agilent). mRNA libraries (polyA) were prepared and sequenced on the HiSeq 2500 (Illumina) with a target of 25 million mapped reads per sample. FASTQ data were aligned to the transcriptome using STAR version 2.5.4b and count data were generated with RSEM version 1.3.170 against the human genome assembly GRCh38. Differential gene expression analysis was performed using DESeq2 with a false-discovery rate (FDR) threshold of 0.171.

Quantitative RT-PCR RNA was extracted using the RNeasy Plus Mini Kit (Qiagen) according to the manufacturer's instructions and reverse transcribed to cDNA using iScript reverse transcriptase per the manufacturer's protocol (Bio-Rad). Quantitative PCR was performed on a Roche LightCycler 480 II using the SYBR green kit (Fisher Scientific). The cycling parameters were: 94° C. for 10 seconds, 60° C. for 10 seconds, 72° C. for 10 seconds, for a total of 45 cycles. Gene expression was quantified relative to the housekeeping genes RPL32 or GAPDH using the 2−ΔΔCt method 72.

Western Blotting Cells and organoids were both lysed in RIPA buffer (Thermo Fisher Scientific) supplemented with phosphatase inhibitor and protease inhibitor cocktails (Sigma-Aldrich). For human skin organoids, the epidermis was separated from the dermis, immersed in RIPA buffer, and subjected to 4 cycles of disruption using the gentleMACS Dissociator (Miltenyi Biotec). The primary antibodies used were: MAB21L4 (1:500, Abcam, ab185350); ®-actin (1:1000, Sigma-Aldrich, A1978), HA (1:1000, Cell Signaling, 3724S), HA (1:1000, BioLegend, 901501), CacyBP (1:500, Proteintech, 11745-1-AP), GAPDH (1:1000, Millipore, MAB374), GAPDH (1:1000, Cell Signaling, 2118), Cdk4 (1:1000, Santa Cruz Biotechnology, sc-749), H-Ras (1:500, Santa Cruz Biotechnology, sc-520), RET (1:500, NSJ Bioreagents, F53523), p-RET (phospho-Y1062) (1:100, Biorbyt, orb304551), ubiquitin (1:500, Abcam, ab7780). The secondary antibodies were used at 1:10000 and were: IRDye 680RD goat anti-mouse (LI-COR, 926-68070), IRDye 800CW goat anti-mouse (LI-COR, 926-32210), IRDye 680RD goat anti-rabbit (LI-COR, 926-68071) and IRDye 800CW goat anti-rabbit (LI-COR, 926-32211). Proteins were visualized on a LI-COR Odyssey CLx. For chemiluminescence visualization, the secondary antibodies were: Amersham ECL HRPconjugated donkey anti-rabbit (GE Healthcare, NA934) and Amersham ECL HRP-conjugated sheep anti-mouse (GE Healthcare, NA931). SuperSignal West Dura (Thermo Fisher Scientific) was used for protein visualization.

Immunofluorescence Human skin organoids were embedded in Optimal Cutting Temperature (OCT) compound (Sakura Finetek) and 7 μm tissue sections were mounted onto polylysine slides (Thermo Scientific). Tissue cryosections were fixed in 100% methanol at −20° C. for 10 min and subsequently permeabilized by incubation with 0.1% Triton X-100 (Sigma-Aldrich) in PBS. The tissues were then incubated for 30 minutes at room temperature with blocking buffer (horse serum diluted 1:10 in PBS) and then for 1 hour with primary antibodies diluted in 0.05% Triton X-100 (Sigma-Aldrich) and 1:100 horse serum in PBS. The primary antibodies used were: MAB21L4 (1:50, Biorbyt, orb159238), Collagen Type VII (1:50, Millipore, MAB2500), Keratin 1 (1:500, BioLegend, 905201), Keratin 10 (1:500, Thermo Fisher Scientific, MS611P), CacyBP (1:50, Proteintech, 11745-1-AP), Keratin 5 (1:500, BioLegend, 905501). After 2 washes, the tissues were incubated for 45 minutes with secondary antibodies diluted in 0.05% Triton X-100 (Sigma-Aldrich) and 1:100 horse serum in PBS. The secondary antibodies used were: goat antimouse IgG Alexa Fluor 488 (1: 500, Thermo Fisher Scientific, A-11001) and goat anti-rabbit IgG Alexa Fluor 594 (1:500, Thermo Fisher Scientific, A-11012). The tissues were then mounted with Prolong Gold Antifade Mountant with DAPI (Thermo Fisher Scientific) and imaged using an LSM 880 Airyscan Fast Live Cell inverted confocal microscope (Zeiss).

Images of several zstacks were acquired and the maximum intensity projection image was generated by using the Fiji-ImageJ package. Invasion index was calculated as integrated density of the Keratin 5 staining underneath the basement membrane divided by the length of the basement membrane. Integrated density and basement membrane length were both analyzed using the Fiji-ImageJ package. The invasion depth was calculated as the distance between the basement membrane and the most distant invading cell in each field of view analyzed. The distance between the basement membrane and the most distant invading cell was analyzed in 3 areas of each field of view using the Fiji-ImageJ package and was averaged. Immunohistochemistry Tissue microarrays containing samples of normal human skin and SCC were purchased from Biomax US. AKs were collected under a protocol approved by our Institutional Review Board. Antigen retrieval was performed in 0.01 M Na Citrate (pH 6) and the following primary antibodies were used: MAB21L4 (1:500, Biorbyt, orb159238), CacyBP (1:200, Proteintech, 11745-1-AP), RET (1:200, NSJ Bioreagents, F53523). The secondary antibodies used were: goat anti-mouse IgG (ImmPRESS HRP Reagent Kit, Vector, MP-7452), goat anti-rabbit IgG (ImmPRESS HRP Reagent Kit, Vector, MP-7401), followed by the use of the chromogen DAB (ImmPACT DAB Peroxidase Substrate Kit, Vector, SK-4105). Analysis of immunohistochemistry staining was performed in a blinded manner.

Proximity Ligation Assay (PLA) PLA was performed using Duolink PLA reagents (Sigma-Aldrich, DU092008) according to the manufacturer's instructions. Briefly, 7 μm tissue cryosections were fixed in methanol as described above, followed by blocking with the provided blocking buffer and then incubated with primary antibodies against the two proteins of interest. The primary antibodies used for PLA analyses were: MAB21L4 (1:50, Biorbyt, orb159238), CacyBP (1:50, Novus Biologicals, H00027101-B01P), Envoplakin (1:50, Novus Biologicals, NBP2-37940), HA (1:50, BioLegend, 901501), Periplakin (1:50, LSBio, LS-C482731), CacyBP (1:50, Proteintech, 11745-1-AP), RET (1:50, NSJ Bioreagents, F53523), Ubiquitin (1:100, Abcam, ab7780), Siah-1 (1:50, Genetex, GTX113268). After 2 washes, the tissues were incubated with the PLA probes anti-mouse MINUS (Sigma-Aldrich, DU092004) and anti-rabbit PLUS (Sigma-Aldrich, DU092002), followed by the ligation and amplification reactions. Tissues were then mounted with Prolong Gold Antifade Mountant with DAPI (Thermo Fisher Scientific) and imaged using a LSM 880 Airyscan Fast Live Cell inverted confocal microscope (Zeiss).

Images of several z-stacks were acquired and the maximum intensity projection image was generated using the Fiji-ImageJ package. PLA index was calculated as the number of dots divided by the number of nuclei. For quantitation of MAB21L4-Envoplakin and MAB21L4-Periplakin fluorescent signal, the PLA index was calculated as the integrated density of signal divided by number of nuclei. The number of dots and the integrated density were analyzed using the Fiji-ImageJ package.

Co-Immunoprecipitation Protein lysates from human skin organoids were extracted as described in the Western Blotting section. FHH-MAB21L4 protein was immunoprecipitated by incubating 95% of the lysate with anti-Flag M2 Affinity gel (Sigma-Aldrich) at 4° C. under rotation overnight (~16 h). The gel beads were washed 3 times in cold TBS containing protease inhibitors (Sigma-Aldrich) and then eluted in 2× Laemmli Buffer (Bio-Rad) followed by western blotting analysis as previously described. RET was immunoprecipitated from 293T cells by incubating 95% of the lysate with anti-RET Agarose-conjugated mouse monoclonal antibody (Santa Cruz Biotechnology, sc-101423 AC).

Drug Treatments 20 µM MG132 (Fisher Scientific) was added to the growth medium of human skin organoids 3 days post-seeding; 0.1% DMSO was used as a vehicle control. Tissues were harvested for western blotting analysis after treating with MG132 for 12 hours. 15 nM BLU-667 (Carbosynth) was added to the growth medium of human skin organoids for 7 days post-seeding or for 7 days starting one week after seeding. 0.1% DMSO was used as a vehicle control.

Statistical Analysis To visualize somatic deletions at the MAB21L4 locus, publicly available TCGA datasets were downloaded from UCSC Xena post-removal of common germline copy number variation. BEDTools was used to interrogate the MAB21L4 interval using ←−0.25 as the threshold for significant copy number loss. Segments containing genes categorized as tumor suppressors by the COSMIC Cancer Gene Census (version GRCh37) were removed from analysis. The segments were then visualized using the UCSC genome browser. Segments were also used to plot a MAB21L4 deletion frequency percentage measured in 23 TCGA cancer types. For this analysis, SCNAs that overlap with COSMIC Cancer Gene Census tumor suppressors were removed and the graph was plotted using ggplot2 in R76.

To determine MAB21L4's effect on survival, TCGA expression data was downloaded from UCSC Xena. The prognostic potential of MAB21L4 was investigated in lung squamous cell carcinoma (LUSC), cervical cancer (CESC), esophageal cancer (ESCA), and head and neck cancer (HNSC). For each dataset, Cox Proportional Hazards (PH) modeling was used to analyze the relationship between MAB21L4 mRNA expression and overall survival. Age, gender, and clinical stage were included as covariates to adjust for baseline risk differences. Only patients with complete information about age, gender, clinical stage, and MAB21L4 expression were included in the analysis. To maximize degrees of freedom, clinical stages were grouped as Stage I, II, III, or IV. From these 4 cancer types, we found evidence to support MAB21L4 as a prognostic marker in HNSC. The R modeling package rms 5.1-3.1 was used to fit the statistical models. Venn diagrams were generated via eulerr in R. For the 4-way Venn diagram in FIG. 5a, a 0.2 TPM minimum filter was imposed across the replicates of each dataset. A TPM fold change threshold of 1.5 was used to call differential expression. Significance of overlap between separate categories was determined with a permutation resampling approach using 100,000 repetitions. Gene ontology analysis was done using ToppFun from the ToppGene Suite77. T-tests and ANOVA were performed using Prism 8.

REFERENCES

Rogers, H. W., Weinstock, M. A., Feldman, S. R. & Coldiron, B. M. Incidence Estimate of Nonmelanoma Skin Cancer (Keratinocyte Carcinomas) in the U.S. Population, 2012. *JAMA Dermatol* 151, 1081-1086 (2015).

Migden, M. R. et al. PD-1 Blockade with Cemiplimab in Advanced Cutaneous Squamous-Cell Carcinoma. *N. Engl. J. Med.* 379, 341-351 (2018).

Lee, C. S. et al. Recurrent point mutations in the kinetochore gene KNSTRN in cutaneous squamous cell carcinoma. *Nat. Genet.* 46, 1060-1062 (2014).

South, A. P. et al. NOTCH1 mutations occur early during cutaneous squamous cell carcinogenesis. *J. Invest. Dermatol.* 134, 2630-2638 (2014).

Pickering, C. R. et al. Mutational landscape of aggressive cutaneous squamous cell carcinoma. *Clin. Cancer Res.* 20, 6582-6592 (2014).

Wang, N. J. et al. Loss-of-function mutations in Notch receptors in cutaneous and lung squamous cell carcinoma. *Proc. Natl. Acad. Sci. U.S.A.* 108, 17761-17766 (2011).

Brantsch, K. D. et al. Analysis of risk factors determining prognosis of cutaneous squamous-cell carcinoma: a prospective study. *Lancet Oncol.* 9, 713-720 (2008).

Thompson, A. K., Kelley, B. F., Prokop, L. J., Murad, M. H. & Baum, C. L. Risk Factors for Cutaneous Squamous Cell Carcinoma Recurrence, Metastasis, and Disease-Specific Death: A Systematic Review and Meta-analysis. *JAMA Dermatol* 152, 419-428 (2016).

Inohara, S., Kitagawa, K. & Kitano, Y. Expression of cyclin D1 and p53 protein in various malignant skin tumors. *Dermatology (Basel)* 192, 94-98 (1996).

Yamamoto, H. et al. Enhanced skin carcinogenesis in cyclin D1-conditional transgenic mice: cyclin D1 alters keratinocyte response to calcium-induced terminal differentiation. *Cancer Res.* 62, 1641-1647 (2002).

Martinez, L. A., Chen, Y., Fischer, S. M. & Conti, C. J. Coordinated changes in cell cycle machinery occur during keratinocyte terminal differentiation. *Oncogene* 18, 397-406 (1999).

Truong, A. B., Kretz, M., Ridky, T. W., Kimmel, R. & Khavari, P. A. p63 regulates proliferation and differentiation of developmentally mature keratinocytes. *Genes Dev.* 20, 3185-3197 (2006).

Devos, M. et al. Elevated ΔNp63α Levels Facilitate Epidermal and Biliary Oncogenic Transformation. *J. Invest. Dermatol.* 137, 494-505 (2017).

Ishitsuka, Y. & Roop, D. R. Loricrin Confers Photoprotective Function against UVB in Corneocytes. *J. Invest. Dermatol.* 138, 2684-2687 (2018).

Mitsui, H. et al. Gene expression profiling of the leading edge of cutaneous squamous cell carcinoma: IL-24-driven MMP-7. *J. Invest. Dermatol.* 134, 1418-1427 (2014).

Najafi, H., Soltani, B. M., Dokanehiifard, S., Nasiri, S. & Mowla, S. J. Alternative splicing of the OCC-1 gene generates three splice variants and a novel exonic microRNA, which regulate the Wnt signaling pathway. *RNA* 23, 70-85 (2017).

Fang, L., Seki, A. & Fang, G. SKAP associates with kinetochores and promotes the metaphase-to-anaphase transition. *Cell Cycle* 8, 2819-2827 (2009).

Seki, A., Coppinger, J. A., Jang, C.-Y., Yates, J. R. & Fang, G. Bora and the kinase Aurora a cooperatively activate the kinase Plk1 and control mitotic entry. *Science* 320, 1655-1658 (2008).

Suply, T. et al. A natural ligand for the orphan receptor GPR15 modulates lymphocyte recruitment to epithelia. *Sci Signal* 10, (2017).

Kretz, M. et al. Control of somatic tissue differentiation by the long non-coding RNA TINCR. *Nature* 493, 231-235 (2013).

Lee, C. S. et al. Cancer-Associated Long Noncoding RNA SMRT-2 Controls Epidermal Differentiation. *J. Invest. Dermatol.* (2018). doi:10.1016/j.jid.2018.01.003

Sahoo, D., Dill, D. L., Gentles, A. J., Tibshirani, R. & Plevritis, S. K. Boolean implication networks derived from large scale, whole genome microarray datasets. *Genome Biol.* 9, R157 (2008).

Mermel, C. H. et al. GISTIC2.0 facilitates sensitive and confident localization of the targets of focal somatic copy-number alteration in human cancers. *Genome Biol.* 12, R41 (2011).

Baird, S. E., Fitch, D. H., Kassem, I. A. & Emmons, S. W. Pattern formation in the nematode epidermis: determination of the arrangement of peripheral sense organs in the *C. elegans* male tail. *Development* 113, 515-526 (1991).

Chow, K. L., Hall, D. H. & Emmons, S. W. The mab-21 gene of *Caenorhabditis elegans* encodes a novel protein required for choice of alternate cell fates. *Development* 121, 3615-3626 (1995).

Mariani, M. et al. Mab21, the mouse homolog of a *C. elegans* cell-fate specification gene, participates in cerebellar, midbrain and eye development. *Mech. Dev.* 79, 131-135 (1998).

Wong, R. L., Chan, K. K. & Chow, K. L. Developmental expression of Mab21l2 during mouse embryogenesis. *Mech. Dev.* 87, 185-188 (1999).

Wong, R. L. Y. & Chow, K. L. Depletion of Mab21l1 and Mab21l2 messages in mouse embryo arrests axial turning, and impairs notochord and neural tube differentiation. *Teratology* 65, 70-77 (2002).

Yamada, R., Mizutani-Koseki, Y., Koseki, H. & Takahashi, N. Requirement for Mab21l2 during development of murine retina and ventral body wall. *Dev. Biol.* 274, 295-307 (2004).

Sridharan, J., Haremaki, T., Jin, Y., Teegala, S. & Weinstein, D. C. Xmab21l3 mediates dorsoventral patterning in *Xenopus laevis*. *Mech. Dev.* 129, 136-146 (2012).

Takahashi, C., Kusakabe, M., Suzuki, T., Miyatake, K. & Nishida, E. mab21-l3 regulates cell fate specification of multiciliate cells and ionocytes. *Nat Commun* 6, 6017 (2015).

Karagoz, K., Lehman, H. L., Stairs, D. B., Sinha, R. & Arga, K. Y. Proteomic and Metabolic Signatures of Esophageal Squamous Cell Carcinoma. *Curr Cancer Drug Targets* (2016).

Sen, G. L., Webster, D. E., Barragan, D. I., Chang, H. Y. & Khavari, P. A. Control of differentiation in a self-renewing mammalian tissue by the histone demethylase JMJD3. *Genes Dev.* 22, 1865-1870 (2008).

Ramanathan, M. et al. RNA-protein interaction detection in living cells. *Nat. Methods* 15, 207-212 (2018).

Choi, H. et al. SAINT: probabilistic scoring of affinity purification-mass spectrometry data. *Nat. Methods* 8, 70-73 (2011).

Ruhrberg, C., Hajibagheri, M. A., Simon, M., Dooley, T. P. & Watt, F. M. Envoplakin, a novel precursor of the cornified envelope that has homology to desmoplakin. *J. Cell Biol.* 134, 715-729 (1996).

Ruhrberg, C., Hajibagheri, M. A., Parry, D. A. & Watt, F. M. Periplakin, a novel component of cornified envelopes and desmosomes that belongs to the plakin family and forms complexes with envoplakin. *J. Cell Biol.* 139, 1835-1849 (1997).

Sevilla, L. M. et al. Mice deficient in involucrin, envoplakin, and periplakin have a defective epidermal barrier. *J. Cell Biol.* 179, 1599-1612 (2007).

Schneider, G. & Filipek, A. S100A6 binding protein and Siah-1 interacting protein (CacyBP/SIP): spotlight on properties and cellular function. *Amino Acids* 41, 773-780 (2011).

Ridky, T. W., Chow, J. M., Wong, D. J. & Khavari, P. A. Invasive three-dimensional organotypic neoplasia from multiple normal human epithelia. *Nat. Med.* 16, 1450-1455 (2010).

Jameson, K. L. et al. IQGAP1 scaffold-kinase interaction blockade selectively targets RAS-MAP kinase-driven tumors. *Nat. Med.* 19, 626-630 (2013).

Kato, S. et al. RET Aberrations in Diverse Cancers: Next-Generation Sequencing of 4,871 Patients. *Clin. Cancer Res.* 23, 1988-1997 (2017).

Boulay, A. et al. The Ret receptor tyrosine kinase pathway functionally interacts with the ERalpha pathway in breast cancer. *Cancer Res.* 68, 3743-3751 (2008).

Lin, C. et al. Elevated RET expression enhances EGFR activation and mediates EGFR inhibitor resistance in head and neck squamous cell carcinoma. *Cancer Lett.* 377, 1-10 (2016).

Wiesner, T. et al. Kinase fusions are frequent in Spitz tumours and spitzoid melanomas. *Nat Commun* 5, 3116 (2014).

Kato, M. et al. Transgenic mouse model for skin malignant melanoma. *Oncogene* 17, 1885-1888 (1998).

Matsuzawa, S. I. & Reed, J. C. Siah-1, SIP, and Ebi collaborate in a novel pathway for beta-catenin degradation linked to p53 responses. *Mol. Cell* 7, 915-926 (2001).

Bagheri-Yarmand, R., Williams, M. D., Grubbs, E. G. & Gagel, R. F. ATF4 Targets RET for Degradation and Is a Candidate Tumor Suppressor Gene in Medullary Thyroid Cancer. *J. Clin. Endocrinol. Metab.* 102, 933-941 (2017).

Schuchardt, A., D'Agati, V., Larsson-Blomberg, L., Costantini, F. & Pachnis, V. Defects in the kidney and enteric nervous system of mice lacking the tyrosine kinase receptor Ret. *Nature* 367, 380-383 (1994).

Miles, D. C. et al. The proto-oncogene Ret is required for male foetal germ cell survival. *Dev. Biol.* 365, 101-109 (2012).

Perea, D. et al. Ret receptor tyrosine kinase sustains proliferation and tissue maturation in intestinal epithelia. *EMBO J.* 36, 3029-3045 (2017).

Subbiah, V. et al. Precision Targeted Therapy with BLU-667 for RET-Driven Cancers. *Cancer Discovery* 8, 836-849 (2018).

Au, K.-W. et al. Calcyclin binding protein promotes DNA synthesis and differentiation in rat neonatal cardiomyocytes. *J. Cell. Biochem.* 98, 555-566 (2006).

Schneider, G. et al. CacyBP/SIP interacts with tubulin in neuroblastoma NB2a cells and induces formation of globular tubulin assemblies. *Biochim. Biophys. Acta* 1773, 1628-1636 (2007).

Fukushima, T. et al. Critical function for SIP, a ubiquitin E3 ligase component of the beta catenin degradation pathway, for thymocyte development and G1 checkpoint. *Immunity* 24, 29-39 (2006).

Jiang, T.-X. et al. SIP/CacyBP promotes autophagy by regulating levels of BRUCE/Apollon, which stimulates LC3-I degradation. *Proc. Natl. Acad. Sci. U.S.A.* 116, 13404-13413 (2019).

Yoshihara, N. et al. The significant role of autophagy in the granular layer in normal skin differentiation and hair growth. *Arch. Dermatol. Res.* 307, 159-169 (2015).

Akinduro, O. et al. Constitutive Autophagy and Nucleophagy during Epidermal Differentiation. *J. Invest. Dermatol.* 136, 1460-1470 (2016).

Heanue, T. A. & Pachnis, V. Expression profiling the developing mammalian enteric nervous system identifies marker and candidate Hirschsprung disease genes. *Proc. Natl. Acad. Sci. U.S.A.* 103, 6919-6924 (2006).

Cockburn, J. G., Richardson, D. S., Gujral, T. S. & Mulligan, L. M. RET-mediated cell adhesion and migration require multiple integrin subunits. *J. Clin. Endocrinol. Metab.* 95, E342-6 (2010).

Reuter, J. A. et al. Modeling inducible human tissue neoplasia identifies an extracellular matrix interaction network involved in cancer progression. *Cancer Cell* 15, 477-488 (2009).

Carter, J. B., Johnson, M. M., Chua, T. L., Karia, P. S. & Schmults, C. D. Outcomes of primary cutaneous squamous cell carcinoma with perineural invasion: an 11-year cohort study. *JAMA Dermatol* 149, 35-41 (2013).

Mulligan, L. M. GDNF and the RET Receptor in Cancer: New Insights and Therapeutic Potential. *Front Physiol* 9, 1873 (2018).

Labun, K., Montague, T. G., Gagnon, J. A., Thyme, S. B. & Valen, E. CHOPCHOP v2: a web tool for the next generation of CRISPR genome engineering. *Nucleic Acids Res.* 44, W272-6 (2016).

Rubin, A. J. et al. Coupled Single-Cell CRISPR Screening and Epigenomic Profiling Reveals Causal Gene Regulatory Networks. *Cell* 176, 361-376.e17 (2019). Roux, K. J., Kim, D. I. & Burke, B. BioID: a screen for protein-protein interactions. *Curr Protoc Protein Sci* 74, Unit 19.23. (2013).

Teo, G. et al. SAINTq: Scoring protein-protein interactions in affinity purification—mass spectrometry experiments with fragment or peptide intensity data. *Proteomics* 16, 2238-2245 (2016).

Mellacheruvu, D. et al. The CRAPome: a contaminant repository for affinity purification mass spectrometry data. *Nat. Methods* 10, 730-736 (2013).

Dobin, A. et al. STAR: ultrafast universal RNA-seq aligner. *Bioinformatics* 29, 15-21 (2013).

Li, B. & Dewey, C. N. RSEM: accurate transcript quantification from RNA-Seq data with or without a reference genome. *BMC Bioinformatics* 12, 323 (2011).

Love, M. I., Huber, W. & Anders, S. Moderated estimation of fold change and dispersion for RNA-seq data with DESeq2. *Genome Biol.* 15, 550 (2014).

Arocho, A., Chen, B., Ladanyi, M. & Pan, Q. Validation of the 2-DeltaDeltaCt calculation as an alternate method of data analysis for quantitative PCR of BCR-ABL P210 transcripts. *Diagn. Mol. Pathol.* 15, 56-61 (2006).

Schindelin, J. et al. Fiji: an open-source platform for biological-image analysis. *Nat. Methods* 9, 676-682 (2012).

Quinlan, A. R. & Hall, I. M. BEDTools: a flexible suite of utilities for comparing genomic features. *Bioinformatics* 26, 841-842 (2010).

Sondka, Z. et al. The COSMIC Cancer Gene Census: describing genetic dysfunction across all human cancers. *Nat. Rev. Cancer* 18, 696-705 (2018).

Wickham, H. *ggplot2*. (Springer, 2016).

Chen, J., Bardes, E. E., Aronow, B. J. & Jegga, A. G. ToppGene Suite for gene list enrichment analysis and candidate gene prioritization. *Nucleic Acids Res.* 37, W305-11 (2009).

Example 2

Figure 14:
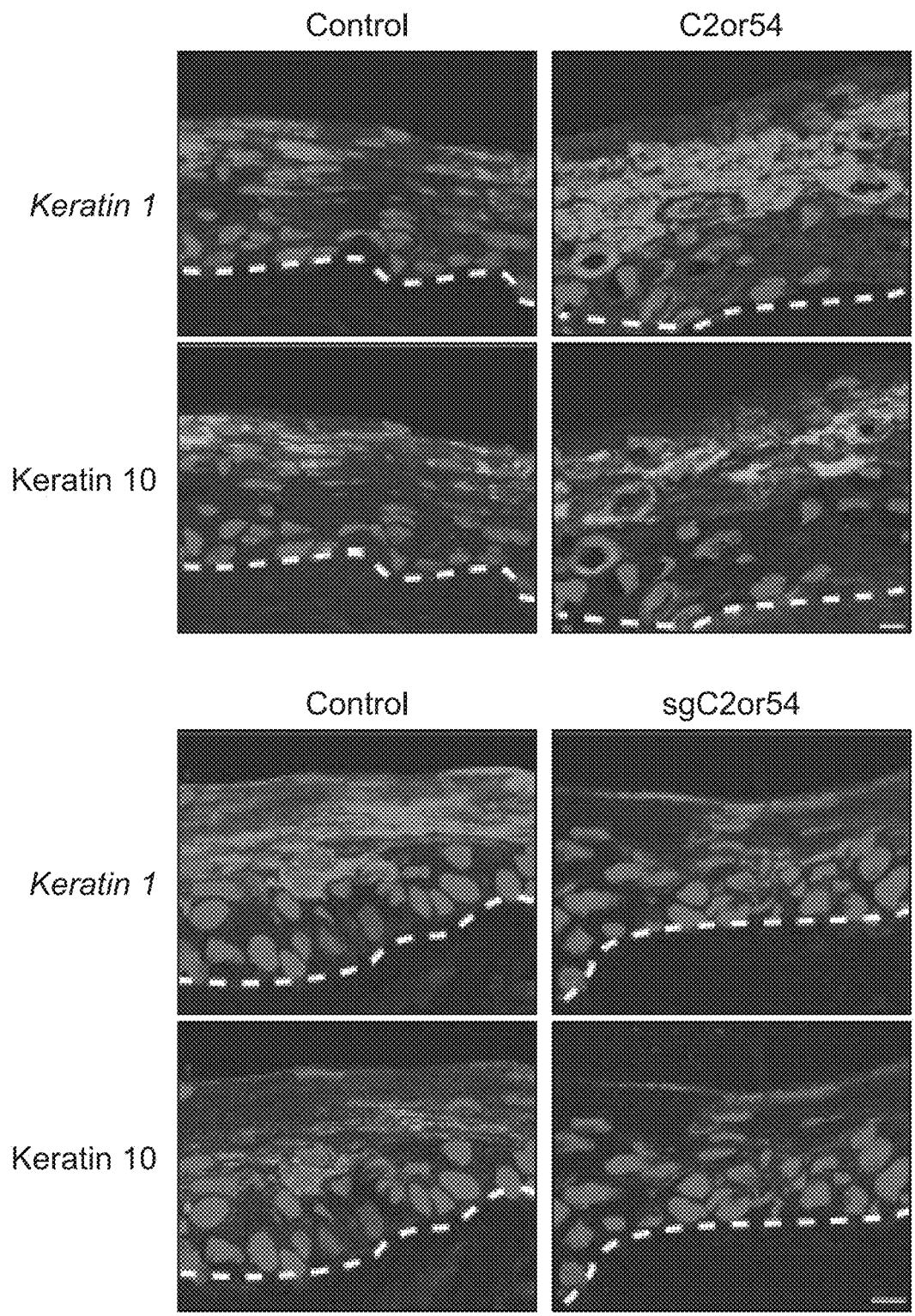
FIG. 14. a) Human skin tissue regenerated from primary keratinocytes transduced to express MAB21L4 (top) or genome-edited keratinocytes where MAB21L4 has been deleted (bottom). b) Somatic MAB21L4 deletion in selected TCGA cancer types. c) Human skin xenografts were regenerated from primary keratinocytes transduced with Cdk4 and Ras to initiate neoplastic transformation. The addition of MAB21L4 decreases invasion (absence of Keratin 5-positive cells beneath the basement membrane), which is quantitated on the right. Yellow arrowheads indicate focal areas of basement membrane degradation.
Figure 14:
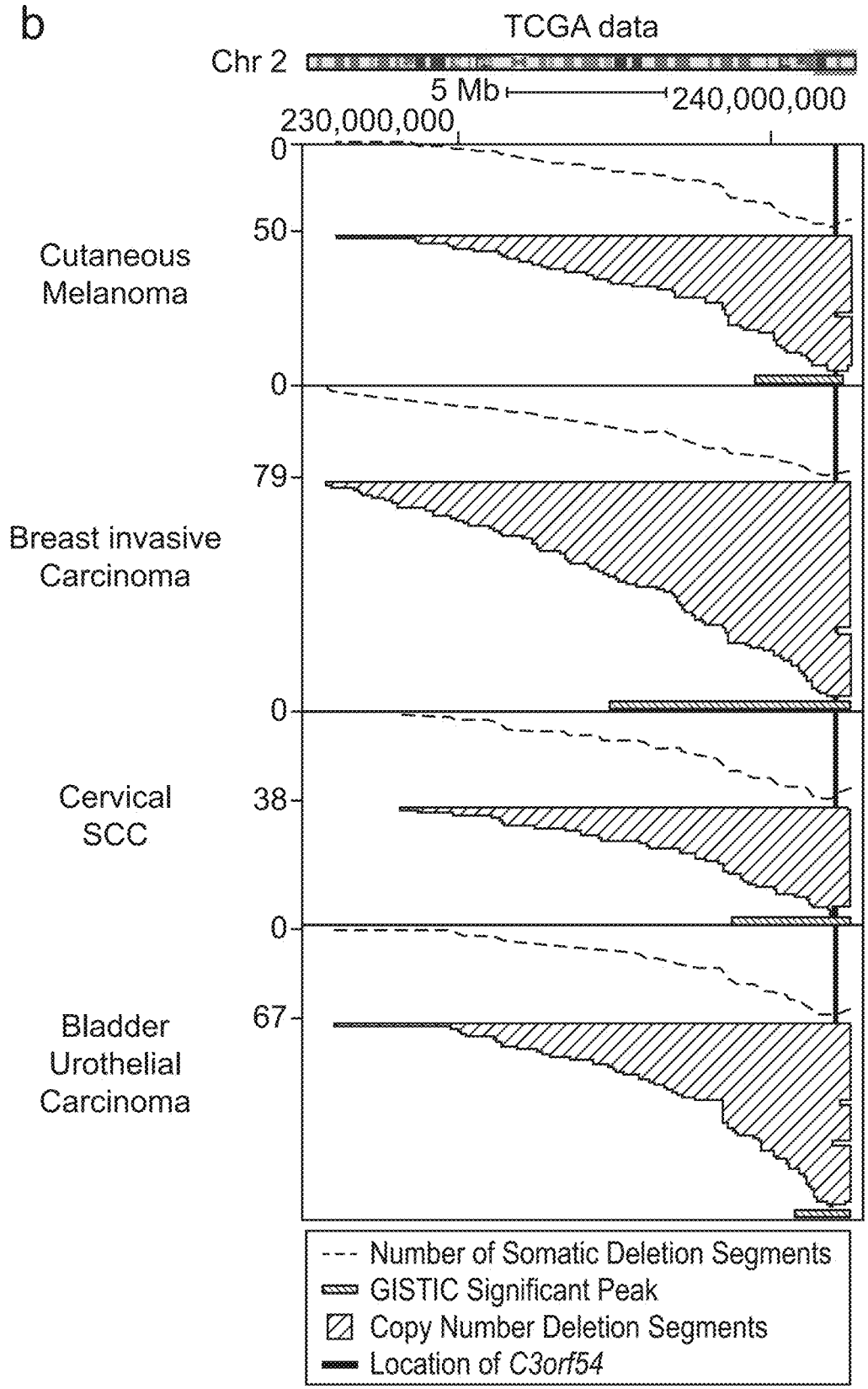
Figure 14:
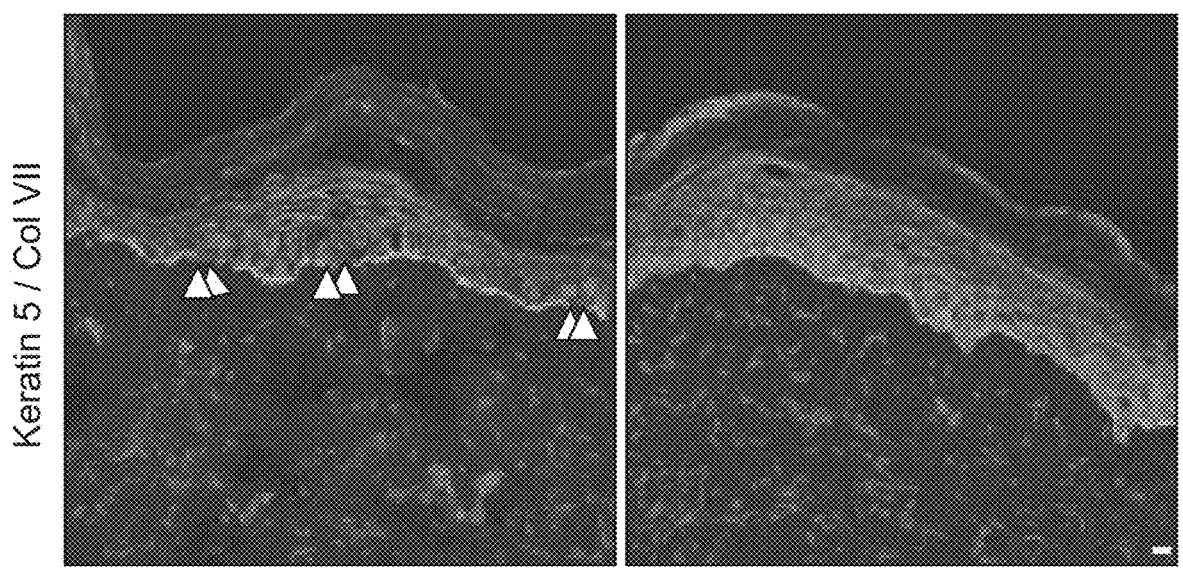
Figure 14:
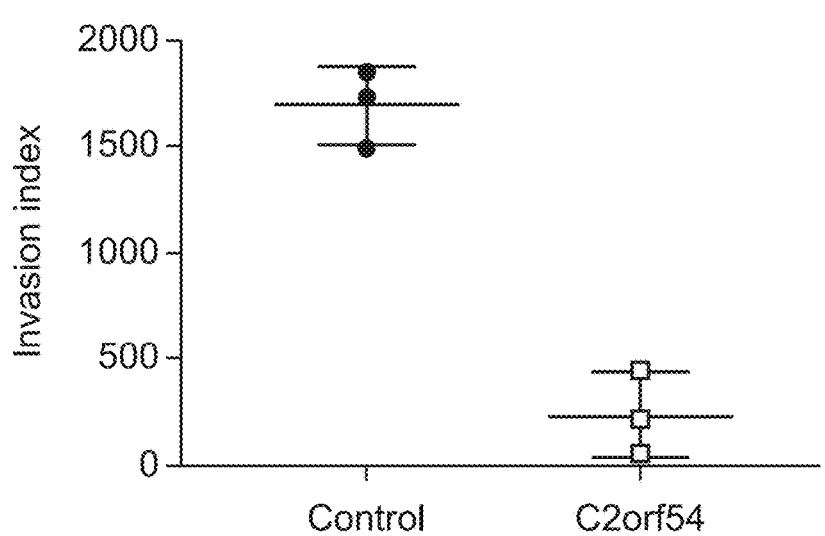

Uncharacterized Protein MAB21L4 is Required for Epidermal Differentiation and Suppression of Cancer Invasion Shown in FIG. 14, MAB21L4 (also referred to as C2orf54) decreases invasion when expressed in transformed keratinocytes. MAB21L4 is the top upregulated open reading frame (ORF) identified in an RNA-Seq screen for uncharacterized ORFs induced during epidermal differentiation. Gain- and loss-of-function experiments in organotypic human epidermal tissue demonstrate the encoded MAB21L4 protein is necessary for differentiation. Proximal proteomics using BioID and performed in organotypic human epidermal tissue identifies MAB21L4 binding to calcyclin binding protein (CacyBP), a component of E3 ubiquitin ligases. MAB21L4-dependent control of epidermal differentiation requires CacyBP. MAB21L4 is down-regulated in cutaneous squamous cell carcinoma (SCC) and frequently deleted in other human malignancies. Gain- and loss-of-function studies in human epidermal tissue indicate a tumor-suppressive role for MAB21L4. MAB21L4 interaction with CacyBP mediates neoplastic invasion in human skin tissue through regulation of Ret. MAB21L4 represents a novel regulator of epidermal differentiation that functions as a tumor suppressor in skin.

While the foregoing has presented specific embodiments, it is to be understood that these embodiments have been presented by way of example only. It is expected that others will perceive and practice variations which, though differing from the foregoing, do not depart form the spirit and scope of the inventions as described and claimed herein. All patent applications, patents, and literature references cited in this specification are hereby incorporated by reference in their entirety. In case of conflict or inconsistency, the present description, including definitions, will control.

What is claimed is:

1. A method for the treatment of a cutaneous squamous cell carcinoma or precancerous lesion in a human individual, the method comprising:
   contacting the cutaneous squamous cell carcinoma or precancerous lesion with an effective dose of a direct RET inhibitor, wherein the cutaneous squamous cell carcinoma or precancerous lesion is characterized by reduced expression of MAB21L4.

2. The method of claim 1, wherein the squamous cell carcinoma is advanced cutaneous squamous cell carcinoma.

3. The method of claim 1, wherein the precancerous lesion is actinic keratosis.

4. The method of claim 1, wherein the method further comprises a step of analyzing the cancer cells for expression of MAB21L4 prior to the contacting step.

5. The method of claim 1, wherein the method further comprises a step of analyzing the cancer cells for loss of one or both MAB21L4 alleles prior to the contacting step.

6. The method of claim 1, wherein the RET inhibitor is a selective RET inhibitor.

7. The method of claim 6, wherein the selective RET inhibitor is pralsetinib or selpercatinib.

8. The method of claim 1, selective RET inhibitor is administered topically.

9. The method of claim 1, wherein progression of the carcinoma is reduced.

10. The method of claim 1, wherein metastasis and invasion of the carcinoma is reduced.

11. The method of claim 10, wherein perineural invasion is reduced.

12. The method of claim 1, wherein the RET inhibitor is a multi-kinase inhibitor selected from cabozantinib, vandetanib, and lenvatinib.

13. A method for the treatment of a cutaneous squamous cell carcinoma characterized by reduced expression of MAB21L4 and increased RET expression or activation, in a human individual, the method comprising:

contacting the cutaneous squamous cell carcinoma characterized by reduced expression of MAB21L4 and increased RET expression or activation with an effective dose of a selective RET inhibitor.

14. The method of claim 13, wherein the selective RET inhibitor is pralsetinib or selpercatinib.

15. A method for the treatment of precancerous actinic keratosis characterized by reduced expression of MAB21L4 and increased RET expression or activation, in a human individual, the method comprising:

contacting the precancerous actinic keratosis characterized by reduced expression of MAB21L4 and increased RET expression or activation, with an effective dose of a selective RET inhibitor.

16. The method of claim 15, wherein the selective RET inhibitor is pralsetinib or selpercatinib.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial sequence
<220> FEATURE:
<223> OTHER INFORMATION: synthetic sequence

<400> SEQUENCE: 1
gaccggaacg atctcgcgta                                              20

<210> SEQ ID NO 2
<211> LENGTH: 20
<212> TYPE: DNA
<213> ORGANISM: Artificial sequence
<220> FEATURE:
<223> OTHER INFORMATION: synthetic sequence
```

```
<400> SEQUENCE: 2
gcagcacgtt ctctgcgcgc                                              20

<210> SEQ ID NO 3
<211> LENGTH: 21
<212> TYPE: DNA
<213> ORGANISM: Artificial sequence
<220> FEATURE:
<223> OTHER INFORMATION: synthetic sequence

<400> SEQUENCE: 3
gagtagtcca cgatgaagcg g                                            21

<210> SEQ ID NO 4
<211> LENGTH: 20
<212> TYPE: DNA
<213> ORGANISM: Artificial sequence
<220> FEATURE:
<223> OTHER INFORMATION: synthetic sequence

<400> SEQUENCE: 4
ttatctgact gatcccatcc                                              20

<210> SEQ ID NO 5
<211> LENGTH: 20
<212> TYPE: DNA
<213> ORGANISM: Artificial sequence
<220> FEATURE:
<223> OTHER INFORMATION: synthetic sequence

<400> SEQUENCE: 5
acttacctct tctgaagcca                                              20

<210> SEQ ID NO 6
<211> LENGTH: 20
<212> TYPE: DNA
<213> ORGANISM: Artificial sequence
<220> FEATURE:
<223> OTHER INFORMATION: synthetic sequence

<400> SEQUENCE: 6
tcctcgtcgt acacggtcac                                              20

<210> SEQ ID NO 7
<211> LENGTH: 20
<212> TYPE: DNA
<213> ORGANISM: Artificial sequence
<220> FEATURE:
<223> OTHER INFORMATION: synthetic sequence

<400> SEQUENCE: 7
tggcgtactc cacgatgagg                                              20
```